US012220458B2

(12) United States Patent
Uchida et al.

(10) Patent No.: US 12,220,458 B2
(45) Date of Patent: Feb. 11, 2025

(54) ANTIGEN-SURFACE-COUPLED LIPOSOME VACCINE FOR NON-HUMAN ANIMALS

(71) Applicants: NATIONAL FEDERATION OF AGRICULTURAL COOPERATIVE ASSOCIATIONS, Tokyo (JP); Tetsuya Uchida, Saitama (JP)

(72) Inventors: Tetsuya Uchida, Saitama (JP); Makoto Nakanishi, Sakura (JP); Ryouichi Shima, Sakura (JP); Takanori Namimatsu, Sakura (JP); Goro Suzuki, Sakura (JP)

(73) Assignees: NATIONAL FEDERATION OF AGRICULTURAL COOPERATIVE ASSOCIATIONS, Tokyo (JP); Tetsuya Uchida, Saitama (JP)

( * ) Notice: Subject to any disclaimer, the term of this patent is extended or adjusted under 35 U.S.C. 154(b) by 1140 days.

(21) Appl. No.: 16/964,809

(22) PCT Filed: Jan. 24, 2019

(86) PCT No.: PCT/JP2019/002339
§ 371 (c)(1),
(2) Date: Jan. 22, 2021

(87) PCT Pub. No.: WO2019/146716
PCT Pub. Date: Aug. 1, 2019

(65) Prior Publication Data
US 2021/0138064 A1    May 13, 2021

(30) Foreign Application Priority Data

Jan. 26, 2018 (JP) ................................ 2018-011939

(51) Int. Cl.
| | |
|---|---|
| *A61K 39/385* | (2006.01) |
| *A61K 39/12* | (2006.01) |
| *A61K 39/215* | (2006.01) |
| *A61K 47/69* | (2017.01) |
| *A61P 31/14* | (2006.01) |
| *A61K 39/00* | (2006.01) |

(52) U.S. Cl.
CPC .......... *A61K 39/385* (2013.01); *A61K 39/12* (2013.01); *A61K 39/215* (2013.01); *A61K 47/6911* (2017.08); *A61P 31/14* (2018.01); *A61K 2039/545* (2013.01); *A61K 2039/552* (2013.01); *A61K 2039/572* (2013.01); *A61K 2039/575* (2013.01); *A61K 2039/6018* (2013.01); *C12N 2770/10034* (2013.01); *C12N 2770/10071* (2013.01); *C12N 2770/20034* (2013.01); *C12N 2770/20071* (2013.01)

(58) Field of Classification Search
CPC .......... A61K 39/215; A61K 2039/6018; A61K 2039/55555; C12N 2770/20034
See application file for complete search history.

(56) References Cited

U.S. PATENT DOCUMENTS

| | | |
|---|---|---|
| 2002/0037292 A1 | 3/2002 | Audonnet et al. |
| 2010/0136098 A1 | 6/2010 | Uchida et al. |

FOREIGN PATENT DOCUMENTS

| | | |
|---|---|---|
| CN | 1701788 A | 11/2005 |
| CN | 105073130 A | 11/2015 |
| JP | 8-183742 A | 7/1996 |
| JP | 9-12480 A | 1/1997 |
| JP | 2004-43332 A | 2/2004 |
| JP | 2008-231123 A | 10/2008 |
| JP | 2011-128853 A | 6/2011 |
| JP | 2013-188699 A | 8/2013 |
| JP | 2014-5205 A | 1/2014 |
| WO | WO 2012/033142 A1 | 3/2012 |
| WO | 2014/150822 A2 | 9/2014 |

OTHER PUBLICATIONS

Tan, Y. W., et al., 2006, Amino acid residues critical for RNA-binding in the N-terminal domain of the nucleocapsid protein are essential determinants for the infectivity of coronavirus in cultured cells, Nucleic Acids Res. 34(17):4816-4825.*
Wootton, S., et al., May 2001, Antigenic Importance of the Carboxy-Terminal Beta-Strand of the Porcine Reproductive and Respiratory Syndrome Virus Nucleocapsid Protein, Clin. Diag. Lab. Immunol. 8(3):598-603.*
Yaguchi, K., et al., 2009, Vaccination of Chickens with Liposomal Inactivated Avian Pathogenic *Escherichia coli* (APEC) vaccine by Eye Drop or Coarse Spray Administration, Avian Dis. 53:245-249.*
Ignjatovic, J., and S. Sapats, 2005, Identification of previously unknown antigenic epitopes on the S and N proteins of avian infectious bronchitis virus, Arch. Virol. 150:1813-1831.*

(Continued)

*Primary Examiner* — Jeffrey S Parkin
(74) *Attorney, Agent, or Firm* — Birch, Stewart, Kolasch & Birch, LLP

(57) ABSTRACT

Disclosed is a vaccine for non-human animals, which vaccine enables effective immune induction in non-human animals such as livestock or poultry. The vaccine for non-human animals of the present invention comprises liposomes each comprising an antigen molecule(s) bound to the surface thereof, the antigen molecule(s) being derived from a pathogen infectious to the non-human animals. The non-human animals are, for example, livestock or poultry. One most preferred example of the vaccine according to the present invention is an infectious bronchitis virus (IBV) vaccine, which is effective against various isolated IBV strains, and which is expected to be sufficiently applicable even to cases where a mutant strain appeared. Another preferred example of the vaccine according to the present invention is a PRRSV vaccine, which was confirmed to have an effect that reduces fever, lung lesion development, and the like caused by the infection. The present invention enables development of liposome vaccines effective for prevention of infections caused by various non-human animal pathogens including PRRSV as well as IBV.

10 Claims, 27 Drawing Sheets
Specification includes a Sequence Listing.

(56) References Cited

OTHER PUBLICATIONS

Uchida, T., and M. Taneichi, 2014, Application of Surface-Linked Liposomal Antigens to the Development of Vaccines That Induce Both Humoral and Cellular Immunity, Jpn. J. Infect. Dis. 67:235-244.*

Bande et al., "Progress and Challenges toward the Development of Vaccines against Avian Infectious Bronchitis," Journal of Immunology Research, vol. 15, No. 2, Article ID 424860, Jan. 2015, XP055323940, pp. 1-12.

Calderon-Nieva et al., "Veterinary vaccine nanotechnology: pulmonary and nasal delivery in livestock animals," Drug Delivery and Translational Research, vol. 7, No. 4, Jun. 21, 2017, XP037125831, pp. 558-570 (13 pages total).

Extended European Search Report for European Application No. 19743855.9, dated Feb. 1, 2022.

Kobierecka et al., "Chicken Anti-Campylobacter Vaccine—Comparison of Various Carriers and Routes of Immunization," Frontiers in Microbiology, vol. 7, Article 740, May 2016, XP055874825, pp. 1-13.

Nagata et al., "Peptides coupled to the surface of a kind of liposome protect infection of influenza viruses, " Vaccine, Elsevier, vol. 25, No. 26, Amsterdam, NL, Jun. 2007, XP022101827, pp. 4914-4921 (8 pages total).

Naito et al., "Ovalbumin-liposome Conjugate Induces IgG but Not IgE Antibody Production," International Archives of Allergy and Immunology, vol. 109, 1996, pp. 223-228 (6 pages total).

Nakano et al., "Antigen-Specific, IgE-Selective Unresponsiveness Induced by Antigen-Liposome Conjugates," International Archives of Allergy and Immunology, vol. 120, 1999, pp. 199-208 (10 pages total).

Nan et al., "Improved Vaccine against PRRSV: Current Progress and Future Perspective," Frontiers in Microbiology, vol. 8, Aug. 2017, XP055875048, pp. 1-17.

Schwendener, "Liposomes as vaccine delivery systems: a review of the recent advances," Therapeutic Advances in Vaccines, vol. 2, No. 6, Jan. 2014, XP055874534, pp. 159-182 (24 pages total).

Seo et al., "The Carboxyl-Terminal 120-Residue Polypeptide of Infectious Bronchitis Virus Nucleocapsid Induces Cytotoxic T Lymphocytes and Protects Chickens from Acute Infection," Journal of Virology, vol. 71, No. 10, Oct. 1997, pp. 7889-7894 (6 pages total).

Shieh et al., "Complete Nucleotide Sequences of S1 and N Genes of Infectious Bronchitis Virus Isolated in Japan and Taiwan," Journal of Veterinary Medicine and Science, vol. 66, No. 5, 2004, pp. 555-558 (4 pages total).

Supervised by Kamiya, "Advanced Applications for Vaccine Manufacturing," CMC Publishing Co., Ltd. 2010, pp. 124-133 (13 pages total), with partial English translation.

Tanaka et al., "Liposomes with Differential Lipid Components Exert Differential Adjuvanticity in Antigen-Liposome Conjugates via Differential Recognition by Macrophages," Bioconjugate Chem., vol. 15, No. 1, 2004, pp. 35-40 (6 pages total).

Uchida et al., "Application of Surface-Linked Liposomal Antigens to the Development of Vaccines That Induce Both Humoral and Cellular Immunity," Japanese Journal of Infectious Diseases, vol. 67, No. 4. Jan. 2014, XP055874971, pp. 235-244 (10 pages total).

Uchida, "Development of CTL-based liposomal vaccines," Drug Delivery System, vol. 25, No. 1, 2010, pp. 29-36 (14 pages total), with partial English translation.

Yaguchi et al., "Vaccination of Chickens with Liposomal Inactivated Avian Pathogenic *Escherichia coli* (APEC) Vaccine by Eye Drop or Coarse Spray Administration," Avian Diseases, vol. 53, Jun. 2009, XP055874577, pp. 245-249 (5 pages total).

Yoon et al., "Genetic characterization of the Korean porcine reproductive and respiratory syndrome viruses based on the nucleocapsid protein gene (ORF7) sequences," Arch Virol, vol. 153, No. 4, 2008, pp. 627-635 (9 pages total).

* cited by examiner

① ② ③ ④ ⑤ ⑥ ⑦ ⑧ (kDa)

← 75
← 50
← 37

① Whole bacterial cells before induction
② Whole bacterial cells after induction
③ Soluble fraction
④ Pass-through fraction
⑤ Wash fraction (first time)
⑥ Wash fraction (second time)
⑦ Eluted fraction
⑧ Markers Induction of expression, and purification of recombinant N protein (IBV-rNp)

Fig.1

① ② ③ ④ ⑤ ⑥ ⑦ (kDa)

← 75
← 50
← 37

① Whole bacterial cells before induction
② Whole bacterial cells after induction
③ Soluble fraction
④ Pass-through fraction
⑤ Wash fraction
⑥ Eluted fraction
⑦ Markers Induction of expression, and purification of recombinant M protein (IBV-rMp)

Fig.2

Score: 0 = active movement; 1 = rather weak; 2 = very weak/partial movement; 3= arrest

Fig.4-1

| Positive ratio as measured by real-time PCR (%) | | | | | |
|---|---|---|---|---|---|
| Organ | rNp-DSS | rNp-GA | rMp-DSS | rMp-GA | Live vaccine | Control |
| Trachea | 100 | 100 | 100 | 100 | 100 | 100 |
| Kidney | 100 | 100 | 100 | 100 | 100 | 100 |

Viral gene in organs

Fig.4-2

| Average virus titers in isolation-positive samples | | | | | | |
|---|---|---|---|---|---|---|
|  | rNp-DSS | rNp-GA | rMp-DSS | rMp-GA | Live vaccine | Control |
| Trachea | 3.55 | 4.05 | 4.4 | 4.18 | ND | 4.45 |
| Kidney | 3.3 | 3.55 | 3.97 | 3.55 | ND | 4.18 |

Isolation/quantification of virus from organs
1) Average virus titers in isolation-positive samples (log $TCID_{50}$/g)
2) Below detection limit (<2.8)

Amounts of viral gene in organs

Isolation of virus from organs

Amounts of viral gene in organs

Isolation of virus from organs

Virus titers in organs

※For samples with virus titers under the detection limit (2.8 $logTCID_{50}/g$), the virus titer was regarded as 2.8.

※For samples with virus titers under the detection limit (2.8 logTCID$_{50}$/g), the virus titer was regarded as 2.8.

Virus titers in organs

Schematic diagram illustrating fragmentation of IBV nucleocapsid gene

Fig.8-1

Schematic diagram illustrating the chimeric protein (N+M)

Fig.8-2

Score: 0 = active movement; 1 = rather weak; 2 = very weak/partial movement; 3= arrest

Amounts of viral gene in organs

Score: 0 = active movement; 1 = rather weak; 2 = very weak/partial movement; 3= arrest Changes in the egg-laying rate Changes in the egg-laying rate through different periods Amounts of viral gene in buccal/cloacal swabs Amounts of viral gene in organs (7 dPI, 2 chickens/group)

Tracheal ciliary movement score (7 dPI, 2 chickens/group)

Score: 0 = active movement; 1 = rather weak; 2 = very weak/partial movement; 3= arrest ELISA antibody titer
Positive at 0.2 ≤ S/P ratio \* Significant difference from Group 3 (<0.05)
\*\* Significant difference from Group 3 (<0.01)

Score: 0 = active movement; 1 = rather weak; 2 = very weak/partial movement; 3= arrest Amounts of viral gene in organs Confirmation of expression of PRRSV-rNp [assumed molecular weight, 14 kDa]
(left, CBB staining; right, Western blotting using a mouse anti-PRRSV-rNp antibody)

Fig.15-1

Test schedule

Fig.16-1

ELISPOT for detection of IFN-γ

Fig.16-2

ELISA for detection of IgG

Fig.16-3

ELISA for detection of IgG1

Fig.16-4

ELISA for detection of IgG2a

Fig.16-5

Test schedule dPI: day Post Immunization    , dPC: day Post Challenge

Changes in the body temperature score

* Significant difference (p<0.05)

Amount of viral gene in blood

ELISPOT for detection of porcine IFN-γ

ELISA for detection of porcine IFN-γ

Fig.17-5

| Lung lesion image | Score |
|---|---|
| No lesion | 0 |
| Mild interstitial pneumonia | 1 |
| Moderate multifocal interstitial pneumonia | 2 |
| Moderate diffuse interstitial pneumonia | 3 |
| Severe interstitial pneumonia | 4 |

Lung lesion score

Fig.17-6

Antibody titer against PRRSV-rNp (ELISA)

Fig.17-7

ANTIGEN-SURFACE-COUPLED LIPOSOME VACCINE FOR NON-HUMAN ANIMALS

TECHNICAL FIELD

The present invention relates to a vaccine for non-human animals, especially a vaccine for poultry against IBV or a vaccine for pigs against PRRSV, which vaccine comprises a liposome having a pathogen-derived antigen molecule(s) bound to the surface thereof.

BACKGROUND ART

Avian infectious bronchitis (IB) is a disease caused by infectious bronchitis virus (IBV), which belongs to the genus *Coronavirus*. IB causes not only respiratory symptoms, but also abnormalities in egg laying, nephritis, and the like. IB is one of the diseases requiring the most urgent countermeasures in the poultry industry. For prevention of IB, a variety of live vaccines and inactivated vaccines have been developed and used. However, because of the diversity and complexity of the antigenicity of IBV, and because of frequent occurrence of mutations, IB cannot be easily controlled in farms even by use of the vaccines.

Porcine reproductive and respiratory syndrome (PRRS) is a disease caused by infection with PRRS virus, and characterized by reproductive disorders of female pigs and respiratory diseases of juvenile pigs. Occurrence of PRRS was found in the United States in 1987, and then in Europe in 1990. It has now spread worldwide, causing abortion and stillbirth, and death of juvenile pigs, resulting in a huge economic loss in the pig industry. At present, the PRRS virus prevalent in Japan is mostly of the North American type, and a vaccine based on type 2 of the North American type PRRS virus is commercially available in Japan. The North American type PRRS virus includes a number of genotypes (at least live groups) due to the diversity of ORF5, and it is reported that the vaccine effect decreases for a virus having a genotype different from the genotype of the vaccine strain. Thus, a vaccine whose effect is not affected by the difference in the genotype is still demanded.

As vaccines for prevention of infections in humans and animals, liposome vaccines using a liposome as an antigen molecule carrier are known. In the conventional clinical studies of liposome vaccines, the liposome vaccines have a structure in which an antigen is encapsulated in a liposome. Thereafter, techniques for binding an antigen to the liposome surface have been developed, resulting in achievement of further improvement of the immunogenicity (Non-Patent Documents 1 to 4). In general, inactivated antigens induce only humoral immunity. It is known, however, that binding of an antigen to the liposome surface allows induction of both humoral immunity and cell-mediated immunity, to enhance the vaccine effect. Studies of liposome vaccines having an antigen bound to the surface thereof are in progress for vaccines against human viruses (such as influenza viruses, hepatitis C viruses, and Ebola viruses) and for cancer vaccines (for example, Patent Documents 1 to 3).

On the other hand, major liposome vaccines for animals are still in the antigen-encapsulated form, and commercially available liposome vaccines for animals are also in the antigen-encapsulated form. No liposome vaccines against IBV or PRRSV have yet been developed.

PRIOR ART DOCUMENTS

Patent Documents

Patent Document 1: JP 2004-043332 A
Patent Document 2: WO 2012/033142
Patent Document 3: JP 2014-005205 A

Non-Patent Documents

Non-Patent Document 1: Advanced Applications for Vaccine Manufacturing, supervised by Hitoshi Kamiya, published by CMC Publishing Co., Ltd. (2010).
Non-Patent Document 2: Nakano et al., Int Arch Allergy Immunol. 1999, vol. 120, p. 199-208
Non-Patent Document 3: Naito et al., Int Arch Allergy Immunol. 1996, vol. 109, p. 223-228
Non-Patent Document 4: Tanaka et al., Bioconjugate Chem. 2004, vol. 15, p. 35-40

SUMMARY OF THE INVENTION

Problems to be Solved by the Invention

An object of the present invention is to provide a vaccine for non-human animals, which vaccine enables effective immune induction in non-human animals such as livestock or poultry, especially to provide an IBV vaccine effective against IBVs having various antigenicities, and a PRRSV vaccine effective against PRRSVs having various genotypes.

Means for Solving the Problems

The present inventors intensively analyzed sequences of viral proteins of various isolated IBV strains, and focused on nucleocapsid protein (N protein), which is highly conserved among known strains, as an antigen region with which a wide range of mutant strains can be covered. The present inventors then prepared a liposome vaccine having the antigen bound to the surface. Subsequently, the present inventors intensively studied the antigen region of N protein, administration route, number of doses, and the like, and succeeded in development of an IBV liposome vaccine which is effective also against various highly virulent IBV strains, and which is effective also for chicks at an early stage after hatching, whose development of the immune system is immature. Further, the present inventors discovered that a similar technique can be applied to development of various vaccines for non-human animals, such as PRRSV liposome vaccines, thereby completing the present invention.

Thus, the present invention provides a vaccine for non-human animals, comprising liposomes each comprising an antigen molecule(s) bound to the surface thereof, the antigen molecule(s) being derived from a pathogen infectious to the non-human animals.

Effect of the Invention

According to the present invention, a vaccine for non-human animals, which vaccine is effective for prevention of infections of non-human animals such as livestock and poultry, is provided. One most preferred example of the vaccine according to the present invention is an IBV vaccine, which is effective against various isolated IBV strains, and which is expected to be sufficiently applicable even to cases where a mutant strain appeared. The IBV vaccine of the present invention has been found to be effective also for chicks at an early stage after hatching, especially newborn chicks, whose development of the immune system is immature. Thus, the vaccine is practically highly useful. The PRRSV vaccine, which is another preferred example of the vaccine according to the present invention, has been found to have an effect that reduces fever, lung lesion development, and the like caused by the infection. Application of the technique enables development of liposome vaccines effective for prevention of infections caused by various non-human animal pathogens including PRRSV as well as IBV.

BRIEF DESCRIPTION OF THE DRAWINGS

FIG. 1 shows the result of SDS-PAGE for confirmation of induction of expression, and purification, of a recombinant IBV N protein (IBV-rNp).

FIG. 2 shows the result of SDS-PAGE for confirmation of induction of expression, and purification, of a recombinant IBV M protein (IBV-rMp).

FIG. 3-1 shows the result of measurement of the antigen-specific IFN-γ production-inducing ability in test chickens to which a test vaccine (BV-rNp-DSS or IBV-rNp-GA) was administered, which measurement was carried out by collecting lymphocytes from the spleen and then performing ELISPOT for detection of chicken IFN-γ.

FIG. 3-2 shows the result of measurement of the antigen-specific IFN-γ production-inducing ability in test chickens to which a test vaccine (IBV-rMp-DSS or IBV-rMp-GA) was administered, which measurement was carried out by collecting lymphocytes from the spleen and then performing ELISPOT for detection of chicken IFN-γ.

FIG. 3-3 shows the result of measurement of the blood antibody titers before and after immunization of test chickens by inoculation of test vaccines, which measurement was carried out by ELISA using IBV-rNp as an antigen.

FIG. 3-4 shows the result of measurement of the blood antibody titers before and after immunization of test chickens by inoculation of test vaccines, which measurement was carried out by ELISA using IBV-rMp as an antigen.

FIG. 4-1 shows the result of evaluation of the effect of vaccine administration in chickens subjected to administration of test vaccines and viral challenge according to the test group setting and the schedule shown in Table 4-1 and Table 4-2, which evaluation was based on the tracheal ciliary movement score.

FIG. 4-2 shows the result of measurement of the amount of viral gene in organs of chickens subjected to administration of test vaccines and viral challenge according to the test group setting and the schedule shown in Table 4-1 and Table 4-2.

FIG. 4-3 shows the result of investigation of the virus isolation rates from organs and the virus titers in isolation-positive samples, which investigation was carried out for chickens subjected to administration of test vaccines and viral challenge according to the test group setting and the schedule shown in Table 4-1 and Table 4-2.

FIG. 4-4 shows the result of measurement of the neutralizing antibody titer in chickens subjected to administration of test vaccines and viral challenge according to the test group setting and the schedule shown in Table 4-1 and Table 4-2, which measurement was carried out at the times of the challenge and autopsy.

FIG. 5-1 shows the result of evaluation of the effect of vaccine administration in chickens subjected to administration of test vaccines and viral challenge according to the test group setting and the schedule shown in Table 5-1 and Table 5-2, which evaluation was based on the tracheal ciliary movement score.

FIG. 5-2 shows the result of measurement of the amount of viral gene in organs of chickens subjected to administration of test vaccines and viral challenge according to the test group setting and the schedule shown in Table 5-1 and Table 5-2.

FIG. 5-3 shows the result of investigation of the virus isolation rates from organs of chickens subjected to administration of test vaccines and viral challenge according to the test group setting and the schedule shown in Table 5-1 and Table 5-2.

FIG. 5-4 shows the result of investigation of the virus titers in organs of chickens subjected to administration of test vaccines and viral challenge according to the test group setting and the schedule shown in Table 5-1 and Table 5-2.

FIG. 6-1 shows the result of evaluation of the effect of vaccine administration in chickens subjected to administration of a test vaccine and viral challenge according to the test group setting and the schedule shown in Table 6-1 and Table 6-2, which evaluation was based on the tracheal ciliary movement score.

FIG. 6-2 shows the result of measurement of the amount of viral gene in organs of chickens subjected to administration of a test vaccine and viral challenge according to the test group setting and the schedule shown in Table 6-1 and Table 6-2.

FIG. 6-3 shows the result of investigation of the virus isolation rates from organs of chickens subjected to administration of a test vaccine and viral challenge according to the test group setting and the schedule shown in Table 6-1 and Table 6-2.

FIG. 6-4 shows the result of investigation of the virus titers in organs of chickens subjected to administration of a test vaccine and viral challenge according to the test group setting and the schedule shown in Table 6-1 and Table 6-2.

FIG. 7-1 shows the result of evaluation of the effect of vaccine administration in chickens subjected to administration of a test vaccine and viral challenge according to the test group setting and the schedule shown in Table 7-1 and Table 7-2, which evaluation was based on the tracheal ciliary movement score.

FIG. 7-2 shows the result of measurement of the amount of viral gene in organs of chickens subjected to administration of a test vaccine and viral challenge according to the test group setting and the schedule shown in Table 7-1 and Table 7-2.

FIG. 7-3 shows the result of investigation of the virus isolation rates from organs of chickens subjected to administration of a test vaccine and viral challenge according to the test group setting and the schedule shown in Table 7-1 and Table 7-2.

FIG. 7-4 shows the result of investigation of the virus titers in organs of chickens subjected to administration of a test vaccine and viral challenge according to the test group setting and the schedule shown in Table 7-1 and Table 7-2.

FIG. 8-1 is a schematic diagram illustrating the recombinant IBV N protein fragments prepared in Examples.

FIG. 8-2 is a schematic diagram illustrating the chimeric protein of IBV N protein and IBV M protein prepared in Examples.

FIG. 8-3 shows the result of evaluation of the effect of vaccine administration in chickens subjected to administration of test vaccines and viral challenge according to the test group setting and the schedule shown in Table 8-1 and Table 8-2, which evaluation was based on the tracheal ciliary movement score.

FIG. 8-4 shows the result of measurement of the amount of viral gene in organs of chickens subjected to administration of test vaccines and viral challenge according to the test group setting and the schedule shown in Table 8-1 and Table 8-2.

FIG. 9-1 shows the result of evaluation of the effect of vaccine administration in chickens subjected to administration of a test vaccine and viral challenge according to the test group setting and the schedule shown in Table 9-1 and Table 9-2, which evaluation was based on the tracheal ciliary movement score.

FIG. 9-2 shows the result of measurement of the amount of viral gene in organs of chickens subjected to administration of a test vaccine and viral challenge according to the test group setting and the schedule shown in Table 9-1 and Table 9-2.

FIG. 10-1 shows the result of evaluation of the effect of vaccine administration in chickens subjected to administration of test vaccines and viral challenge according to the test group setting and the schedule shown in Table 10-1 and Table 10-2, which evaluation was based on the tracheal ciliary movement score.

FIG. 10-2 shows the result of measurement of the amount of viral gene in organs of chickens subjected to administration of test vaccines and viral challenge according to the test group setting and the schedule shown in Table 10-1 and Table 10-2.

FIG. 11-1 shows the result of evaluation of the effect of vaccine administration in chickens subjected to administration of a test vaccine and viral challenge according to the test group setting and the schedule shown in Table 11-1 and Table 11-2, which evaluation was based on the tracheal ciliary movement score.

FIG. 11-2 shows the result of measurement of the amount of viral gene in organs of chickens subjected to administration of a test vaccine and viral challenge according to the test group setting and the schedule shown in Table 11-1 and Table 11-2.

FIG. 12-1 shows the result of evaluation of the effect of vaccine administration in chickens subjected to administration of a test vaccine and viral challenge according to the test group setting and the schedule shown in Table 12-1 and Table 12-2, which evaluation was based on the tracheal ciliary movement score.

FIG. 12-2 shows the result of measurement of the amount of viral gene in organs of chickens subjected to administration of a test vaccine and viral challenge according to the test group setting and the schedule shown in Table 12-1 and Table 12-2.

FIG. 13-1 shows changes in the egg-laying rate in each test group of chickens subjected to administration of a test vaccine and viral challenge according to the test group setting and the schedule shown in Table 13-1 and Table 13-2.

FIG. 13-2 shows changes in the egg-laying rate through different periods in chickens subjected to administration of a test vaccine and viral challenge according to the test group setting and the schedule shown in Table 13-1 and Table 13-2.

FIG. 13-3 shows the result of measurement of the amount of viral gene in buccal/cloacal swabs of chickens subjected to administration of a test vaccine and viral challenge according to the test group setting and the schedule shown in Table 13-1 and Table 13-2.

FIG. 13-4 shows the result of measurement of the amount of viral gene in organs of chickens subjected to administration of a test vaccine and viral challenge according to the test group setting and the schedule shown in Table 13-1 and Table 13-2.

FIG. 13-5 shows the result of evaluation of the effect of vaccine administration in chickens subjected to administration of test vaccines and viral challenge according to the test group setting and the schedule shown in Table 13-1 and Table 13-2, which evaluation was based on the tracheal ciliary movement score.

FIG. 13-6 shows the result of measurement of the serum ELISA antibody titer in chickens subjected to administration of test vaccines and viral challenge according to the test group setting and the schedule shown in Table 13-1 and Table 13-2.

FIG. 14-1 shows the result of evaluation of the effect of vaccine administration in chickens subjected to administration of a test vaccine and challenge by various viral strains according to the test group setting and the schedule shown in Table 14-1 and Table 14-2, which evaluation was based on the tracheal ciliary movement score.

FIG. 14-2 shows the result of measurement of the amount of viral gene in organs of chickens subjected to administration of a test vaccine and challenge by various viral strains according to the test group setting and the schedule shown in Table 14-1 and Table 14-2.

FIG. 15-1 shows the result of SDS-PAGE for confirmation of induction of expression, and purification, of a recombinant PRRSV N protein (PRRSV-rNp).

FIG. 16-1 shows the test schedule for the animal test in "16. Evaluation of Immunogenicity of PRRS Liposome Vaccine Using Mice".

FIG. 16-2 shows the result of measurement of the antigen-specific IFN-γ production-inducing ability in mice to which each immunizing material was administered, which measurement was carried out by collecting lymphocytes from the spleen and then performing ELISPOT for detection of mouse IFN-γ.

FIG. 16-3 shows the result of measurement of the blood IgG antibody titer in mice to which each immunizing material was inoculated, which measurement was carried out by ELISA using PRRSV-rNp as an antigen.

FIG. 16-4 shows the result of measurement of the blood IgG1 antibody titer in mice to which each immunizing material was inoculated, which measurement was carried out by ELISA using PRRSV-rNp as an antigen.

FIG. 16-5 shows the result of measurement of the blood IgG2a antibody titer in mice to which each immunizing material was inoculated, which measurement was carried out by ELISA using PRRSV-rNp as an antigen.

FIG. 17-1 shows the test schedule for the animal test in "17. Evaluation of Effectiveness of PRRS Liposome Vaccine Using Pigs".

FIG. 17-2 shows changes in the body temperature scores of pigs in the immunization group to which a test vaccine (PRRSV-rNp-DSS) was administered, and pigs in the control group without the vaccine administration.

FIG. 17-3 shows the result of measurement of the amount of viral gene in blood of pigs in the immunization group to which a test vaccine (PRRSV-rNp-DSS) was administered, and pigs in the control group without the vaccine administration.

FIG. 17-4 shows the result obtained by preparing peripheral blood mononuclear cells (PBMCs) from blood of pigs in the immunization group to which a test vaccine (PRRSV-rNp-DSS) was administered, and pigs in the control group without the vaccine administration, and then subjecting the cells to antigen stimulation, followed by measuring the antigen-specific IFN-γ production-inducing ability by ELISPOT for detection of porcine IFN-γ.

FIG. 17-5 shows the result obtained by preparing PBMCs from blood of pigs in the immunization group to which a test vaccine (PRRSV-rNp-DSS) was administered, and pigs in the control group without the vaccine administration, and then subjecting the cells to antigen stimulation, followed by detecting porcine IFN-γ by ELISA using a monoclonal antibody against porcine IFN-γ.

FIG. 17-6 shows the lung lesion score of pigs in the immunization group to which a test vaccine (PRRSV-rNp-DSS) was administered, and pigs in the control group without the vaccine administration. Lung collected at 20 dPC was subjected to histopathological examination for scoring of the severity of the lesion.

FIG. 17-7 shows the result obtained by collecting serum from pigs in the immunization group to which a test vaccine (PRRSV-rNp-DSS) was administered, and pigs in the control group without the vaccine administration, and measuring the blood antibody titer by ELISA using PRRSV-rNp as an antigen.

MODE FOR CARRYING OUT THE INVENTION

Figures 1, 3:
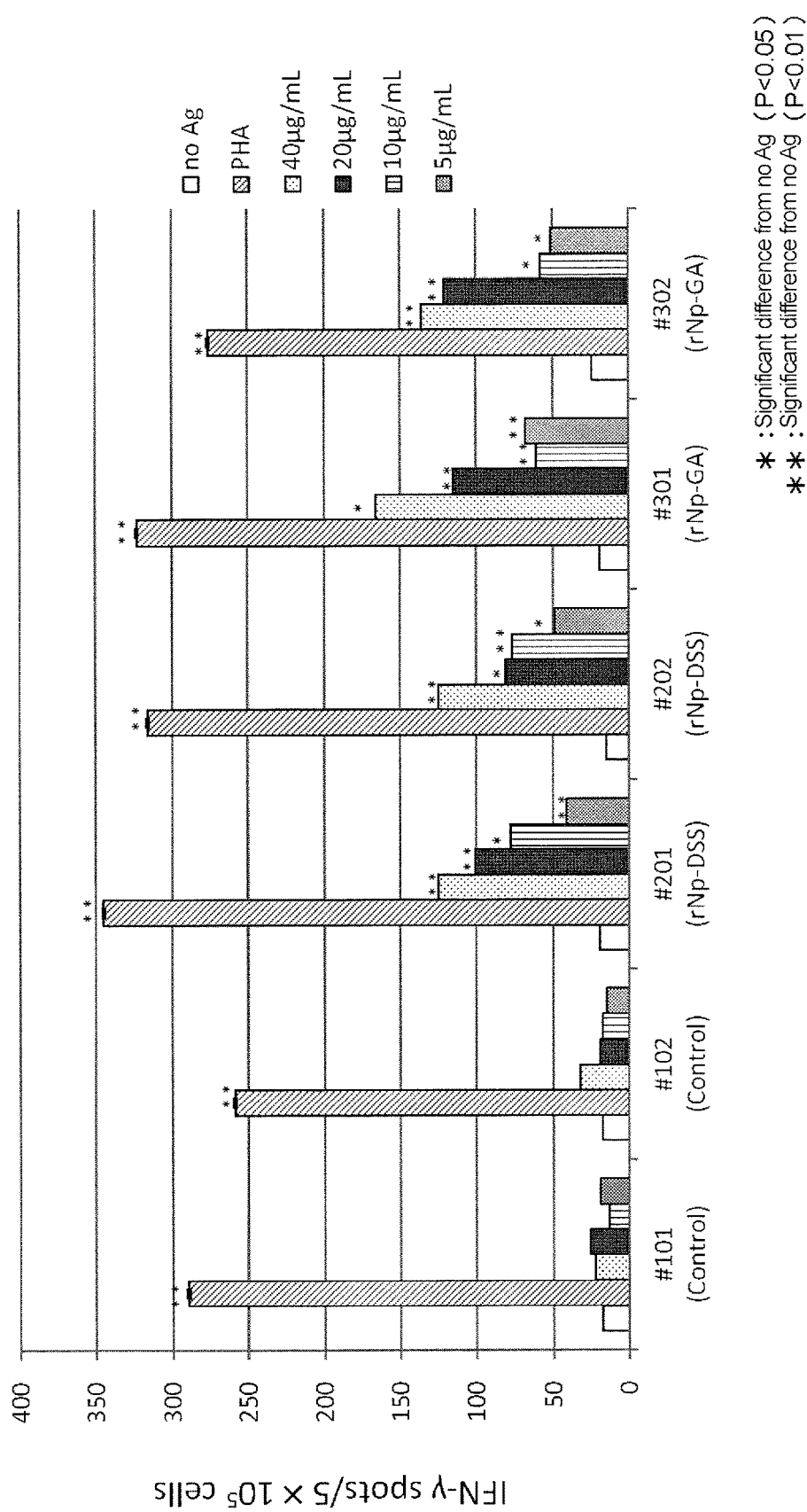

In the present invention, the non-human animals include animals other than human, such as livestock (cows, pigs, horses, sheep, goats, camels, rabbits, and the like), poultry (chickens, ducks, quails, turkeys, ostriches, pheasants, guinea fowls, and the like), and pet animals (dogs, cats, hamsters, guinea pigs, rabbits, ferrets, parakeets, parrots, and the like). The term "birds" includes not only poultry, but also birds not legally included in the group of "poultry" (wild ducks; penguins; pigeons; cormorants; and raptors such as hawks, eagles, falcons, and owls). The terms "poultry" and "birds" include living bodies after hatching, and embryonated eggs. Since livestock and poultry are reared in groups, they are prone to suffer from spreading of infections after occurrence of the infections. Therefore, livestock and poultry can be regarded as non-human animals for which prevention of infections is especially important.

The pathogen is not limited, and includes various pathogens such as fungi, bacteria, viruses, and mycoplasmas.

Specific examples of pathogens that infect livestock or poultry include the following. For all of these examples, information on the genome sequence and the like is known, or isolated strains are available. Thus, antigen molecules such as a recombinant antigen protein that binds to the liposome surface can be appropriately prepared by a conventional method.

<Viruses Infectious to Chickens>
  Infectious bronchitis virus (IBV)
  Avian influenza virus (AIV)
  Newcastle disease virus (NDV)
  Infectious laryngotracheitis virus (ILTV)
  Marek's disease virus (MDV)
  Avian leukemia virus (ALV)
  Infectious bursal disease virus (IBDV)
  Fowlpox virus (FPV)
  Avian encephalomyelitis virus (AEV)
  Chicken adenovirus (FAV)
  Egg drop syndrome—1976 virus (EDS)
  Avian reovirus (ARV)
  Chicken anemia virus (CAV)
  Avian nephritis virus (ANV)
  Reticuloendotheliosis virus (REV)
  Avian metapneumovirus (AMPV)
<Bacteria and Mycoplasmas Infectious to Chickens>
  Mycoplasma gallisepticum (MG)
  Mycoplasma synoviae (MS)
  Salmonella pullorum (SP)
  Salmonella gallinarum (SG)
  Salmonella enleritidis (SE)
  Salmonella typhimurium (ST)
  Salmonella infantis (SI)
  Escherichia coli (E. coli)
  Avibacterium paragallinarum (H. pg)
  Eimeria protozoa
  Leucocytozoon caulleryi
<Viruses Infectious to Pigs>
  Aujeszky's disease virus (ADV)
  Transmissible gastroenteritis virus (TGEV)
  Porcine reproductive and respiratory syndrome virus (PRRSV)
  Porcine epidemic diarrhea virus (PEDV)
  Swine influenza virus (SIV)
  Porcine circovirus type 2 (PCV2)
  Porcine parvovirus (PPV)
  Japanese encephalitis virus (JEV)
  Porcine rotavirus (PRV)
<Bacteria and Mycoplasmas Infectious to Pigs>
  Mycoplasma hyopneumoniae (Mhp)
  Mycoplasma hyopneumoniae (Mhr)
  Salmonella choleraesuis (SC)
  Actinobacillus pleuropneumoniae (App)
  Swine crysipelas (Ery)
  Bordetella bronchiseptica (Bb)
  Pasteurella multocida (Pm)
  Brachyspira hyodysenteriae (Bra-hyo)
  Haemophilus parasuis (Hps)
  Lawsonia intracellularis (Li)
<Viruses Infectious to Cows>
  Akabane disease virus (AKAV)
  Chuzan disease virus (KASV)
  Aino virus (AINOV)
  Ibaraki disease virus (IBAV)
  Bovine viral diarrhea-mucosal disease virus (BVDV)
  Infectious bovine rhinotracheitis virus (IBRV)
  Bovine ephemeral fever virus (BEFV)
  Bovine leukemia virus (BLV)
  Bovine RS virus (BRSV)
  Bovine parainfluenza virus type 3 (BPIV3)
  Bovine adenovirus type 7 (BAV7)
<Bacteria and Mycoplasmas Infectious to Cows>
  Mycoplasma bovis (M. bovis)
  Mycoplasma bovirhinis (M. bovirhinis)
  Mycoplasma bovigenitalium (M. bovigenitalium)
  Mycoplasma disper (M. disper)
  Mycobacterium avium subsp. paraluberculosis (MAP)
  Histophilus somni (Hs)
  Mannheimia haemolytica (Mh)

Typical examples of the antigen molecule derived from a pathogen include proteins encoded by the pathogen genome, and fragments thereof. The antigen molecule in the present invention is preferably a polypeptide. The term "polypeptide" includes proteins encoded by the pathogen genome, and protein fragments composed of partial regions of the proteins. For production of a vaccine effective against pathogens having various antigenicities or genotypes, it is important to employ, as the antigen molecule, a structural protein whose variation is small (whose sequence is highly conserved) among the pathogen strains, or a partial region thereof. Whether such a highly conserved region has immunogenicity or not can be easily confirmed by carrying out an immunity test using an animal such as a mouse. Examples of the method of the immunity test include a method in which an assay such as an ELISPOT assay is carried out to investigate the IFN-γ production-inducing ability of lymphocytes (evaluation of the ability to induce cell-mediated immunity) and a method in which an assay such as ELISA is carried out to investigate the antibody-inducing ability (evaluation of the ability to induce humoral immunity).

In cases where the pathogen is a virus, there are viruses having or not having an envelope. In cases of a virus having an envelope, the envelope is present on the outermost part of the virus particle. Therefore, the frequency at which the nucleocapsid protein undergoes a selection pressure, such as an attack by the immune function in the host body, is extremely low. Thus, in cases of a virus having an envelope, the sequence of the nucleocapsid protein is more conserved among viral strains compared to the sequences of other structural proteins. Thus, for preparation of a vaccine of the present invention against a virus having an envelope, the nucleocapsid protein may be preferably employed as the antigen molecule. Among the pathogens exemplified above, IBV, PRRSV, AIV, NDV, ILTV, MDV, ALV, FPV, REV, AMPV, ADV, TGEV, PEDV, SIV, JEV, AKAV, AINOV, BVDV, IBRV, BEFV, BLV, BRSV, and BPIV3 correspond to viruses having an envelope.

The polypeptide may be a recombinant peptide prepared by a genetic recombination technique, or may be a polypeptide prepared by chemical synthesis. In cases where the polypeptide is a short polypeptide having not more than about several ten residues, the chemical synthesis can also be easily carried out. Both the genetic recombination technique and the chemical synthesis of polypeptide are well-known conventional methods.

In the preparation of a recombinant polypeptide by the genetic recombination technique, a polynucleotide encoding a desired antigen polypeptide may be prepared, and the polynucleotide may be cloned into an appropriate vector, followed by introducing the vector into an appropriate host cell, allowing expression of the polypeptide in the host cell, and then recovering and purifying the polypeptide. In cases where the pathogen is a bacterium or *Mycoplasma*, RT-PCR may be carried out using total RNA extracted from pathogen cells as a template, and using appropriate primers, to prepare a cDNA encoding a desired antigen polypeptide region. In cases where the pathogen is a virus, total RNA may be extracted from cells infected with the virus, and RT-PCR may be carried out using the total RNA as a template. Various cloning vectors and host cells are known, and there are also commercially available products thereof. An appropriate vector and host cells may be selected therefrom in accordance with, for example, properties of the antigen polypeptide to be prepared. For convenience in the recovery and purification of the polypeptide expressed in the host cells, the antigen polypeptide may be expressed with an appropriate tag such as a His tag attached thereto.

Specific examples of the chemical synthesis method include the Fmoc method (fluorenylmethyloxycarbonyl method) and the tBoc method (t-butyloxycarbonyl method). The synthesis may also be carried out by an ordinary method using a commercially available peptide synthesizer. In cases of the chemical synthesis, a desired polypeptide may be synthesized based on the amino acid sequence alone.

As examples of a most preferred vaccine according to the present invention, the later-mentioned Examples describe specific examples of liposome vaccines having an antigen bound to the surface thereof to be used for poultry against IBV. For the IBV liposome vaccines according to the present invention, nucleocapsid protein (N protein) may be preferably used as the antigen molecule. As the N protein of IBV, full-length N protein is preferably used rather than a fragment thereof. N protein is a region having fewer mutations among isolated IBV strains. In particular, N protein having the amino acid sequence of SEQ ID NO:2 may be most preferably used as the antigen molecule for the IBV liposome vaccines. Polypeptides having the same amino acid sequence as SEQ ID NO:2 except that a very small number of amino acids, such as about one or several amino acids, for example, one to five, one to four, one to three, one or two, or one amino acid(s) is/are substituted, deleted, inserted, and/or added (in terms of the sequence identity, polypeptides having an amino acid sequence having an identity of not less than 98% to the amino acid sequence of SEQ ID NO:2) can also be expected to have high immunogenicities similarly to N protein having the amino acid sequence of SEQ ID NO:2, and may therefore be similarly preferably used. One preferred mode of the substitution may be a conservative substitution. Substitution to an amino acid having similar chemical properties is called conservative substitution. It is a substitution which does not deteriorate the properties of the protein. Amino acids having similar side chains have similar chemical properties. Based on the similarities among the side chains, amino acids can be grouped into, for example, a group of amino acids having an aliphatic side chain (glycine, alanine, valine, leucine, isoleucine, and proline), a group of amino acids having an aliphatic hydroxyl side chain (serine and threonine), a group of amino acids having an amide-containing side chain (asparagine and glutamine), a group of amino acids having an aromatic side chain (phenylalanine, tyrosine, and tryptophan), a group of amino acids having a basic side chain (arginine, lysine, and histidine), a group of amino acids having an acidic side chain (aspartic acid and glutamic acid), and a group of amino acids having a sulfur-containing side chain (cysteine and methionine). Examples of the conservative substitution include substitutions within each of these groups.

As other examples of a most preferred vaccine according to the present invention, the later-mentioned Examples also describe specific examples of liposome vaccines having an antigen bound to the surface thereof, to be used for pigs against PRRSV. Also for the PRRSV liposome vaccines, nucleocapsid protein (N protein) may be preferably used as the antigen molecule. Full-length N protein may be preferably used also as the N protein of PRRSV. Alternatively, a fragment(s) of one or more partial regions having high immunogenicities may be used as the antigen molecule. The amino acid sequence of N protein of PRRSV, and the base sequence of the ORF7 region encoding this amino acid sequence, can be obtained from databases such as GenBank in NCBI. The amino acid sequence of SEQ ID NO:28 is one example of the amino acid sequence of N protein of PRRSV. In addition to the protein having this amino acid sequence, polypeptides having the same amino acid sequence as SEQ ID NO: 28 except that a very small number of amino acids, such as about one or several amino acids, for example, one to five, one to four, one to three, one or two, or one amino acid(s) is/are substituted (by, for example, the conservative substitution described above), deleted, inserted, and/or added (in terms of the sequence identity, polypeptides having an amino acid sequence having an identity of not less than 93%, for example, not less than 95%, or not less than 98% to the amino acid sequence of SEQ ID NO:28) can also be expected to have high immunogenicities similarly to the N protein having the amino acid sequence of SEQ ID NO:28, and may therefore be similarly preferably used.

The "sequence identity" means the value calculated by aligning two amino acid sequences to be compared such that the number of matched amino acid residues becomes largest between the amino acid sequences, and dividing the number of matched amino acid residues by the total number of amino acid residues, which value is expressed as a percentage. In the alignment, a gap(s) is/are inserted, when necessary, into one or both of the two sequences to be compared. Such alignment of sequences may be carried out using a well-known program such as BLAST, FASTA, or CLUSTAL W. When a gap(s) is/are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The constitution and the preparation method of the liposome vaccine of the present invention are concretely described below using, as an example, an IBV liposome vaccine, which is one most preferred example of the vaccine according to the present invention. However, the following constitution and method are not limited to those for vaccines against IBV. For example, liposome vaccines against the pathogens of livestock or poultry exemplified above may also be prepared as appropriate according to the following. In the Examples described below, preparation of PRRSV liposome vaccines by the same method as the method for IBV liposome vaccines is described.

The phospholipid membrane constituting the liposome portion of the vaccine according to the present invention contains the following components (A) and (B). In the present description, mol % of each component of the phospholipid membrane means mol % with respect to the total constituents of the phospholipid membrane constituting the liposome portion.

(A) A phospholipid containing: a $C_{14}$-$C_{24}$ acyl group having one unsaturated bond; or a $C_{14}$-$C_{24}$ hydrocarbon group having one unsaturated bond (hereinafter, the acyl group may be referred to as "unsaturated acyl group", and the hydrocarbon group may be referred to as "unsaturated hydrocarbon group").

(B) A stabilizer for a liposome.

The content of the component (A) is 1 to 99.8 mol %. From the viewpoint of stability of the liposome, the content is preferably 10 to 90 mol %, more preferably 30 to 80 mol %, still more preferably 50 to 70 mol %. The number of carbon atoms of the acyl group or the hydrocarbon group is preferably 16 to 22, more preferably 18 to 22 or 16 to 20, most preferably 18.

The phospholipid may be a glycerophospholipid having a glycerin backbone, or may be a sphingophospholipid having a sphingosine backbone. In the present invention, a glycerophospholipid may be more preferably used.

In cases where the phospholipid is a glycerophospholipid, the unsaturated acyl group(s) and/or unsaturated hydrocarbon group(s) bound to the 1-position and the 2-position of the glycerin backbone may be either the same or different. From the viewpoint of industrial productivity, the 1-position and the 2-position preferably have the same group.

Specific examples of the unsaturated acyl group include palmitoleoyl, oleoyl, and erucoyl. Specific examples of the unsaturated hydrocarbon group include tetradecenyl, hexadecenyl, octadecenyl, $C_{20}$ monoene, $C_{22}$ monoene, and $C_{24}$ monoene.

The phospholipid of the component (A) preferably contains an unsaturated acyl group. An especially preferred phospholipid of the component (A) is a phospholipid containing a $C_{18}$ acyl group having one unsaturated bond, that is, an oleoyl group.

The component (A) may include a plurality of different phospholipids which are in accordance with the definition of the phospholipid of (A) described above. Specific examples of the phospholipids include acidic phospholipids and neutral phospholipids; and reactive phospholipids containing a functional group to which an antigen molecule can be bound. The component (A) may include two or more, or three or more of these. In cases where the component (A) includes a plurality of different phospholipids, the unsaturated acyl group(s) and/or unsaturated hydrocarbon group(s) contained in these phospholipids may be totally the same, or may be different among the phospholipids. Usually, the plurality of different phospholipids preferably have the same unsaturated acyl group or unsaturated hydrocarbon group.

The liposome portion of the liposome vaccine of the present invention may contain, in addition to the phospholipid defined in (A), another phospholipid not included in this definition, or a lipid other than a phospholipid. The phospholipid of (A) may be contained at not less than 50%, preferably not less than 60%, more preferably not less than 75%, still more preferably not less than 90%, most preferably not less than 95%, for example, not less than 97%, in the phospholipid membrane component of the liposome portion. The content of the other lipid(s) not included in the definition of (A) is usually not more than 40 mol %, preferably not more than 20 mol %, more preferably not more than 10 mol %, still more preferably not more than 5 mol %.

The type and the ratio of each phospholipid used as the component (A) may be appropriately selected in accordance with various requirements and purposes. The phospholipid is generally used at the following content.

The content of the neutral phospholipid(s) is usually 0.01 to 80 mol %, preferably 0.1 to 70 mol %, more preferably 0.1 to 60 mol %, still more preferably 0.1 to 50 mol %.

The content of the acidic phospholipid(s) is usually 1 to 85 mol %, preferably 2 to 80 mol %, more preferably 4 to 60 mol %, still more preferably 5 to 40 mol %.

The content of the reactive phospholipid(s) is usually 0.2 to 80 mol %, preferably 0.3 to 60 mol %, more preferably 0.4 to 50 mol %, still more preferably 0.5 to 25 mol %.

As the acidic phospholipid(s), diacylphosphatidylserine, diacylphosphatidylglycerol, diacylphosphatidic acid, diacylphosphatidylinositol, and/or the like containing the acyl group defined in (A) may be preferably used. Since an acidic phospholipid gives anionic ionized groups to the surface of the liposome, it imparts a negative zeta potential to the surface of the liposome. By this, the liposome acquires a charge-based repulsive force, and can be present as a stable preparation in an aqueous solvent. Thus, an acidic phospholipid is a component that plays an important role in securing stability of the antigen-bound liposome in an aqueous solvent.

As the neutral phospholipid(s), phosphatidylcholine and/or the like containing the acyl group defined in (A) may be preferably used. A neutral phospholipid has a higher liposome-stabilizing function than an acidic phospholipid, or a reactive phospholipid to which an antigen molecule is bound. A neutral phospholipid is therefore capable of improving the stability of the membrane. From such a point of view, the phospholipid membrane constituting the liposome portion of the liposome vaccine of the present invention preferably contains a neutral phospholipid.

As described above, the reactive phospholipid is a phospholipid containing a functional group to which an antigen molecule can be bound. Representative examples of the functional group include an amino group. The reactive phospholipid may have a terminal structure to which an antigen molecule can be bound (reactive terminal structure), which terminal structure was introduced by binding a crosslinking agent or the like to the phospholipid. The term "functional group" herein includes such a terminal structure introduced to the phospholipid molecule. For example, the functional group includes the aldehyde group, succinimide group, maleimide group, and the like contained in the divalent reactive compounds exemplified below.

Specific examples of a reactive phospholipid which may be preferably used include phosphatidylethanolamines, and modified phosphatidylethanolamines prepared by introducing a reactive terminal structure to a phosphatidylethanolamine, which phosphatidylethanolamines contain the acyl group defined in (A).

Examples of the modified phosphatidylethanolamines include modified diacylphosphatidylethanolamines prepared by binding one end of a divalent reactive compound to the amino group of a diacylphosphatidylethanolamine. As the divalent reactive compound, compounds known as cross-linking agents may be used. For example, for a diacylphosphatidylethanolamine, a compound containing at least one end an aldehyde group or succinimide group reactive with an amino group may be used.

Examples of the divalent reactive compound containing an aldehyde group include glyoxal, glutaraldehyde, succinaldehyde, and terephthalaldehyde. Glutaraldehyde may be especially preferably used. As described later, the introduction of an aldehyde group with glutaraldehyde or the like to the functional group (amino group) of the reactive phospholipid is usually carried out after the preparation of the liposome.

Examples of the divalent reactive compound containing a succinimide group include dithiobis(succinimidyl propionate), ethylene glycol-bis(succinimidyl succinate), disuccinimidyl succinate, disuccinimidyl suberate, and disuccinimidyl glutarate. Disuccinimidyl suberate may be especially preferably used.

Examples of a divalent reactive compound having a succinimide group at one end, and a maleimide group at the other end, include N-succinimidyl-4-(p-maleimidophenyl) butyrate, sulfosuccinimidyl-4-(p-maleimidophenyl)butyrate. N-succinimidyl-4-(p-maleimidophenyl)acetate, N-succinimidyl-4-(p-maleimidophenyl)propionate, succinimidyl-4-(N-maleimidoethyl)-cyclohexane-1-carboxylate, sulfosuccinimidyl-4-(N-maleimidoethyl)-cyclohexane-1-carboxylate, N-(γ-maleimidobutyryloxy)succinimide, and N-(ε-maleimidocaprovloxy)succinimide. By use of such a divalent reactive compound, a modified diacylphosphatidylethanolamine containing a maleimide group as a functional group can be obtained.

Specific examples of the modified diacylphosphatidylethanolamine having a divalent reactive compound bound thereto include succinimidyl-diacylphosphatidylethanolamine and maleimide-diacylphosphatidylethanolamine.

The content of the component (B) is 0.2 to 75 mol %. From the viewpoint of stability of the liposome, the content is preferably 5 to 70 mol %, more preferably 10 to 60 mol %, still more preferably 20 to 50 mol %. In cases where the content of the stabilizer exceeds 75 mol %, stability of the liposome is deteriorated, which is not preferred.

As the stabilizer for the liposome, a sterol or tocopherol may be used. The sterol is not limited as long as it is generally known as a sterol, and examples of the sterol include cholesterol, sitosterol, campesterol, stigmasterol, and brassicasterol. From the viewpoint of availability and the like, cholesterol may be especially preferably used. The tocopherol is not limited as long as it is generally known as a tocopherol. For example, from the viewpoint of availability and the like, a commercially available α-tocopherol may be preferably used.

The IBV-derived polypeptide such as N protein to be used as the antigen polypeptide molecule may be bound by using the functional group of the reactive phospholipid in the liposome. By covalently binding the antigen polypeptide molecule to the functional group of the reactive phospholipid which is one component of the phospholipid membrane, the antigen polypeptide molecule can be stably bound to the liposome surface. Such a technique per se is known, and described in, for example, Non-Patent Document 1 and Patent Documents 1 to 3. Although the antigen polypeptide molecule can also be bound to the liposome surface by ionic bonding or hydrophobic bonding as described in Patent Documents 2 and 3, in the IBV liposome vaccine according to the present invention the IBV-derived polypeptide is more preferably bound to the liposome surface by covalent bonding, from the viewpoint of the binding stability during storage and in the living body.

In the preparation of the IBV liposome vaccine, the binding reaction between the liposomes and the IBV-derived polypeptide may be carried out after the preparation of the liposomes containing the reactive phospholipid.

The preparation per se of the liposomes may be carried out according to a conventional method. Examples of the production method include the extrusion method, vortex mixer method, ultrasonic method, surfactant removal method, reverse-phase evaporation method, ethanol injection method, pre-vesicle method, French press method, W/O/W emulsion method, annealing method, and freeze-thaw method. The shape of the liposome is not limited. By appropriately selecting a known liposome production method described above, liposomes having various sizes and shapes, such as a multilamellar liposome, small unilamellar liposome, or large unilamellar liposome can be produced.

The particle size of the liposomes is not limited. From the viewpoint of storage stability and the like, the average particle size of the liposomes is preferably 20 to 600 nm, more preferably, for example, 30 to 500 nm, 40 to 400 nm, 50 to 300 nm, or 70 to 230 nm. The average particle size of the liposomes can be measured by the well-known dynamic light scattering method.

In the present invention, during or alter the preparation of the liposomes, a saccharide or polyol may be added to at least one of the internal aqueous phase and external aqueous phase of the liposomes. By this, the physicochemical stability of the liposomes can be further increased. For example, a liposome suspension containing the reactive phospholipid and the liposome stabilizer may be prepared in a buffer containing a saccharide or polyol, or a liposome suspension containing the reactive phospholipid and the liposome stabilizer may be prepared followed by adding and dissolving a saccharide such as saccharose, or a polyol, in the external aqueous phase of the liposome suspension. Subsequently, the liposome suspension containing the saccharide or polyol may be transferred to a 10-mL glass vial, and then freeze-dried to obtain a freeze-dried product of liposomes each containing a functional group(s) for binding the antigen polypeptide molecule to the surface. By providing the liposomes as the freeze-dried product, it can be stably stored for a long period as an intermediate material for preparation of the liposome vaccine of the present invention.

Examples of the saccharide include monosaccharides such as glucose, galactose, mannose, fructose, inositol, ribose, and xylose; disaccharides such as saccharose, lactose, cellobiose, trehalose, and maltose; trisaccharides such as raffinose and melezitose; oligosaccharides such as cyclodextrin; polysaccharides such as dextrin; and sugar alcohols such as xylitol, sorbitol, mannitol, and maltitol. Among these saccharides, monosaccharides and disaccharides are preferred. In particular, from the viewpoint of availability and the like, glucose or saccharose may be especially preferably used.

Examples of the polyol include glycerin compounds such as glycerin, diglycerin, triglycerin, tetraglycerin, pentaglycerin, hexaglycerin, heptaglycerin, octaglycerin, nonaglycerin, decaglycerin, and polyglycerin; sugar alcohol compounds such as sorbitol and mannitol; ethylene glycol; diethylene glycol; triethylene glycol; tetraethylene glycol; pentaethylene glycol; hexaethylene glycol; heptaethylene glycol; octaethylene glycol; and nonaethylene glycol. Among these, from the viewpoint of availability, glycerin, diglycerin, triglycerin, sorbitol, or mannitol; or a polyethylene glycol having a molecular weight of 400 to 10,000; may be especially preferably used.

The concentration of the saccharide or polyol contained in at least one of the internal aqueous phase and external aqueous phase of the liposomes may be about 1 to 20% by weight, for example, about 2 to 10% by weight, in terms of the weight concentration with respect to the liposome liquid.

Examples of the functional group of the antigen polypeptide molecule that can be used for the covalent bonding to the liposome surface include an amino group, thiol group, carboxy group, hydroxyl group, and disulfide group. Examples of the combination of functional groups preferred for the covalent bonding include: an amino group and an aldehyde group or carboxy group; an amino group and an amino group; an amino group and a succinimide group; and a thiol group and a maleimide group. Specific examples of the covalent bond between the functional group of the reactive phospholipid and the antigen polypeptide molecule include a Schiff base bond, an amide bond, a thioether bond, and an ester bond.

In cases where the functional group is imparted to the reactive phospholipid by binding of a divalent reactive compound thereto, one of the following methods may be selected depending on the type of the divalent reactive compound: (Method 1) an amino group or the like of the reactive phospholipid is bound to the divalent reactive compound before the preparation of liposomes, and then the reactive phospholipid in which the divalent reactive compound is introduced is used to prepare the liposomes; or (Method 2) liposomes containing the reactive phospholipid are prepared, and then the divalent reactive compound is introduced to an amino group or the like of the reactive phospholipid in the phospholipid membrane. Representative examples of a divalent reactive compound for which Method 1 is employed include disuccinimidyl suberate. Representative examples of a divalent reactive compound for which Method 2 is employed include glutaraldehyde. Both methods per se are known, and described in, for example, Patent Documents 2 and 3, and Non-Patent Documents 2 and 3.

The process of each method is described for the cases of disuccinimidyl suberate (DDS) and glutaraldehyde.

In Method 1, first, disuccinimidyl suberate is bound to the functional group of the reactive phospholipid. As the reactive phospholipid, among the phospholipids defined in (A), a phospholipid containing an amino group as the functional group, such as diacylphosphatidylethanolamine may be preferably used. The binding between the amino group and the disuccinimidyl suberate may be carried out by a known method described in Patent Document 2 or 3, Non-Patent Document 2, or the like, or may be carried out as concretely described below in Examples. By such a method, a reactive phospholipid containing a suberic acid succinimide group ($-CO-(CH_2)_6-COO-C_4H_4NO_2$) introduced to the amino group can be obtained. The reactive phospholipid containing a succinimide group as the functional group includes such a reactive phospholipid containing a suberic acid succinimide group introduced therein. As used in the present description, the term "disuccinimidyl suberate (DDS)-bound diacylphosphatidylethanolamine" means diacylphosphatidylethanolamine containing a suberic acid succinimide group introduced to the amino group.

Subsequently, the reactive phospholipid containing the suberic acid succinimide group introduced therein is mixed with other liposome constituents (that is, other phospholipids corresponding to the component (A), such as an acidic phospholipid and a neutral phospholipid; the liposome stabilizer of the component (B); and, when necessary, other lipids and the like) by a known method, to prepare liposomes. By preparation according to a conventional method, liposomes each containing a succinimide group(s) on its surface, which succinimide group is the functional group introduced to the reactive phospholipid, can be obtained.

To the suspension of the liposomes prepared, an IBV-derived polypeptide is added, and the amino group in the polypeptide is reacted with the succinimide group on the liposome surface.

Unreacted IBV-derived polypeptide, reaction by-products, and the like are removed by a known method such as gel filtration, dialysis, ultrafiltration, or centrifugation. By this, liposomes each comprising the IBV-derived polypeptide molecule(s) covalently bound to its surface through a suberic acid cross-link can be obtained.

In Method 2, liposomes each having on its surface an amino group(s) to be bound to the aldehyde group of glutaraldehyde are prepared. As the reactive phospholipid, a phospholipid containing an amino group as the functional group, such as diacylphosphatidylethanolamine may be used. The reactive phospholipid containing an amino group is mixed with other liposome constituents (that is, other phospholipids corresponding to the component (A), such as an acidic phospholipid and a neutral phospholipid; the liposome stabilizer of the component (B); and, when necessary, other lipids and the like) by a known method, to prepare liposomes. By preparation according to a conventional method, liposomes each having the amino group(s) contained in the reactive phospholipid molecule(s) is/are present on its surface can be obtained.

Subsequently, the liposome suspension is mixed with an IBV-derived polypeptide, and glutaraldehyde is then added to the resulting mixture, followed by allowing the reaction to proceed for a predetermined length of time to form a Schiff base bond between the liposomes and the polypeptide.

Subsequently, a water-soluble compound containing an amino acid group such as glycine is added to the liposome suspension, to deactivate the reactivity of the excess glutaraldehyde.

Unnecessary components such as unreacted IBV-derived polypeptide, reaction product between glutaraldehyde and glycine, and excessive glycine are removed by a known method such as gel filtration, dialysis, ultrafiltration, or centrifugation. By this, liposomes each comprising the IBV-derived polypeptide molecule(s) covalently bound to its surface through a glutaraldehyde cross-link can be obtained.

In the IBV liposome vaccine according to the present invention, the covalent bond between the IBV-derived polypeptide and the liposome is not limited. It has been found that a liposome vaccine obtained by binding through a suberic acid cross-link tends to have a higher vaccine effect than a liposome vaccine obtained by binding through a glutaraldehyde cross-link (see the later-described Examples).

In cases where an IBV liposome vaccine is prepared by Method 1 (a method in which a divalent reactive compound is preliminarily introduced to a reactive phospholipid, and then the resulting product is mixed with other lipids, to prepare liposomes), the components of the liposome portion especially preferably have the following composition (molar ratios): neutral phospholipid, about 2 to 12, preferably about 4 to 8; acidic phospholipid, about 0.5 to 4, preferably about 1 to 3; stabilizer, about 2 to 14, preferably about 5 to 10; with respect to the reactive phospholipid whose ratio is regarded as 1. The reactive phospholipid herein means the total reactive phospholipid, including reactive phospholipids to which the antigen molecule is bound and reactive phospholipids to which no antigen molecule is bound.

In cases where an IBV liposome vaccine is prepared by Method 2 (a method in which liposomes are prepared, and then a divalent reactive compound is introduced thereto), the components of the liposome portion especially preferably have the following composition (molar ratios): neutral phospholipid, about 0.5 to 3, preferably about 1 to 2; acidic phospholipid, about 0.1 to 2, preferably about 0.3 to 1; stabilizer, about 1 to 4, preferably about 1.5 to 3; with respect to the reactive phospholipid whose ratio is regarded as 1. The reactive phospholipid herein also means the total reactive phospholipid, including reactive phospholipids to which the antigen molecule is bound and reactive phospholipids to which no antigen molecule is bound.

Especially preferred examples of the composition of the liposome portion of the IBV liposome vaccine include those containing the following reactive phospholipid, neutral phospholipid, acidic phospholipid, and liposome stabilizer at any molar ratios described above.

Reactive phospholipid: dioleoylphosphatidylethanolamine (DOPE)
Neutral phospholipid: dioleoylphosphatidylcholine (DOPC)
Acidic phospholipid: dioleoylphosphatidylglycerol (DOPG)
Liposome stabilizer: cholesterol The liposomes each comprising an IBV-derived antigen molecule(s) bound to the surface thereof may be formulated as a vaccine by mixing, as appropriate, with a pharmaceutically acceptable additive such as a carrier, diluent, or excipient suitable for the administration route employed. For example, the liposomes may be provided as a liquid formulation containing the liposomes suspended therein, and the liquid formulation may be orally or parenterally administered to a non-human animal whose symptoms caused by infection with a pathogen are to be reduced, for example, a bird (especially chicken) whose symptoms of IB caused by infection with IBV are to be reduced, or livestock (more specifically, a pig) whose symptoms of PRRS caused by infection with PRRSV are to be reduced. As long as the immunity-inducing ability of the antigen molecule is not deteriorated, the antigen-bound liposomes may be subjected to freeze-drying or vacuum drying for preparation of a liposome powder formulation.

Specific examples of the administration route for the parenteral administration include intravenous administration, subcutaneous administration, intradermal administration, intramuscular administration, transnasal administration, transdermal administration, rectal administration, intratracheal administration, and ocular instillation administration, and, in cases of administration to a bird, in ovo administration. Specific examples of the dosage form include orally administered agents such as solutions and capsules; and parenteral administration agents such as injection solutions (for example, intramuscular injection agents and in ovo administration agents), fine spray agents, coarse spray agents, nasal drops, eye drops, and suppositories. Preferred examples of the administration method or dosage form of the liposome vaccine according to the present invention include fine spray administration (agents), coarse spray administration (agents), nasal instillation administration (agents), ocular instillation administration (agents), intramuscular administration (agents), subcutaneous administration (agents), intradermal administration (agents), and inhalation administration (agents). Other preferred examples of the administration method or dosage form include in ovo administration (agents) in cases of administration to a bird. The IBV liposome vaccine of the present invention has been found to be effective also for 0-day-old newborn chicks, whose development of the immune system is immature. Thus, the vaccine is thought to be capable of sufficiently inducing immunity against IBV also by in ovo administration. In the present invention, the fine spray administration agent is an agent administered by spraying at a droplet particle size of not more than 150 μm, and the coarse spray administration agent is an agent administered by spraying at a droplet particle size of not less than 200 μm. The inhalation administration agent is an agent generally administered by inhalation at a droplet particle size of about 100 μm to about several ten micrometers or less (however, the droplet particle size is not limited thereto, and may be appropriately set). In the present invention, the spray administration is mainly a method in which a plurality of animal individuals are treated with an agent at once. In this administration method, an agent liquid in the form of a mist is sprayed to the heads or whole bodies of the plurality of individuals, to make the individuals inhale the agent. The inhalation administration is an administration method in which an agent liquid in the form of a mist is sprayed to a respiratory organ (the nose or mouth) of one individual in a focused manner, to make the individual inhale the agent. The spray administration is an administration method suitable for relatively small animals such as poultry or poultry chicks, including chickens. The inhalation administration is an administration method suitable for relatively large animals such as pigs and cows.

In particular, the dosage form or administration method of the IBV liposome vaccine according to the present invention is especially preferably a fine spray agent (fine spray administration), and the administration route is especially preferably transnasal administration or intratracheal administration. As described below in the Examples, the IBV liposome vaccine may be administered by spray administration (fine spray administration) at a reduced droplet particle size, to enhance the effect of the vaccine. Thus, the administration method for the IBV liposome vaccine of the present invention is especially preferably fine spray administration, and the fine spray administration is carried out with a droplet particle size of preferably not more than 120 m, more preferably not more than 100 μm, for example, 50 μm to 100 μm. The droplet particle size can be easily controlled using a known fine spray administration apparatus. The dosage form and administration route of the PRRSV liposome vaccine according to the present invention are especially preferably an intramuscular administration agent and intramuscular administration.

The dose of the IBV liposome vaccine of the present invention is not limited as long as it is an amount effective for prevention of IBV infection or for reduction of symptoms of IB caused by IBV infection. The effective amount is appropriately selected depending on the body weight, age, and the like of the non-human animal (more specifically, poultry, especially chicken) to which the vaccine is to be administered. The vaccine may be, but does not necessarily need to be, administered at a dose of about 0.03125 to 2 µg, for example, about 0.25 to 1 µg, per administration in terms of the amount of the IBV-derived polypeptide. The term "symptoms of IB" includes not only respiratory symptoms as the cardinal symptoms, but also various symptoms known as symptoms of IB, such as nephritis, egg-laying disorders (for example, a decreased egg-laying rate, and production of malformed eggs), and diarrhea.

The same applies to the doses of vaccines against pathogens other than IBV. For example, the dose of the PRRSV liposome vaccine is not limited as long as it is an amount effective for prevention of PRRSV infection or for reduction of symptoms of PRRS caused by PRRSV infection. The effective amount is appropriately selected depending on the body weight, age, and the like of the pig to which the vaccine is to be administered. The vaccine may be, but does not necessarily need to be, administered at a dose of about 0.1 to 500 µg, for example, about 10 to 200 µg, per administration in terms of the amount of the PRRSV-derived polypeptide. The term "symptoms of PRRS" includes various symptoms known as symptoms of PRRS, such as respiratory symptoms including cough and dyspnea; reproductive disorders including abortion or stillbirth in mother pigs; weakness; anorexia; eyelid edema; and a decreased rate of weight gain.

The amount of antigen polypeptide molecules bound to the liposome surface may be measured by an ordinary method utilizing the BCA method. More specifically, the amount of the antigen polypeptide on the liposome surface may be measured using a Pierce (trade name) BCA Protein Assay Kit—Reducing Agent Compatible (Thermo Fisher Scientific Inc.), and using the prepared antigen polypeptide-bound liposomes as a measurement sample, according to the manufacturer's instructions for the kit.

The frequency of administration of the IBV liposome vaccine is not limited. Although a certain degree of effect can be obtained even by single administration, the administration is preferably carried out two or more times in order to obtain a high effect to reduce the symptom onset against IBV. The administration may be carried out, for example, two to live times, two to four times, or two or three times. However, there is no upper limit of the number of doses, and, when necessary, six or more times of administration may be carried out for a single individual. For efficient immune induction, the dosing interval of the vaccine is preferably at least 1 week. For example, the vaccine is preferably administered a plurality of times at dosing intervals of not less than 10 days, preferably not less than 2 weeks.

The number of doses of the PRRSV liposome vaccine is also not limited. The vaccine may be administered one or more times, but, for obtaining a high effect against PRRSV, the vaccine is preferably administered two or more times. The administration may be carried out, for example, two to five times, two to four times, or two or three times. However, there is no upper limit of the number of doses, and, when necessary, six or more times of administration may be carried out for a single individual. For efficient immune induction, the dosing interval of the vaccine is preferably at least 1 week. For example, the vaccine is preferably administered a plurality of times at dosing intervals of not less than 10 days, preferably not less than 2 weeks.

The timing of administration of the IBV liposome vaccine is not limited, and the vaccine may be administered at any age in days. For example, from the viewpoint of effectively preventing spreading of IB in a population, the IBV liposome vaccine of the present invention is preferably administered at least once during a period in an early stage after hatching (about 0 day old to about 21 days old). For example, the vaccine may be administered once during the period from 0 day old to 14 days old (especially at 0 day old), and then, after the appropriate dosing interval described above, the second administration may be carried out. Further, when necessary, the third and/or later administrations may be carried out. In cases of in ovo inoculation, the vaccine may be inoculated at least once during the period from about 17 to 20 days old, for example, from 18 to 19 days old, in terms of the incubation age in days, although the timing is not limited. It is usually preferred to carry out in ovo inoculation once, and then to carry out one or more times of inoculation after hatching. Further, for example, for the purpose of suppressing egg-laying disorders due to IB caused by IBV infection, the vaccine may be administered to a mature female bird (in cases of a chicken, an egg-laying chicken at not less than 120 days old) at least once, preferably two or more times at the appropriate dosing intervals described above.

The timing of administration of the PRRSV liposome vaccine is also not limited, and the vaccine may be administered at any age in days or weeks. For example, the vaccine may be administered at least once during the period from 2 weeks old to 10 weeks old. In addition to the administration to a young pig, at least one time of administration may be carried out for a female pig several weeks (for example, 3 to 4 weeks) before mating, for reduction of reproductive disorders and improvement of the reproductive performance of the female pig.

The number of doses and the timing of administration of a liposome vaccine against a pathogen other than IBV and PRRSV are also not limited, and may be appropriately set depending on the type of the pathogen, the type and age of the subject animal, and the like.

Examples

The present invention is described below more concretely by way of Examples. However, the present invention is not limited to the following Examples.

1. Preparation of Recombinant Antigens
<Object>

For preparation of liposome vaccines against infectious bronchitis virus (hereinafter referred to as IBV), full-length nucleocapsid protein (N protein) and full-length membrane (M) protein, which are relatively highly conserved among IBV strains, were prepared as antigens for the vaccines, using recombinant *E. coli*.

<Materials and Methods>
(1) Search for Antigen Regions

Since N protein and M protein of IBV have been reported to be relatively highly conserved, these proteins were used as antigen candidate regions. For 11 IBV strains that were recently isolated in Japan, homologies were evaluated by sequence analysis, to select the IBV to be used as the antigen template.

The search for the antigen regions was carried out using the following primers.

```
N protein Fw:
                              (SEQ ID NO: 15)
GCGTGTACCTCTCTAGTAT N protein Rv:
                              (SEQ ID NO: 16)
GCTACATGCCTATCTBCCTTA(B = G/T/C)

M protein Fw:
                              (SEQ ID NO: 17)
GGTAGAAAACTTAACAATCC M protein Rv:
                              (SEQ ID NO: 18)
AAGACTACTTCCTCCTGTTG
```

(2) Preparation of Recombinant Proteins by *E. coli* Expression System

Each full-length antigen region determined in (1) was amplified by the RT-PCR method, and then inserted into a vector (N-terminal His-tag labeling plasmid). The resulting plasmid was introduced into *E. coli* for cloning, to transform the *E. coli*. Subsequently, plasmid was extracted from *E. coli* in which the insertion of the target gene could be confirmed by PCR, and the extracted plasmid was introduced into *E. coli* for protein expression, to transform the *E. coli*. Subsequently, the *E. coli* for expression was cultured, and IPTG was added thereto for induction of expression, to allow expression of a recombinant protein. The bacterial cells were disrupted by sonication, and affinity purification using a His tag was carried out. For the solution after the purification, the total protein concentration was measured. SDS-PAGE was carried out to confirm that the expressed protein is found at the position corresponding to the assumed molecular weight.

The RT-PCR, and the PCR for confirmation of the insertion of the target gene were carried out using the following primers.

```
[RT-PCR]
N protein Fw:
AAGGCCTCTGTCGACATGGCAAGCGGTAAGG (SEQ ID NO: 19;
the underline indicates a SalI recognition site)

N protein Rv:
AGAATTCGCAAGCTTTCAAAGTTCATTTTCACCAA (SEQ ID NO: 20;
the underline indicates a HindIII recognition site)

M protein Fw:
AAGGCCTCTGTCGACATGGAAAATTGCACACTTAAC (SEQ ID NO:
21; the underline indicates a SalI recogni-
tion site)

M protein Rv:
AGAATTCGCAAGCTTTTATGTGTAAAGACTACCCCC (SEQ ID NO:
22; the underline indicates a HindIII recognition
site)
```

[Confirmation of the Insertion of the Target Gene]

```
N protein Fw:
                              (SEQ ID NO: 23)
TAATACGACTCACTATAGGG N protein Rv:
                              (SEQ ID NO: 24)
ATGCTAGTTATTGCTCAGCGG M protein Fw:
                              (SEQ ID NO: 25)
CCCGAAAAGTGCCACCTG M protein Rv:
                              (SEQ ID NO: 26)
GTTCTGAGGTCATTACTGG
```

The following reagents and apparatuses were used.

Nucleic acid extraction: QIAamp Viral RNA Mini Kit (QIAGEN)

PCR apparatus: PCR Thermal Cycler Dice (registered trademark) Gradient (TP600) (TaKaRa)

Gel purification of DNA: QIAquick Gel Extraction Kit (QIAGEN)

Vector plasmids: pET-6×HN-N(Clontech) was used for N protein, and pQE-31 (Qiagen) was used for M protein.

Competent cells: The BL21(DE3) pLySs strain (Invitrogen) was used for N protein, and the XL1-Blue strain (Nippon Gene) was used for M protein.

Ligation: An In-Fusion (registered trademark) HD Cloning Kit (Clontech) was used for N protein, and a DNA Ligation Kit (TaKaRa) was used for M protein.

Induction of protein expression: IPTG (TaKaRa)

Sequence analysis: Outsourcing to FASMAC Co., Ltd. or Bio Matrix Research, Inc.

Affinity purification using the His tag: Profinia Protein Purification System (BioRad)

<Results>

(1) Search for Antigen Regions

As a result of comparison of the amino acid homology of the full-length N or M protein region among the 11 strains (10 strains in the case of M protein) that were recently isolated in Japan. N protein exhibited a matching rate of 93 to 99%, and M protein exhibited a matching rate of 90 to 99% indicating that both proteins are highly conserved among the strains (Table 1-1, Table 1-2). Based on this result, it could be expected that either N or M protein derived from any of the IBV may be effective as the antigen for the liposome vaccine. Since an infection test system had already been established for IBV Chiba (2004) in the inventors' lab, IBV Chiba (2004) was selected as the template. The base sequences of the expressed regions are as shown in SEQ ID NO:1 (N protein) and SEQ ID NO:3 (M protein), and the amino acid sequences of the N protein and M protein encoded thereby are as shown in SEQ ID NO:2 and SEQ ID NO:4, respectively.

TABLE 1

Degrees of conservation of the N protein region (about 410 aa) among recent widespread strains in Japan; 11 strains in total

| Amino acid matching rate (%) | Chiba (2004) | Iwate-2 (2004) | Iwate-3 (2004) | Fukuoka-3 (2010) | Hiroshima (2010) | Niigata-A (2010) | 1 (2011) | Hyogo-8 (2011) | Kagawa-1 (2010) | Kagawa-1 (2011) | Kagawa-1 (2012) |
|---|---|---|---|---|---|---|---|---|---|---|---|
| Chiba(2004) | 100 | 96 | 98 | 97 | 98 | 96 | 95 | 96 | 96 | 96 | 95 |
| Iwate-2(2004) | | 100 | 96 | 94 | 96 | 95 | 94 | 94 | 95 | 94 | 94 |
| Iwate-3(2004) | | | 100 | 97 | 99 | 96 | 95 | 96 | 97 | 96 | 95 |
| Fukuoka-3(2010) | | | | 100 | 96 | 96 | 93 | 94 | 94 | 98 | 96 |
| Hiroshima(2010) | | | | | 100 | 96 | 95 | 96 | 97 | 96 | 95 |
| Niigata-A(2010) | | | | | | 100 | 94 | 95 | 95 | 95 | 96 |
| Hyogo-1(2011) | | | | | | | 100 | 97 | 96 | 93 | 94 |
| Hyogo-8(2011) | | | | | | | | 100 | 96 | 93 | 94 |
| Kagawa-1(2010) | | | | | | | | | 100 | 94 | 96 |
| Kagawa-1(2011) | | | | | | | | | | 100 | 96 |
| Kagawa-1(2012) | | | | | | | | | | | 100 |

※The year when each strain was solated is shown in parentheses.

TABLE 2

Degrees of conservation of the M protein region (about 227 aa) among recent widespread strains in Japan; 10 strains in total

| Amino acid matching rate (%) | Chiba (2004) | Iwate-2 (2004) | Iwate-3 (2004) | Fukuoka-3 (2010) | Hiroshima (2010) | Niigata-A (2011) | 1 (2011) | Hyogo-8 (2011) | Kagawa-1 (2002) | Kagawa-1 (2011) |
|---|---|---|---|---|---|---|---|---|---|---|
| Chiba(2004) | 100 | 92 | 96 | 93 | 97 | 96 | 93 | 94 | 95 | 95 |
| Iwate-2(2004) | | 100 | 91 | 92 | 93 | 91 | 93 | 90 | 91 | 94 |
| Iwate-3(2004) | | | 100 | 95 | 95 | 99 | 94 | 94 | 98 | 96 |
| Fukuoka-3(2010) | | | | 100 | 93 | 95 | 95 | 92 | 94 | 96 |
| Hiroshima(2010) | | | | | 100 | 95 | 95 | 95 | 95 | 95 |
| Niigata-D(2011) | | | | | | 100 | 94 | 94 | 98 | 96 |
| Hyogo-1(2011) | | | | | | | 100 | 93 | 94 | 96 |
| Hyogo-8(2011) | | | | | | | | 100 | 94 | 95 |
| Kagawa-1(2002) | | | | | | | | | 100 | 96 |
| Kagawa-1(2011) | | | | | | | | | | 100 |

※The year when each strain was solated is shown in parentheses.

(2) Preparation of Recombinant Proteins by *E. coli* Expression System

A. Preparation of Recombinant *E. coli*

RT-PCR was carried out using total RNA extracted from IBV Chiba (2004) as a template, and amplification of the target gene fragment was confirmed. Regarding the recombinant N protein (IBV-rNp), the amplicon and the plasmid vector (pET6xHN-N) were ligated to each other utilizing the same two kinds of restriction enzyme regions (SalI and HindIII) in each of them, and then sequence analysis was carried out to confirm that the insertion occurred in a normal manner. *E. coli* for cloning (DH5α) was transformed with the plasmid vector, and then cultured, followed by recovering the amplified plasmid. *E. coli* for expression, the BL21 (DE3) pLySs strain, was transformed with the plasmid recovered, to prepare recombinant *E. coli* for expression of IBV-rNp. Concerning the recombinant M protein (IBV-rMp), its expression did not occur with the above combination of the plasmid vector and *E. coli* for expression. By using the combination of pQE-31 as the plasmid vector and XL1-BLUE as the *E. coli* for expression, expression of rMp could be found.

B. Induction of Expression and Purification of Recombinant Proteins

Figures 2, 3:
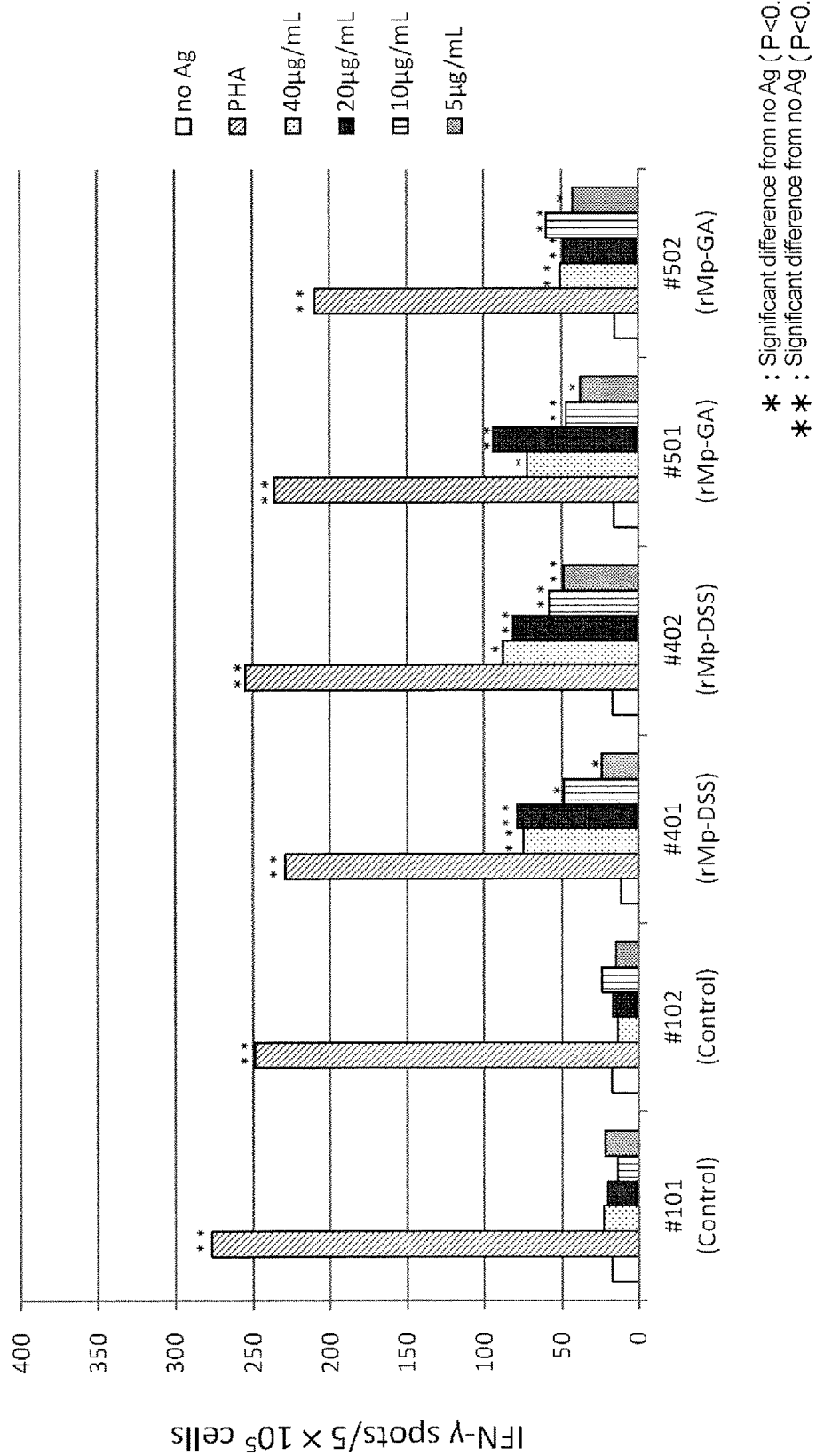
Figure 3:
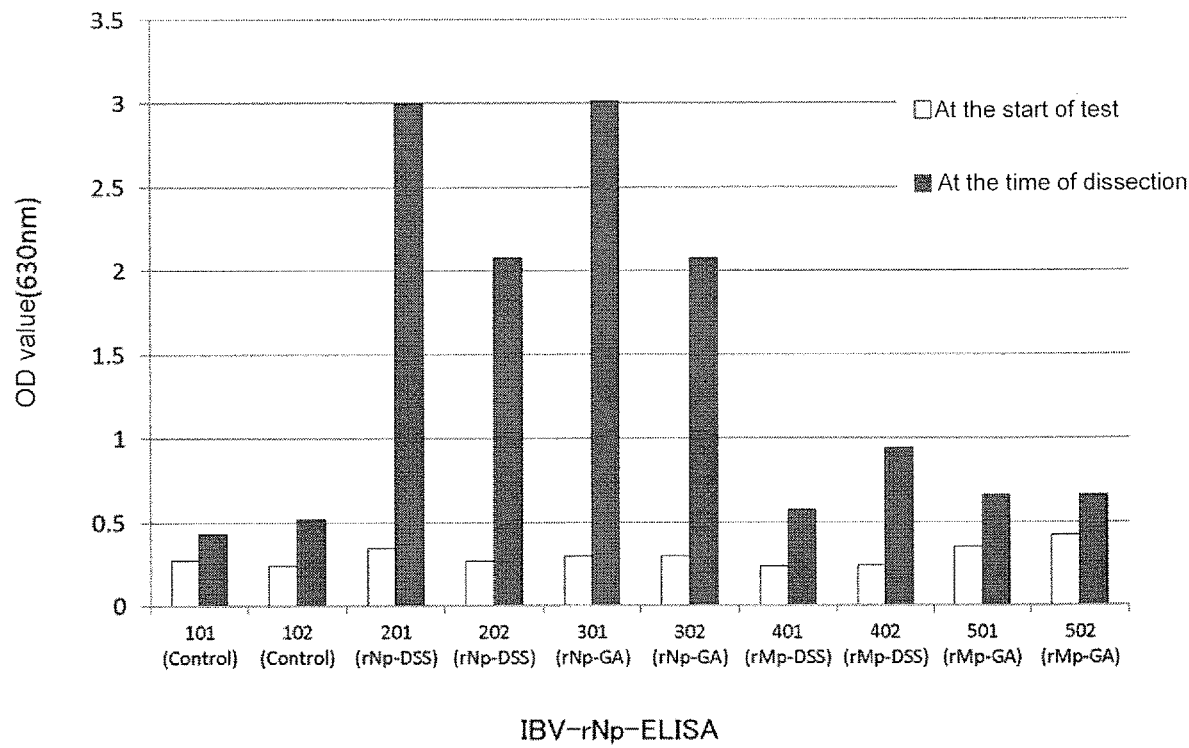

A bacterial liquid obtained by preculture in liquid LB medium supplemented with ampicillin was added to TB medium at 1/100 volume, and shake culture was carried out at 37° C. for 3 hours. The culture scale was 3 L in the case of BV-rNp, and 300 mL in the case of IBV-rMp. After the start of the culture, when O.D.600 reached 0.5. IPTG was added thereto to a final concentration of 1 mM (final 1 mM) to induce expression, and then shake culture was further carried out for 3 hours. After centrifugation at 3000 rpm for 30 min at 4° C., the bacterial pellet was collected, and a sonication buffer was added thereto. Sonication was then carried out to disrupt the bacterial cells, and the resulting crude protein solution, containing a recombinant protein, was subjected to affinity purification, to recover the recombinant protein of interest. As a result of measurement of the protein concentration, the total amount of the recombinant protein prepared was assumed to be at least 300 mg in the case of IBV-rNp, and at least 40 mg in the case of IBV-rMp. The assumed molecular weights of IBV-rNp and IBV-rMp are about 49 kDa and about 29 kDa, respectively. SDS-PAGE is known to show apparent molecular weights which are larger by several kilodaltons due to the effect of tag modification (His-tag) to antigens, and, in both cases, clear bands could be observed at positions close to the assumed molecular weights as a result of the SDS-PAGE (FIG. 1, FIG. 2).

<Conclusion>

With recombinant *E. coli*, IBV-rNp and IBV-rMp were prepared using IBV Chiba (2004) as a template. The immunogenicities of these recombinant proteins against IBV were evaluated in the following animal test.

2. Preparation of Liposome Vaccines

<Object>

The two kinds of IBV-derived recombinant antigens (IBV-rNp and IBV-rMp) prepared in 1, were subjected to liposome modification treatment to prepare liposome vaccines.

<Materials and Methods>
(1) Liposome Modification of Recombinant Antigens

Each antigen was bound to liposomes by the disuccinimidyl suberate (DDS) method or the glutaraldehyde (GA) method. According to the following protocols, test vaccines (IBV-rNp-GA and IBV-rMp-GA) were prepared.

(1-1) Liposome Modification of Antigen by DSS Method

A. Materials
  (a) Antigens: IBV-rNp and IBV-rMp, which were used at 5 mg (10 mg/mL×0.5 mL) per coupling reaction.
  (b) Liposome: DDS-bound oleic acid liposome, which was used at 90 mg lipid per coupling reaction.
  (c) Sepharose™ CL-4B (4% cross-linked agarose)
  (d) Liposome buffer: PBS supplemented with 8% sucrose, pH 7.2

B. Method (one coupling reaction); three coupling reactions were carried out for each antigen.
  (a) Freeze-dried DSS-bound oleic acid liposomes were dissolved in 2 mL of the liposome buffer.
  (b) Two milliliters of the liposome suspension was mixed with 0.5 mL of the antigen solution.
  (c) The resulting mixture was continuously stirred using a stirrer at room temperature for 48 hours.
  (d) The mixture was then passed through a CL-4B column to recover antigen-bound liposomes by the molecular sieve effect.
  (e) The total volume was adjusted to 9 mL with the liposome buffer.
  (f) Filtration was carried out through a 0.45-μm filter.
  (g) The filtered product was stored under refrigeration until use.

The DSS-bound oleic acid liposomes were prepared as described in Patent Documents 2 and 3. More specifically, the procedure was as follows.

With 50 mL of chloroform, 2 g of dioleoylphosphatidylethanolamine (DOPE) and 180 μL of triethylamine were mixed, and the resulting mixture was placed in a 300-mL four-necked flask. While the resulting mixture was stirred at room temperature using a stirrer, a solution prepared by dissolving 3 g of DDS in 80 mL of chloroform was added dropwise thereto for 4 hours, to react the amino group of DOPE with one end of DDS. The resulting crude reaction solution was transferred into an eggplant-type flask, and the solvent was removed by distillation using an evaporator. Subsequently, the minimum amount of chloroform with which the crude reaction product can be dissolved was added to the flask, to obtain a highly concentrated crude reaction product solution. The solution was then subjected to column chromatography according to a conventional method using a silica gel equilibrated with chloroform/methanol/water (65/25/1, volume ratio), and only the fraction of interest, in which the amino group of DOPE is bound to one end of DDS, was collected, followed by removing the solvent by distillation, to obtain DDS (suberic acid succinimide group)-bound DOPE, which is the reactive phospholipid of interest.

In an eggplant-type flask, 0.2886 g (0.2831 mmol) of the above-obtained DDS-bound DOPE, 1.3354 g (1.6987 mmol) of dioleoylphosphatidylcholine (DOPC), 0.7663 g (1.9818 mmol) of cholesterol, and 0.4513 g (0.5662 mmol) of dioleoylphosphatidylglycerol (DOPG) Na salt were placed, and 50 mL of a mixed solvent of chloroform/methanol/water (65/25/4, volume ratio) was added thereto, followed by allowing dissolution at 40° C. Subsequently, the solvent was removed by distillation under reduced pressure using a rotary evaporator, to prepare a lipid film. Thereafter, 30 mL of distilled water for injection was added thereto, and the resulting mixture was stirred to obtain a homogeneous slurry. The slurry was then frozen, and dried in a freeze dryer for 24 hours, to obtain a mixed lipid powder.

Subsequently, 60 mL of a separately prepared buffer (1.0 mM $Na_2HPO_4$/$KH_2PO_4$, 0.25 M saccharose; pH7.4) was added to the eggplant-type flask containing the mixed lipid powder, and then the resulting mixture was stirred at 40° C. to allow hydration of the lipids, to obtain liposomes. Subsequently, the particle size of the liposomes was adjusted using an extruder. First, the liposomes were passed through an 8-μm polycarbonate filter, and then through 5-μm, 3-μm, 1-μm, 0.65-μm, 0.4-μm, and 0.2-μm filters in this order. By this, liposome particles having an average particle size of 206 nm (as measured by the dynamic light scattering method) (DOPE:DOPC:cholesterol:DOPG=1:6:7:2 (molar ratio)) were obtained. The liposome particle suspension was freeze-dried to provide DDS-bound oleic acid liposomes, which were used for the above-described liposome modification of the antigen by the DSS method.

(1-2) Liposome Modification of Antigen by GA Method

A. Materials
  (a) Antigens: IBV-rNp and IBV-rMp, which were used at 5 mg (2 mg/ml×2.5 ml) per coupling reaction.
  (b) Liposome: Oleic acid liposome, which was used at 90 mg lipid per coupling reaction.
  (c) 2.5% Glutaraldehyde solution
  (d) Saturated glycine-NaOH solution (pH 7.2)
  (e) Sepharose™ CL-4B (4% cross-linked agarose)
  (f) Liposome buffer: PBS supplemented with 8% sucrose, pH 7.2

B. Method (One Coupling Reaction); Each Antigen was Subjected to Three Coupling Reactions.
  (a) Two milliliters of the liposome suspension was mixed with 2.5 mL of the antigen solution.
  (b) To the resulting mixture, 0.5 mL of 2.5% glutaraldehyde solution was added.
  (c) The resulting mixture was gently stirred in a water bath at 37° C. for 1 hour.
  (d) The excessive GA was deactivated by addition of 0.5 mL of saturated glycine-NaOH solution.
  (e) The mixture was then left to stand at 4° C. overnight.
  (f) The mixture was then passed through a CL-4B column to recover antigen-bound liposomes.
  (g) The total volume was adjusted to 9 mL with the liposome buffer.
  (h) Filtration was carried out through a 0.45-μm filter.
  (i) The filtered product was stored under refrigeration.

The oleic acid liposomes used in the GA method were prepared according to the preparation method for the DSS-bound oleic acid liposomes described above, with a molar ratio of DOPE:DOPC:cholesterol:DOPG=3:4:7:2. Sizing of the liposomes was carried out using a polycarbonate filter, and then the liposome suspension was freeze-dried. The liposomes were then dissolved in a buffer (1.0 mM $Na_2HPO_4$/$KH_2PO_4$, 0.25 M saccharose; pH 7.4) to a concentration of 90 mg/2 mL, to provide an oleic acid liposome suspension, which was used for the above-described liposome modification of the antigen by the GA method.

(2) Quantification of Antigen Protein

Using a commercially available kit utilizing the BCA method (Pierce (trade name) BCA Protein Assay Kit—Reducing Agent Compatible (Thermo Fisher Scientific Inc.)), the antigen protein bound to the liposome surface was quantified.

<Results>

(1) Liposome Modification of Antigen by DSS Method

The freeze-dried DSS-bound oleic acid liposome powder (90 mg lipid/vial) was rehydrated with distilled water to a total volume of 2 mL per coupling reaction. To the resulting liquid, 0.5 mL of the antigen, whose concentration was adjusted to 10 mg/mL, was added, and the resulting mixture was stirred using a stirrer at room temperature for 48 hours. Three coupling reactions were carried out for each antigen. A column packed with CL-4B (4% cross-linked agarose gel) was equilibrated with PBS, and then the antigen-liposome mixture was applied thereto, to recover a fraction of antigen-bound liposomes by the molecular sieve effect (9 mL/coupling). The fraction was then filtered (0.45 μm) to provide a test vaccine (IBV-rNp-DSS or IBV-rMp-DSS). The liquid volume of each test vaccine finally collected was about 25 mL.

(2) Liposome Modification of Antigen by GA Method

For each coupling reaction, 2.5 mL of the antigen, whose concentration was adjusted to 2 mg/mL, was added to the oleic acid liposome suspension (90 mg lipid/vial/2 mL). Subsequently, 0.5 mL of 2.5% glutaraldehyde solution was added to the resulting mixture, and, immediately thereafter, the mixture was shaken in a water bath at 37° C. for 1 hour. After neutralizing the residual aldehyde groups by addition of 0.5 mL of saturated glycine-NaOH solution (pH 7.0), the mixture was left to stand at 4° C. overnight. The purification and the filtration were carried out by the same process as in the DSS method. The liquid volume of each test vaccine (IBV-rNp-GA or IBV-rMp-GA) finally collected was about 25 mL.

(3) Quantification of Antigen Protein

The quantification results are shown below in Table 2-1.

TABLE 2-1

Quantification of antigen protein

| | Test vaccine | Antigen | Binding method | Protein concentration (μg/ml) | Binding efficiency (%) |
|---|---|---|---|---|---|
| 1 | IBV-rNp-DSS | IBV-rNp | DSS | 227.8 | 40.7 |
| 2 | IBV-rNp-GA | | GA | 217.7 | 38.9 |
| 3 | IBV-rMp-DSS | IBV-rMp | DSS | 180.8 | 32.3 |
| 4 | IBV-rMp-GA | | GA | 209 | 37.3 |

<Conclusion>

By using IBV-rNp or IBV-rMp as an antigen, and by carrying out liposome modification of the antigen by the DSS method or GA method, a total of four kinds of test vaccines were prepared. The performances of these test vaccines were evaluated in the following animal test.

3. Evaluation of Immunogenicities of Test Vaccines

<Object>

SPF chickens were immunized with each of the four kinds of test vaccines prepared in 2, and subjected to evaluation of the antigen-specific IFN-γ production-inducing ability and antibody production-inducing ability, to select the test vaccines to be used for the later challenge study.

<Materials and Methods>

(1) Animal Test

The test group setting and the animal test schedule were as shown in Table 3-1 and Table 3-2.

TABLE 3-1

Test group setting

| Test group | Number of chickens | Test vaccine | Administration route | Dose (mL/dose/body) | Amount of antigen (μg/dose/body) |
|---|---|---|---|---|---|
| Group 1 | 2 | — | — | — | — |
| Group 2 | 2 | IBV-rNp-DSS | Intra-leg muscle | 1 | 227.8 |
| Group 3 | 2 | IBV-rNp-GA | | | 217.7 |
| Group 4 | 2 | IBV-rMp-DSS | | | 180.8 |
| Group 5 | 2 | IBV-rMp-GA | | | 209 |

TABLE 3-2

Animal test schedule

| | Age in weeks | | | |
|---|---|---|---|---|
| Test group | 6 | 8 | 10 | 11 |
| Unimmunized group (Group 1) | — | — | — | Autopsy |
| Immunization groups (Groups 2, 3, 4, 5) | First immunization | Booster immunization | Booster immunization | |

(2) Evaluation of IFN-γ Production-Inducing Ability

Using lymphocytes collected from the spleen of each test chicken, the antigen-specific IFN-γ production-inducing ability was measured by ELISPOT for detection of chicken IFN-γ.

(3) Evaluation of Antibody-Inducing Ability

Using serum of each test chicken, the antigen-specific blood antibody titer was measured by ELISA.

<Results>

(1) Animal Test

Six-week-old SPF chickens were immunized by a total of three times of injection of a test vaccine into the leg muscle (1 mL per injection) at 2-week intervals. After the immunization, no side reaction such as swelling or induration was found at the injection site. One week after the final immunization, each chicken was dissected to collect spleen. In addition, at the start of the test and during the dissection, sera for ELISA were collected.

(2) Evaluation of IFN-γ Production-Inducing Ability

To a single-cell suspension prepared from the spleen of the test chicken, a test vaccine antigen (IBV-rNp or IBV-rMp) was added at 5 to 40 μg/mL as a stimulating antigen, and the cells were then cultured in a 5% $CO_2$ incubator at 41° C. for 20 hours. The lymphocytes activated in response to the stimulating antigen produced IFN-γ, and the sites of the production appeared as spots on the well. The number of the spots was counted to evaluate the antigen-specific IFN-γ production-inducing ability. As a result, for all test vaccines, significant activities of lymphocytes against antigen stimulation at not less than 5 μg/mL could be found, and there was a positive correlation between the number of spots and the concentration of the stimulating antigen (FIG. 3-1, FIG. 3-2). For each antigen, no large difference in the number of spots was found between the binding methods. Based on comparison at each stimulating antigen concentration, IBV-rNp tended to show a larger number of spots than IBV-rMp. There was no large difference in the result among the test chickens within each test group.

(3) Evaluation of Antibody-Inducing Ability

Figures 3, 4:
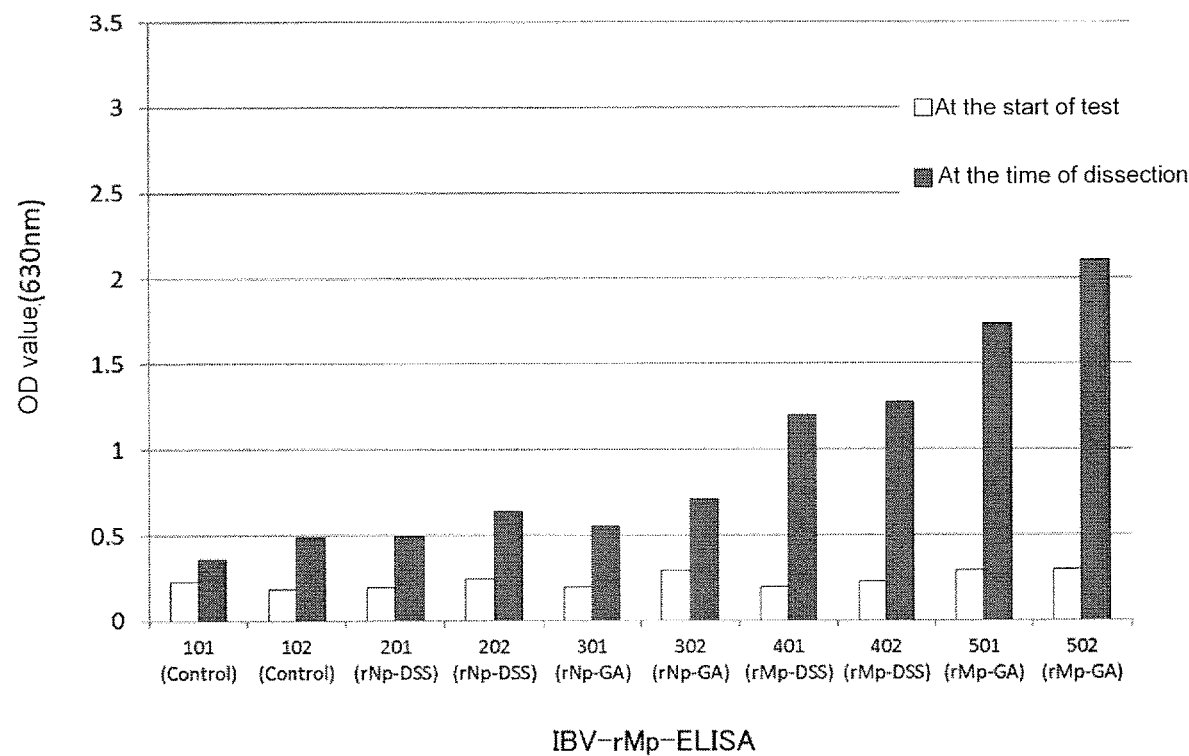

Using 3 μg/well of IBV-rNp or IBV-rMp as an antigen, ELISA was carried out to measure the blood antibody titers before and after the immunization. As a result, induction of specific antibody due to the immunization with the test vaccine was found (FIG. 3-3, FIG. 3-4).

<Conclusion>

In the immunization method in which the vaccine was injected a plurality of times into the leg muscle of 6-week-old SPF chickens, any of the test vaccines showed activation of IFN-γ-producing lymphocytes and antibody induction. Since no large difference in the activation of IFN-γ-producing lymphocytes was found between the antigen types or between the methods of binding to the liposome, all four kinds of test vaccines were compared with each other in terms of the protection effect in the following challenge test using a highly virulent homologous strain.

4. Evaluation of Effectiveness of Test Vaccines (1)

<Object>

SPF chickens were immunized with each of the four kinds of test vaccines prepared in 2, and thereafter, the chickens were challenged with the IBV Chiba (2002) strain (highly virulent homologous strain), from which the antigen protein was derived. By this, the effectiveness of each test vaccine was evaluated.

<Materials and Methods>

(1) Animal Test

The test group setting and the animal test schedule were as shown in Table 4-1 and Table 4-2. For the evaluation of the effectiveness (protection effect) of each test vaccine, a test group using the IBV Chiba strain MSV, which was prepared by attenuation of the IBV Chiba (2002) strain, as a live vaccine was set up, and this test group was used as a positive control group (test group showing an evident protection effect). In addition, a test group in which only the challenge is carried out was set up to provide a challenge control group.

TABLE 4-1

Test group setting

| Test group | Number of chickens | Immunization material | Administration route | Amount of antigen/virus titer | Dose (mL/dose · body) | Challenge |
|---|---|---|---|---|---|---|
| Group 1 | 5 | IBV-rNp-DSS | Intra-leg muscle | 227.8 μg/mL | 0.5 | Chiba(2002) |
| Group 2 | 5 | IBV-rNp-GA |  | 217.7 μg/mL |  |  |
| Group 3 | 5 | IBV-rMp-DSS |  | 180.8 μg/mL |  |  |
| Group 4 | 5 | IBV-rMp-GA |  | 209 μg/mL |  |  |
| Group 5 | 5 | Live vaccine | Ocular instillation | 5.0 logEID$_{50}$/mL | 0.03 |  |
| Group 6 | 5 | — | — | — |  |  |

TABLE 4-2

Animal test schedule

| Test group | Content | Schedule (Day) | | | | | |
|---|---|---|---|---|---|---|---|
| | | 0 | 14 | 21 | 28 | 35 | 42 |
| Groups 1 to 4 | Test vaccine | First immunization | Booster immunization | | Booster immunization | Challenge | Autopsy |
| Group 5 | Live vaccine | | | First immunization | | | |
| Group 6 | Challenge control | | | | | | |

(2) Evaluation Items

A. Evaluation Based on Tracheal Ciliary Movement Score

As is commonly carried out for evaluation of the respiratory symptoms after IBV infection, the tracheal ciliary movement activity was scored. More specifically, for the trachea collected from each test chicken by the autopsy, tracheal rings were prepared at five sites per individual in the lab. For each of these, activity of the tracheal ciliary movement was observed under the microscope, and scoring was carried out according to the following criteria:

0=active movement; 1=rather weak; 2=very weak/partial movement; 3=arrest.

After calculating the average score for each individual, the score for each test group was calculated.

*A higher score indicates that the respiratory damage caused by IBV is severer (the protection effect of the vaccine is lower).

B. Quantification of Viral Gene in Organs

From trachea and kidney collected by the autopsy, 10% (w/v) organ emulsions were prepared, and centrifugation was carried out at 3000 rpm at 4° C. for 20 min, followed by collecting the supernatant.

C. Isolation of Virus from Organs

From trachea and kidney collected by the autopsy, 10% (w/v) organ emulsions were prepared, and centrifugation was carried out at 3000 rpm at 4° C. for 20 min, followed by collecting the supernatant. The emulsion supernatant, after 10-fold serial dilution with PBS, was inoculated to primary renal cells derived from SPF chickens (hereinafter referred to as CK cells), and, on Day 4 after the inoculation, the cells were observed for the presence or absence of the cytopathic effect characteristic to IBV. By this, virus isolation was confirmed, and the virus titer was measured.

D. Measurement of Neutralizing Antibody Titer

Sera of each individual collected at the times of the challenge and autopsy were subjected to measurement of the neutralizing antibody titer against the IBV Chiba (2002) strain using CK cells derived from SPF chickens.

<Results>

(1) Animal Test

A total of six test groups were set up, and five chickens were tested for each test group. In the four test vaccine groups, 0.5 mL of a test vaccine was injected into the leg muscle at 5 weeks old, 7 weeks old, and 9 weeks old. In the live vaccine group, 30 μL each of 1 dose (3.5 log $EID_{50}$/body) of the IBV Chiba strain MSV was inoculated by ocular instillation at 8 weeks old. In all test groups including the challenge control group, each chicken was challenged by intratracheal inoculation of 50 μL of 3.5 log $EID_{50}$/body of the Chiba (2002) strain at 10 weeks old. The chickens were kept under observation of clinical symptoms, and subjected to autopsy at Week 1 after the challenge. For the organs and sera collected upon the challenge and autopsy, observation of the tracheal ciliary movement, isolation of the virus, quantification of the viral gene, and measurement of the neutralizing antibody titer were carried out.

(2) Evaluation Based on Tracheal Ciliary Movement Score

Compared to the challenge control group, the IBV-rNp-DSS group and the IBV-rNp-GA group showed lower suppression of the tracheal ciliary movement (FIG. 4-1). On the other hand, the IBV-rMp-DSS group and the IBV-rMp-GA group showed results equivalent to the result in the challenge control group.

(3) Quantification of Viral Gene in Organs

In all test groups, viral gene was detected from trachea and kidney collected by the autopsy (FIG. 4-2). Compared to the challenge control group, the IBV-rNp-DSS group and the IBV-rNp-GA group tended to show decreased amounts of viral gene in the organs.

(4) Virus Isolation and Measurement of Virus Titer

Compared to the challenge control group, the IBV-rNp-DSS group and the IBV-rNp-GA group showed decreased virus isolation rates from the organs and decreased average virus titers in the isolation-positive samples (FIG. 4-3). On the other hand, the IBV-rMp-DSS group and the IBV-rMp-GA group showed results equivalent to those in the challenge control group.

(5) Measurement of Neutralizing Antibody Titer

Regarding the neutralizing antibody titer upon the challenge, the live vaccine group showed a 23-fold titer, while all test vaccine groups showed less than 4-fold titers. At Week 1 after the challenge, all test vaccine groups showed increased titers of about 16-fold. However, these titers were equivalent to the titer in the challenge control group (FIG. 4-4).

<Conclusion>

As a result of evaluation of the effectiveness of the four kinds of test vaccines against the IBV Chiba (2002) strain, which corresponds to the antigen homologous strain, the two kinds of test vaccines using IBV-rNp as the antigen were found to have an effect to reduce the symptom onset. On the other hand, an effect to reduce the symptom onset was not found with the test vaccines using IBV-rMp as the antigen.

5. Evaluation of Effectiveness of Test Vaccines (2)

<Object>

SPF chickens immunized using IBV-rNp-DSS or IBV-rNp-GA, for which a certain level of effectiveness (symptom onset-reducing effect) was found in 4, among the four kinds of test vaccines prepared in 2, were challenged with highly virulent heterologous strains having genotypes which are the same as or different from the genotype of the IBV Chiba (2002) strain, from which the antigen protein was derived, to evaluate the effectiveness of IBV-rNp-DSS and IBV-rNp-GA.

<Materials and Methods>

(1) Animal Test

The test group setting and the test schedule were as shown in Table 5-1 and Table 5-2. For evaluation of the effectiveness (protection effect) of each test vaccine, chickens were challenged with three kinds of highly virulent heterologous field strains. In addition, a test group in which only the challenge is carried out was set up to provide a challenge control group.

TABLE 5-1

| Test group setting | | | | | | |
|---|---|---|---|---|---|---|
| Test group | Number of chickens | Test vaccine | Antigen concentration (μg/mL) | Immunization route | Dose (mL/body) | Challenge strain (genotype) |
| Group 1 | 5 | IBV-rNp-DSS | 200 | Injection into leg muscle | 0.5 | Niigata/2010 strain |
| Group 2 | 5 | IBV-rNp-GA | | | | |

TABLE 5-1-continued

Test group setting

| Test group | Number of chickens | Test vaccine | Antigen concentration (μg/mL) | Immunization route | Dose (mL/body) | Challenge strain (genotype) |
|---|---|---|---|---|---|---|
| Group 3 | 5 | IBV-rNp-DSS | | Ocular instillation | 0.1 | (JP-II) |
| Group 4 | 5 | None | — | — | — | |
| Group 5 | 5 | IBV-rNp-DSS | 200 | Injection into leg muscle | 0.5 | Ehime/2011 strain |
| Group 6 | 5 | IBV-rNp-GA | | | | |
| Group 7 | 5 | IBV-rNp-DSS | | Ocular instillation | 0.1 | (JP-III) |
| Group 8 | 5 | None | — | — | — | |
| Group 9 | 5 | IBV-rNp-DSS | 200 | Injection into leg muscle | 0.5 | Kagawa/2012/1 strain |
| Group 10 | 5 | IBV-rNp-GA | | | | |
| Group 11 | 5 | IBV-rNp-DSS | | Ocular instillation | 0.1 | (JP-IV) |
| Group 12 | 5 | None | — | — | — | |

TABLE 5-1

Animal test schedule

| | Age in weeks | | | | |
|---|---|---|---|---|---|
| Test group | 5 | 7 | 9 | 10 | 11 |
| Immunization groups (1, 2, 3, 5, 6, 7, 9, 10, 11) | First immunization | Booster immunization | Booster immunization | Challenge Observation | Autopsy |
| Challenge control groups (4, 8, 12) | — | — | — | | |

(2) Evaluation Items

The following items were evaluated in the same manner as in 4.
 A. Evaluation based on the tracheal ciliary movement score
 B. Quantification of viral gene in organs
 C. Isolation of virus from organs <Results>

(1) Animal Test

A total of 12 test groups were set up, and five chickens were tested for each test group. In the intramuscular injection immunization group, 0.5 mL each of the test vaccine was injected into the leg muscle at 5 weeks old, 7 weeks old, and 9 weeks old. In the ocular instillation immunization group, 0.1 mL each of the test vaccine was administered by ocular instillation at 5 weeks old, 7 weeks old, and 9 weeks old. In all test groups including the challenge control group, each chicken was challenged by intratracheal inoculation of 3.5 log $EID_{50}$/body (50 μL/body) of the challenge virus at 10 weeks old. The chickens were kept under observation of clinical symptoms, and then subjected to autopsy at Week 1 after the challenge, for collecting trachea and kidney. Further, blood was collected at the times of the challenge and autopsy.

(2) Evaluation Based on Tracheal Ciliary Movement Score

Figures 1, 5:
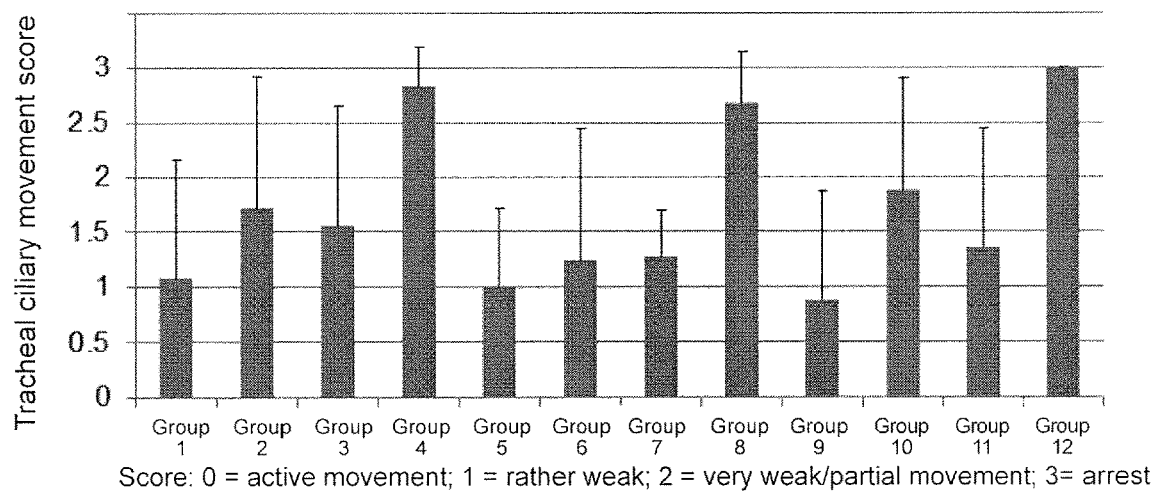
Figures 2, 5:
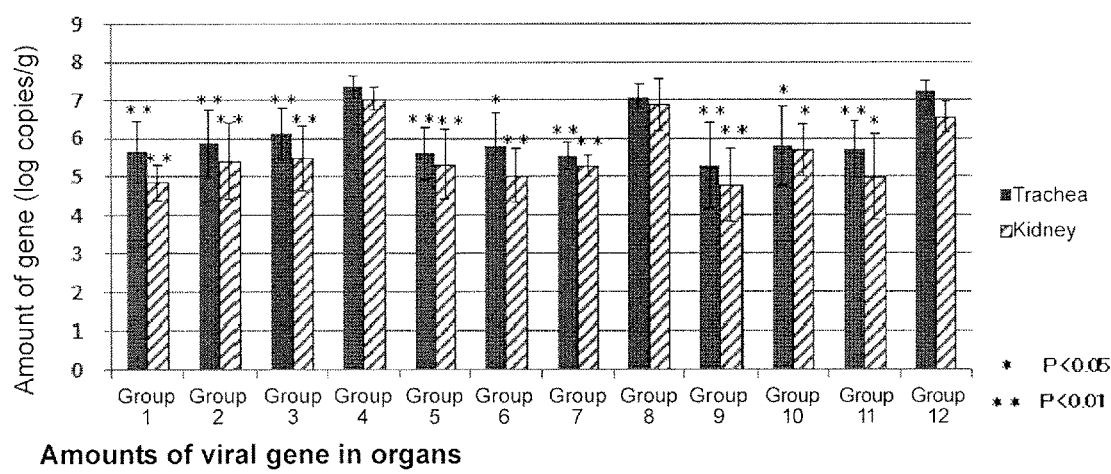
Figures 3, 5:
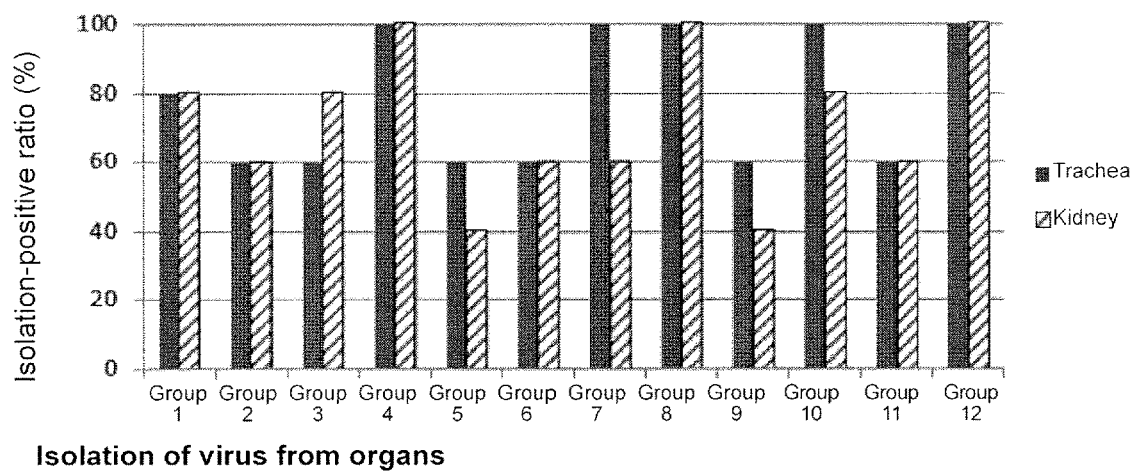
Figures 4, 5:
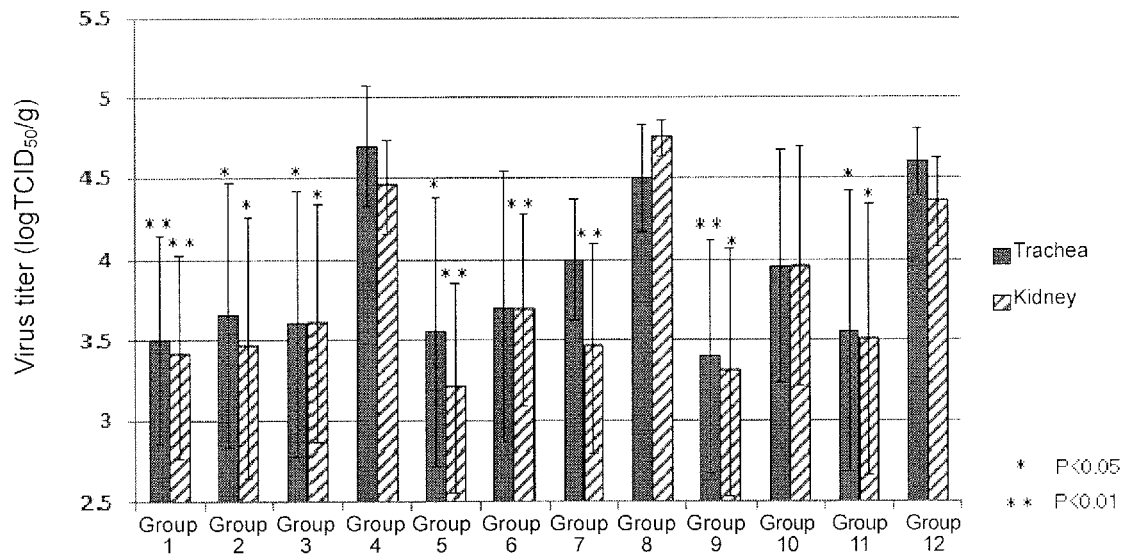

Compared to the challenge control group, all immunization groups showed certain levels of reduction of the suppression of the tracheal ciliary movement. No evident difference in the effectiveness was found among the challenge strains (FIG. 5-1). Regarding comparison between the administration routes, intramuscular injection tended to show higher suppression-reducing effects than ocular instillation. However, variation of the suppression-reducing effect was found also within each test group (Table 5-3).

TABLE 5-3

Distribution of the tracheal ciliary movement score

| | Number of chickens with each score | | |
|---|---|---|---|
| Test group | 0 to less than 1 | 1 to less than 2 | 2 to 3 |
| Group 1 | 2 | 2 | 1 |
| Group 2 | 1 | 2 | 2 |
| Group 3 | 1 | 2 | 2 |
| Group 4 | 0 | 0 | 5 |
| Group 5 | 1 | 3 | 1 |
| Group 6 | 2 | 2 | 1 |
| Group 7 | 0 | 4 | 1 |
| Group 8 | 0 | 0 | 5 |
| Group 9 | 2 | 2 | 1 |
| Group 10 | 0 | 3 | 2 |
| Group 11 | 1 | 3 | 1 |
| Group 12 | 0 | 0 | 5 |

(3) Quantification of Viral Gene in Organs

In all test groups, viral gene was detected from trachea and kidney collected by the autopsy (Table 5-4). Compared to the challenge control group, the immunization groups showed significantly smaller amounts of viral gene in the organs (FIG. 5-2).

TABLE 5-4

Positive ratio in each test group as measured by real-time PCR (%)

| Test group | Trachea | Kidney |
|---|---|---|
| Group 1 | 100 | 100 |
| Group 2 | 100 | 100 |
| Group 3 | 100 | 100 |
| Group 4 | 100 | 100 |

TABLE 5-4-continued

Positive ratio in each test group as measured by real-time PCR (%)

| Test group | Trachea | Kidney |
|---|---|---|
| Group 5 | 100 | 100 |
| Group 6 | 100 | 100 |
| Group 7 | 100 | 100 |
| Group 8 | 100 | 100 |
| Group 9 | 100 | 100 |
| Group 10 | 100 | 100 |
| Group 11 | 100 | 100 |
| Group 12 | 100 | 100 |

(4) Virus Isolation and Measurement of Virus Titer

Compared to the challenge control group, all immunization groups tended to show decreased virus isolation rates from trachea and kidney collected by the autopsy, and decreased average virus titers (FIG. 5-3, FIG. 5-4). All challenge strains and administration routes showed similar virus isolation rates and virus titers. Chickens showing high tracheal ciliary movement scores (2.0 or higher on average) tended to correspond to virus isolation-positive chickens.

<Conclusion>

The test liposome vaccines using IBV-rNp as the antigen showed certain levels of symptom onset-reducing effect against the three highly virulent heterologous strains. In the ocular instillation groups, the amount of antigen used was one-fifth the amount in the intramuscular injection groups. However, the symptom onset-reducing effect in the ocular instillation groups was only slightly lower than that in the groups employing the intramuscular injection route. When IBV-rNp-DSS and IBV-rNp-GA were used under the same conditions, IBV-rNp-DSS tended to show relatively higher effectiveness. Therefore, IBV-rNp-DSS was used in the following studies.

6. Evaluation of Effectiveness of Test Vaccines (3)

<Object>

Since IBV is widespread in the environment, vaccination is commonly carried out at birth (0-day-old). Since the above animal tests in the present study were carried out using 5-week-old chicks, the effectiveness for newborn chicks, whose development of the immune system is more immature, has been unclear. In view of this, using IBV-rNp-DSS as a test vaccine, the effectiveness of the vaccine for newborn chicks was evaluated by setting conditions regarding the administration route, antigen concentration, and number of doses.

<Materials and Methods>

(1) Animal Test

The test group setting and the test schedule were as shown in Table 6-1 and Table 6-2. For evaluation of the effectiveness (protection effect) of IBV-rNp-DSS, conditions regarding the antigen concentration and the number of times of immunization were set for each of three kinds of administration routes, and immunization was carried out. Thereafter, a challenge with a highly virulent heterologous strain was carried out. In addition, a test group in which only the challenge is carried out was set up to provide a challenge control group.

TABLE 6-1

Test group setting

| Test group | Number of chickens | Test vaccine | Administration route | Antigen concentration in vaccine stock solution (µg/mL) | Fold-concentration | Dose (µL/body) | Number of times of immunization | Challenge strain |
|---|---|---|---|---|---|---|---|---|
| 1 | 4 | IBV-rNp-DSS | Ocular instillation | 200 | 4 | 50 | 1 | Kagawa/2012/1 strain |
| 2 | 4 | | | | 4 | | 3 | |
| 3 | 4 | | | | None | | 1 | |
| 4 | 4 | | | | None | | 3 | |
| 5 | 4 | IBV-rNp-DSS | Nasal instillation | 200 | 4 | 50 | 1 | |
| 6 | 4 | | | | 4 | | 3 | |
| 7 | 4 | | | | None | | 1 | |
| 8 | 4 | | | | None | | 3 | |
| 9 | 4 | IBV-rNp-DSS | Intra-leg muscle | 200 | 4 | 50 | 1 | |
| 10 | 4 | | | | 4 | | 3 | |
| 11 | 4 | | | | None | | 1 | |
| 12 | 4 | | | | None | | 4 | |
| 13 | 4 | None | — | | — | — | — | — |

TABLE 6-2

Test schedule

| Test group | Age in days | | | | |
|---|---|---|---|---|---|
| | 0 | 7 | 14 | 21 | 28 |
| Single-immunization groups | Immunization | — | — | Challenge | Autopsy |
| Three-immunization groups | Immunization | Immunization | Immunization | | |
| Challenge control group | — | — | — | | |

(2) Evaluation Items

The following items were evaluated in the same manner as in 4.
 A. Evaluation based on the tracheal ciliary movement score
 B. Quantification of viral gene in organs
 C. Isolation of virus from organs <Results>

(1) Animal Test

A total of 13 test groups were set up, and four chicks were tested for each test group. As the administration routes, ocular instillation, nasal instillation, and intramuscular injection were set up. As an immunizing material, the stock solution of IBV-rNp-DSS, or a 4-fold concentrated solution prepared by freeze-drying the stock solution and rehydrating the freeze-dried product with 1/4 volume of PBS, was used. Administration of 50 µL each of the test vaccine was carried out only at birth in the single-immunization group; and at birth, 7 days old, and 14 days old in the three-immunization group. In all test groups including the challenge control group, each chick was challenged by nasal instillation inoculation of 3.5 log $EID_{50}$/body (50 µL/body) of the challenge strain at 21 days old. The chicks were kept under observation of clinical symptoms, and then subjected to autopsy at Week 1 after the challenge, for collecting trachea and kidney.

(2) Evaluation Based on Tracheal Ciliary Movement Score

Figures 1, 6:
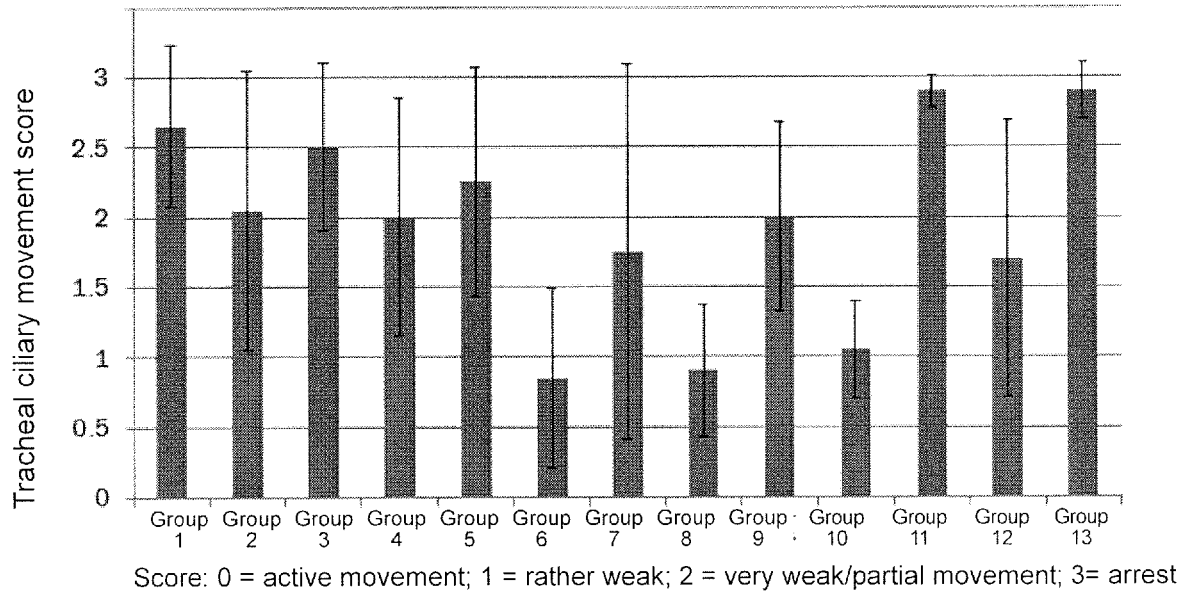
Figures 2, 6:
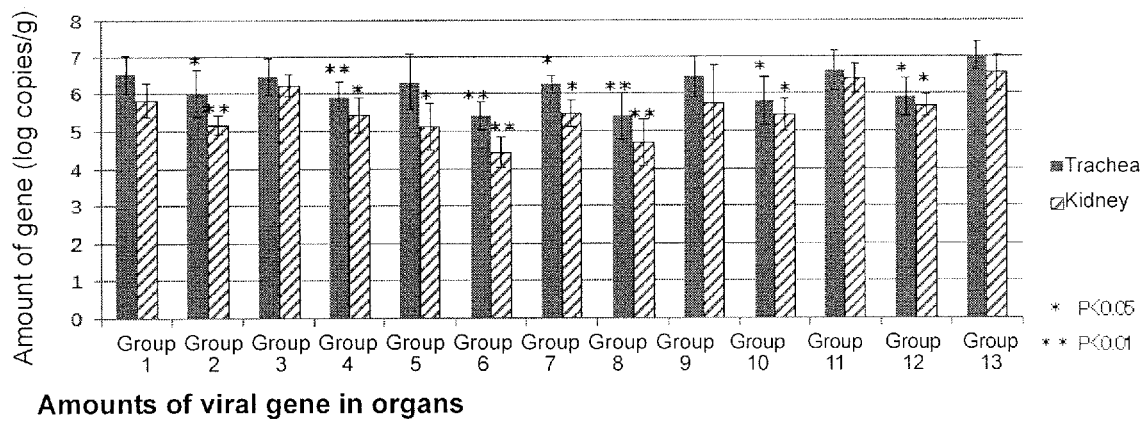
Figures 3, 6:
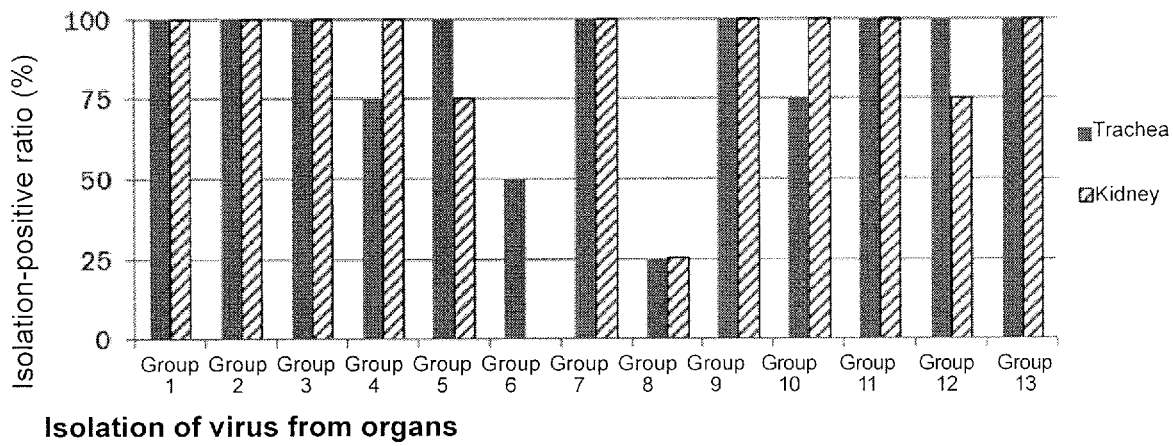
Figures 4, 6:
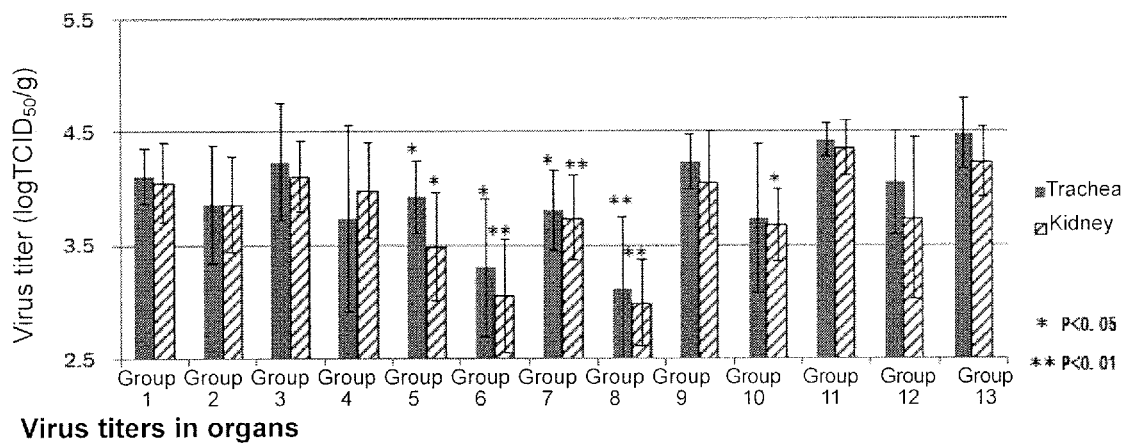

In the test groups in which the immunization was carried out three times with the 4-fold concentrate or stock solution of IBV-rNp-DSS by the nasal instillation route (Group 6 and Group 8), and the test group in which the immunization was carried out three times with the 4-fold concentrate of IBV-rNp-DSS by the intramuscular route (Group 10), the suppression of the tracheal ciliary movement tended to be reduced (FIG. 6-1). However, variation of the score among individuals was found also within each test group (Table 6-3).

TABLE 6-3

Distribution of the tracheal ciliary movement score

| | Number of chickens with each score | | |
|---|---|---|---|
| Test group | 0 to less than 1 | 1 to less than 2 | 2 to less than 3 |
| Group 1 | 0 | 1 | 3 |
| Group 2 | 0 | 2 | 2 |
| Group 3 | 0 | 1 | 3 |
| Group 4 | 0 | 2 | 2 |
| Group 5 | 0 | 1 | 3 |
| Group 6 | 3 | 1 | 0 |
| Group 7 | 2 | 0 | 2 |
| Group 8 | 3 | 1 | 0 |
| Group 9 | 0 | 3 | 1 |
| Group 10 | 1 | 3 | 0 |
| Group 11 | 0 | 0 | 4 |
| Group 12 | 1 | 2 | 1 |
| Group 13 | 0 | 0 | 4 |

(3) Quantification of Viral Gene in Organs

Viral gene was detected from the trachea and kidney in all immunization groups. However, for any of the administration routes, the test groups in which the immunization was carried out three times showed significant decreases in the amount of viral gene in the trachea or kidney (FIG. 6-2, Table 6-4).

TABLE 6-4

| Positive ratio as measured by real-time PCR (%) | | |
|---|---|---|
| Test group | Trachea | Kidney |
| Group 1 | 100 | 100 |
| Group 2 | 100 | 100 |
| Group 3 | 100 | 100 |
| Group 4 | 100 | 100 |
| Group 5 | 100 | 100 |
| Group 6 | 100 | 100 |
| Group 7 | 100 | 100 |
| Group 8 | 100 | 100 |
| Group 9 | 100 | 100 |
| Group 10 | 100 | 100 |
| Group 11 | 100 | 100 |
| Group 12 | 100 | 100 |
| Group 13 | 100 | 100 |

(4) Virus Isolation and Measurement of Virus Titer

In the test groups in which the immunization was carried out three times by the nasal instillation route (Group 6 and Group 8), the virus isolation rates from the organs decreased (FIG. 6-3). In the cases of the nasal instillation route, the virus titers in the organs significantly decreased even by the single immunization, but the virus titers further decreased by the three times of immunization (FIG. 6-4).

<Conclusion>

IBV-rNp-DSS was found to have a certain level of symptom onset-reducing effect also for newborn chicks. Among the immunization methods in the present study, the three times of administration by the nasal instillation route was most effective. In the cases of the nasal instillation route, no large difference in the effectiveness was found between the different antigen concentrations.

7. Study of Test Vaccine Administration Method (1)

<Object>

Since IBV-rNp-DSS showed high effectiveness by the nasal instillation route in 6, the effectiveness of spray administration (coarse spray or fine spray) was studied assuming its on-site application.

<Materials and Methods>

(1) Animal Test

The test group setting and the test schedule were as shown in Table 7-1 and Table 7-2. Conditions regarding the antigen concentration and the number of times of immunization were set for each of three kinds of administration routes, and immunization was carried out. Thereafter, a challenge with a highly virulent heterologous strain was carried out. In addition, a test group in which only the challenge is carried out was set up to provide a challenge control group. The droplet particle size was adjusted using a live-vaccine power sprayer (Nyukon 607, Kimura Nosan) to 250 to 300 m for the coarse spray administration, and to 50 to 100 µm for the fine spray administration.

TABLE 7-1

| Test group setting | | | | | | | | |
|---|---|---|---|---|---|---|---|---|
| Test group | Number of chickens | Test vaccine | Administration route | Antigen concentration in vaccine stock solution (µg/mL) | Fold-dilution | Dose (µL/body · dose) | Number of times of immunization | Challenge strain |
| 1 | 4 | IBV-rNp-DSS | Nasal instillation | 200 | None | 50 | 2 | Kagawa/2012/1 strain |
| 2 | 4 | | | | 10 | | 2 | |
| 3 | 4 | | | | 100 | | 2 | |
| 4 | 4 | | | | None | | 1 | |
| 5 | 4 | IBV-rNp-DSS | Coarse | 200 | 10 | 100 | 2 | |

TABLE 7-1-continued

Test group setting

| Test group | Number of chickens | Test vaccine | Administration route | Antigen concentration in vaccine stock solution (μg/mL) | Fold-dilution | Dose (μL/body · dose) | Number of times of immunization | Challenge strain |
|---|---|---|---|---|---|---|---|---|
| 6 | 4 | | spray | | 100 | | 2 | |
| 7 | 4 | | | | 1000 | | 2 | |
| 8 | 4 | | | | 10 | | 1 | |
| 9 | 4 | IBV-rNp-DSS | Fine | 200 | 10 | 100 | 2 | |
| 10 | 4 | | spray | | 100 | | 2 | |
| 11 | 4 | | | | 1000 | | 2 | |
| 12 | 4 | | | | 10 | | 1 | |
| 13 | 4 | None | — | | — | — | — | |

TABLE 7-2

Animal test schedule

| | Age in days | | | |
|---|---|---|---|---|
| Test group | 7 | 14 | 35 | 42 |
| Single-immunization groups | Immunization | — | Challenge | Autopsy |
| Two-immunization groups | Immunization | Immunization | | |
| Challenge control group | — | — | | |

(2) Evaluation Items

The following items were evaluated in the same manner as in 4.

A. Evaluation based on the tracheal ciliary movement score
B. Quantification of viral gene in organs
C. Isolation of virus from organs <Results>

(1) Animal Test

A total of 13 test groups were set up, and four birds were tested for each test group. The test vaccine was administered after up to 100-fold dilution with PBS for the nasal instillation route, or after up to 1000-fold dilution with PBS for the coarse spray or fine spray route. Administration of the test vaccine was carried out only at 7 days old in the single-immunization group; and at 7 days old and 14 days old in the two-immunization group. In the cases of the nasal instillation route, 50 μL/dose of the vaccine was administered for each bird. In the cases of the coarse spray or fine spray route, taking the amount of loss into account, 100 μL/dose of the vaccine was administered for each bird. When the administration was carried out by the coarse spray or fine spray route, each test chicken was placed in a large plastic bag, and a predetermined amount of the test vaccine was administered from about 50 cm above the test chicken toward its face. Thereafter, the mouth of the plastic bag was tied, and the plastic bag was left to stand for about 1 minute to provide an environment which allows the test chicken to efficiently inhale test vaccine particles floating in the air. In all test groups including the challenge control group, each chicken was challenged by intratracheal inoculation of 3.5 log $EID_{50}$/body (50 μL/body) of the challenge strain at 21 days old. The chickens were kept under observation of clinical symptoms, and then subjected to autopsy at Week 1 after the challenge, for collecting trachea and kidney.

(2) Evaluation Based on Tracheal Ciliary Movement Score

Figures 1, 7:
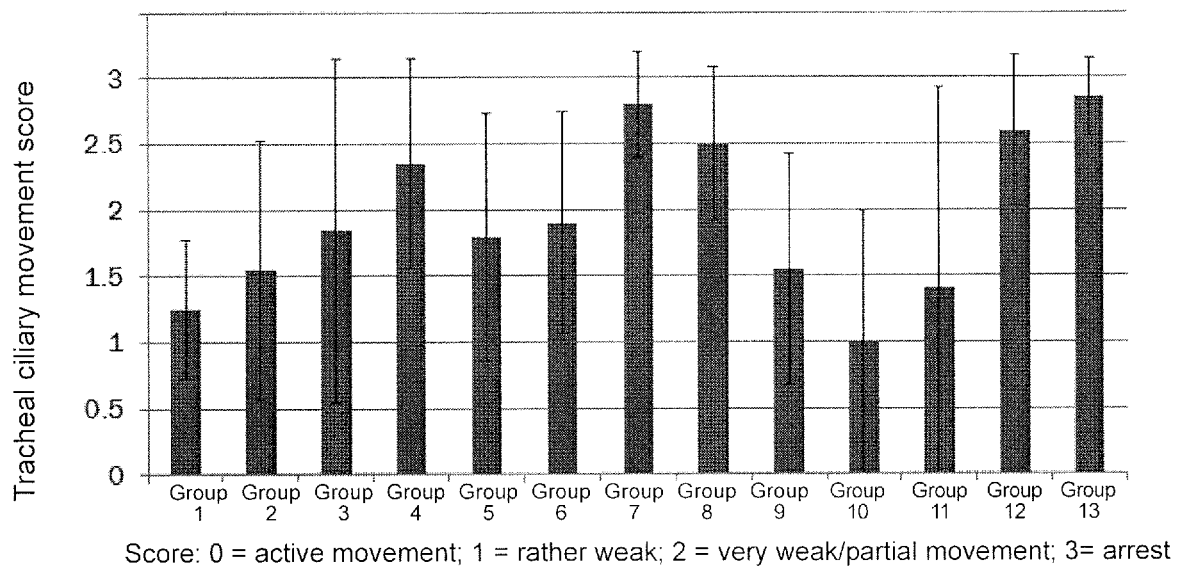
Figures 2, 7:
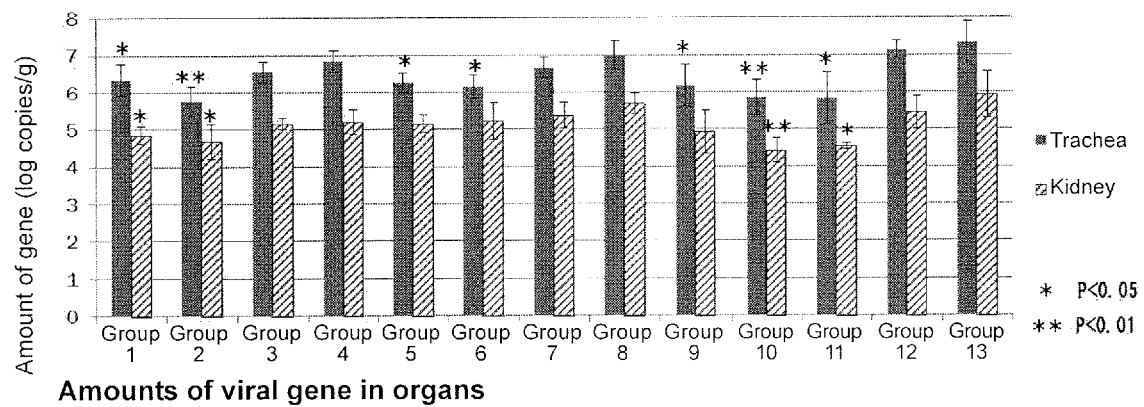
Figures 3, 7:
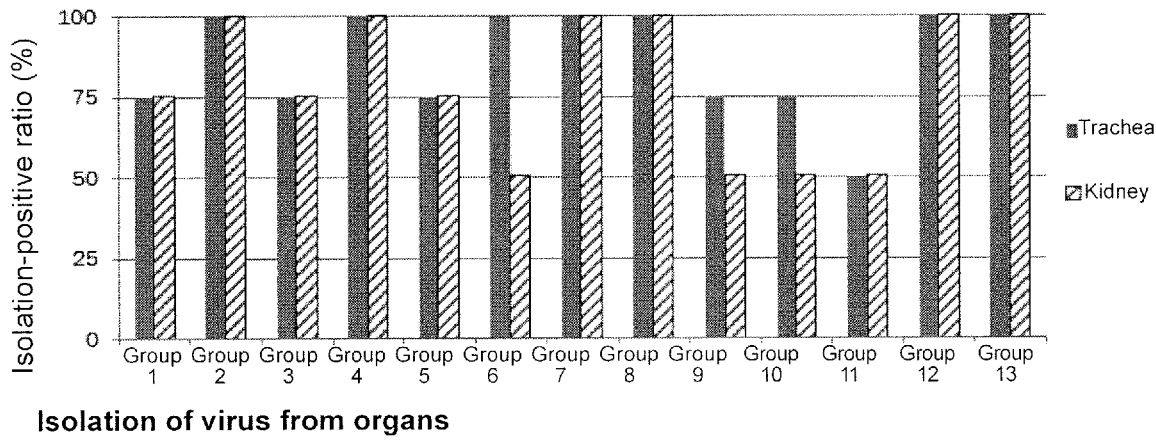

In the cases of the nasal instillation route, the two-immunization groups showed reduction of the suppression in an antigen concentration-dependent manner. However, in the single-immunization group, suppression-reducing effect was found (FIG. 7-1). In the cases of the coarse spray route, the two-immunization groups showed certain levels of reduction of the suppression at up to 100-fold dilution. However, the result obtained at 1000-fold dilution was equivalent to that in the challenge control group. In the cases of the fine spray route, the two-immunization groups showed similar average scores at up to 1000-fold dilution. Even at 1000-fold dilution, two out of the four chickens showed average scores of less than 1 (Table 7-3). Variation of the score among individuals was found also within each test group.

TABLE 7-3

Distribution of the tracheal ciliary movement score

| | Number of chickens with each score | | |
|---|---|---|---|
| Test group | 0 to less than 1 | 1 to less than 2 | 2 to less than 3 |
| Group 1 | 1 | 2 | 1 |
| Group 2 | 0 | 3 | 1 |
| Group 3 | 1 | 0 | 3 |
| Group 4 | 0 | 1 | 3 |
| Group 5 | 1 | 0 | 3 |
| Group 6 | 0 | 2 | 2 |
| Group 7 | 0 | 0 | 4 |
| Group 8 | 0 | 0 | 4 |
| Group 9 | 1 | 1 | 2 |
| Group 10 | 2 | 1 | 1 |
| Group 11 | 2 | 0 | 2 |
| Group 12 | 0 | 1 | 3 |
| Group 13 | 0 | 0 | 4 |

(3) Quantification of Viral Gene in Organs

Viral gene was detected from the organs in all immunization groups (Table 7-4). In the two-immunization groups, significant decreases in the amount of viral gene were found for the trachea and/or kidney at up to 10-fold dilution in the cases of the nasal instillation route, up to 100-fold dilution in the cases of the coarse spray route, and up to 1000-fold dilution in the cases of the fine spray route (FIG. 7-2).

TABLE 7-4

| | Positive ratio as measured by real-time PCR (%) | |
|---|---|---|
| Test group | Trachea | Kidney |
| Group 1 | 100 | 100 |
| Group 2 | 100 | 100 |
| Group 3 | 100 | 100 |
| Group 4 | 100 | 100 |
| Group 5 | 100 | 100 |
| Group 6 | 100 | 100 |
| Group 7 | 100 | 100 |
| Group 8 | 100 | 100 |
| Group 9 | 100 | 100 |
| Group 10 | 100 | 100 |
| Group 11 | 100 | 100 |
| Group 12 | 100 | 100 |
| Group 13 | 100 | 100 |

(4) Virus Isolation and Measurement of Virus Titer

In the cases of the fine spray route, the two-immunization groups showed decreased virus-isolation-positive rates from the organs even at 1000-fold dilution (FIG. 7-3). The maximum dilution factor at which a significant difference was found in the virus titer for the trachea was 10 in the cases of the nasal instillation route, and 1000 in the cases of the fine spray route. However, a large variation was found among individuals within each test group (FIG. 7-4).

<Conclusion>

It could be confirmed that spray administration also shows a certain level of effectiveness, and that fine spray administration, which is carried out with smaller particle sizes, exhibits better maintenance of the effectiveness even at higher dilution factors. However, since spray administration tended to show large variation among individuals, improvement of the immunization method was attempted.

8. Study of Antigen Region of Test Vaccine

<Object>

Surface-bound liposome vaccines are characterized in that they strongly induce cytotoxic T lymphocyte (CTL) response. However, the CTL epitope region of IBV has not yet been clarified. IBV-rNp-DSS, which is the subject of the present study, uses full-length IBV nucleocapsid (N) protein as the antigen region. However, under the assumption that an epitope may be localized in a partial region of N protein, identification of such an epitope-localized region may lead to improvement of the effectiveness of the liposome vaccine. In view of this, liposome vaccines containing, as the antigen, a fragmented N protein, or a chimeric protein prepared by binding N protein and membrane (M) protein to each other, were prepared, and their effectiveness was compared by animal tests.

<Materials and Methods>

Figures 3, 8:
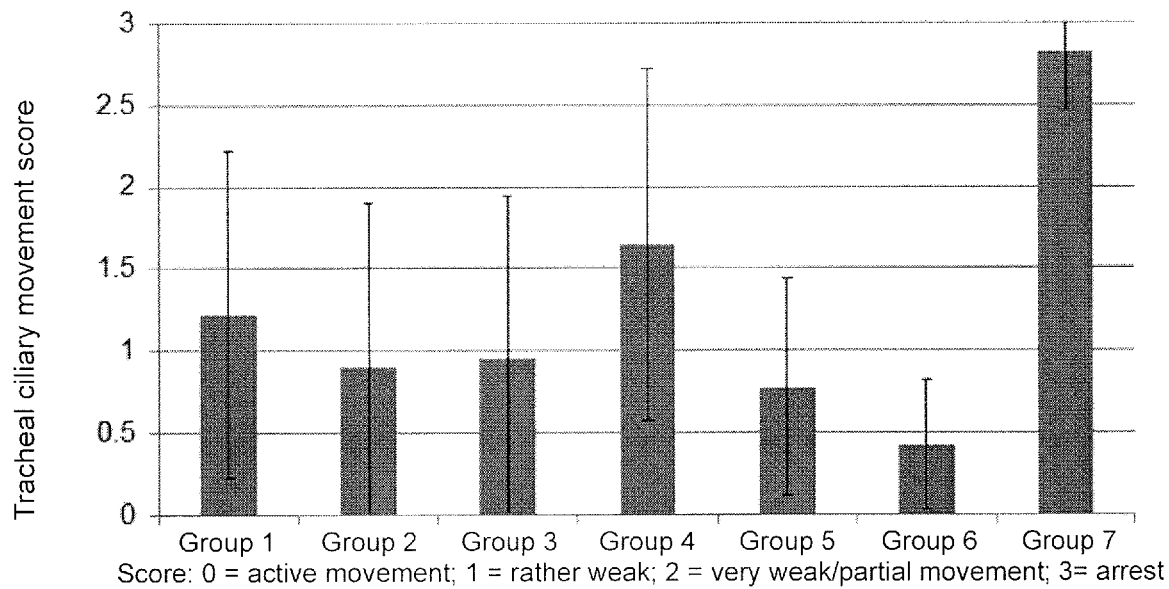
Figures 4, 8:
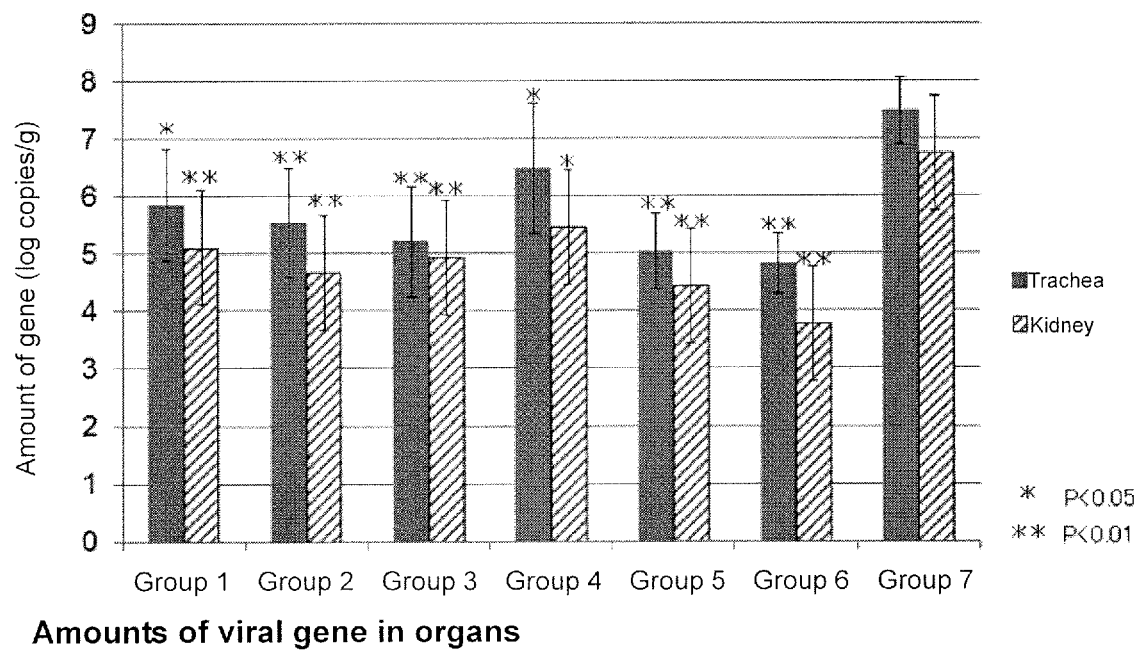

(1) Preparation of Fragmented/Chimeric Proteins and Liposome Modification Thereof The N protein gene (1230 bp, SEQ ID NO:1) of the IBV Chiba (2002) strain was divided into four parts partially overlapping with each other in both ends, and recombinant proteins were prepared therefrom using recombinant E. coli (FIG. 8-1). The amino acid sequences encoded by the base sequences N1 to N4 are shown in SEQ ID NOs:5 to 12.

In addition, regions of IBV N and M proteins, which regions are especially highly conserved among IBV strains, were bound together to prepare a chimeric protein: Ch(N+M) (FIG. 8-2). The base sequence and amino acid sequence of Ch(N+M) are shown in SEQ ID NOs:13 and 14. In the base sequence of SEQ ID NO: 3, positions 1 to 450 correspond to the N protein region: 241-690 (450 bp), and positions 451 to 657 correspond to the M protein region: 454-660 (207 bp).

These were bound to the liposome surface by the DSS method, to prepare a liposome vaccine.

(2) Animal Test

The test group setting and the test schedule were as shown in Table 8-1 and Table 8-2. At 7 days old and 14 days old, the test vaccine, 10-fold diluted with PBS, was administered to chickens by spraying (fine spray), and then the birds were challenged with a highly virulent heterologous strain. In addition, a test group in which only the challenge is carried out was set up to provide a challenge control group. The droplet particle size was adjusted using a live-vaccine power sprayer (Nyukon 607, Kimura Nosan) to 50 to 100 μm for the fine spray administration. Further, in order to reduce variation among the individuals, the administration time in each test group was increased from 4 seconds to 6 seconds while the dose of the test vaccine was the same as in the method carried out in 7.

TABLE 8-1

| | | | | Test group setting | | | | |
|---|---|---|---|---|---|---|---|---|
| Test group | Number of birds | Vaccine antigen | Administration route | Antigen concentration in vaccine stock solution (μg/mL) | Fold-dilution | Dose (μL/body/dose) | Number of times of immunization | Challenge strain |
| 1 | 8 | N1 | Fine spray | 200 | 10-fold | 100 | 2 | IBV Kagawa/2012/1 strain |
| 2 | 8 | N2 | | | | | | |
| 3 | 8 | N3 | | | | | | |
| 4 | 8 | N4 | | | | | | |
| 5 | 8 | N + M | | | | | | |
| 6 | 8 | IBV-rNp (full length) | | | | | | |
| 7 | 6 | — | — | | — | — | — | — |

TABLE 8-2

| | Test schedule | | | |
|---|---|---|---|---|
| | Age in days | | | |
| Test group | 7 | 21 | 28 | 35 |
| Immunization groups | Immunization | Immunization | Challenge | Autopsy |
| Challenge control group | — | — | | |

(3) Evaluation Items

The following items were evaluated in the same manner as in 4.

A. Evaluation based on the tracheal ciliary movement score
B. Quantification of viral gene in organs <Results>

(1) Preparation of Fragmented/Chimeric Proteins and Liposome Modification Thereof The N protein gene (1230 bp) derived from the IBV Chiba (2002) strain was divided into four parts partially overlapping with each other in both ends, and recombinant proteins were prepared therefrom using recombinant *E. coli*. The recombinant proteins were designated N1, N2, N3, and N4 in the order from the 5'-end side. In addition, regions in IBV N and M proteins, which regions are especially highly conserved among viral strains, were bound together to prepare a chimeric protein (N+M). These were bound to the liposome surface by the DSS method, to prepare a total of five kinds of liposome vaccines.

(2) Animal Test

A total of seven test groups were set up. Eight birds were tested in each of Groups 1 to 6, in which immunization with a liposome vaccine is carried out, and six birds were tested in Group 7, which is a challenge control group. In Groups 1 to 6, a liposome vaccine prepared in (1) was 10-fold diluted with PBS, and 100 μL per body of the diluted vaccine was administered by fine spraying (droplet particle size, 50 to 100 μm) at 7 days old and 21 days old using a live-vaccine power sprayer. In all test groups including the challenge control group, each bird was challenged by intratracheal inoculation of 3.5 log $EID_{50}$/body (50 μL/body) of a highly virulent heterologous strain at 28 days old. The birds were kept under observation of clinical symptoms, and then subjected to autopsy at Week 1 after the challenge, for collecting trachea and kidney.

(3) Evaluation Based on Tracheal Ciliary Movement Score

Compared to the challenge control group, all test groups tended to show reduced suppression of the tracheal ciliary movement (FIG. 8-3). In Group 6, (IBV-rNp), in which the highest suppression-reducing effect was found, showed less variation among individuals, and all birds had scores of not more than 1 (Table 8-3). In other test groups, some birds had scores higher than 1, and variation of the score was found among individuals within each test group. Among Groups 1 to 4, in which fragmented N proteins were used, Group 2 and Group 3 tended to show low scores.

TABLE 8-3

Distribution of the tracheal ciliary movement score

| Test group | Number of birds with each score | | |
|---|---|---|---|
| | 0 to less than 1 | 1 to less than 2 | 2 to less than 3 |
| Group 1 | 2 | 4 | 2 |
| Group 2 | 5 | 1 | 2 |
| Group 3 | 4 | 3 | 1 |
| Group 4 | 2 | 2 | 4 |
| Group 5 | 5 | 2 | 1 |
| Group 6 | 7 | 1 | 0 |
| Group 7 | 0 | 0 | 8 |

(4) Quantification of Viral Gene in Organs

Compared to the challenge control group, all test groups showed significantly smaller amounts of viral gene in the trachea and kidney (FIG. 8-4). The highest gene-amount-reducing effect was found in Group 6 (BV-rNp), and the next highest effect was found in Group 5 (N+M). Among Groups 1 to 4, in which the fragmented IBV N proteins were used, Group 2 and Group 3 tended to show smaller amounts of gene.

<Conclusion>

The fragmented or chimeric liposome vaccines showed certain levels of symptom onset-reducing effect against the challenges with the highly virulent heterologous strain. The effectiveness tended to be high in the N2 and N3 regions, but evident localization of the epitope region could not be identified. The test group using the full length (IBV-rNp) as the antigen, which has been studied above, showed a higher symptom onset-reducing effect.

Due to the partial modification of the fine spray administration method, the variation among individuals was reduced, and the symptom onset-reducing effect was improved.

9. Study of Test Vaccine Administration Method (2)

<Object>

The minimum effective amount of antigen in fine spray administration was studied for IBV-rNp.

<Materials and Methods>

(1) Animal Test

The test group setting and the test schedule were as shown in Table 9-1 and Table 9-2. From 2 μg/dose/body in terms of the amount of IBV-rNp antigen, IBV-rNp-DSS was 2-fold serially diluted with PBS, and administered at 7 days old and 21 days old by fine spraying to perform immunization. A challenge was carried out at 28 days old, and autopsy was carried out at 35 days old. In addition, a test group in which only the challenge is carried out was set up to provide a challenge control group.

TABLE 9-1

Test group setting

| Test group | Number of birds | Vaccine antigen | Administration route | Amount of rNp antigen (μg/dose/body) | Dose (μL/body/dose) | Number of times of immunization | Challenge strain |
|---|---|---|---|---|---|---|---|
| 1 | 5 | IBV-rNp-DSS | Fine spray | 2 | 100 | 2 | Kagawa/2012/1 strain |
| 2 | 5 | | | 1 | | | |
| 3 | 5 | | | 0.5 | | | |
| 4 | 5 | | | 0.25 | | | |
| 5 | 5 | | | 0.125 | | | |
| 6 | 5 | | | 0.0625 | | | |
| 7 | 5 | | | 0.03125 | | | |
| 8 | 5 | None | | — | | — | |

TABLE 9-2

Animal test schedule

| Test group | Age in days | | | |
|---|---|---|---|---|
| | 7 | 21 | 28 | 35 |
| Immunization groups (Groups 1 to 7) | Immunization | Immunization | Challenge | Autopsy |
| Challenge control group (Group 8) | — | — | | |

(2) Evaluation Items

The following items were evaluated in the same manner as in 4.

A. Evaluation based on the tracheal ciliary movement score

B. Quantification of viral gene in organs

<Results>

(1) Animal Test

A total of seven test groups were set up. Eight birds were tested in each of Groups 1 to 6, in which immunization with a liposome vaccine is carried out, and six birds were tested in Group 7, which is a challenge control group. In Groups 1 to 6, a liposome vaccine prepared in (1) was 10-fold diluted with PBS, and 100 μL per body of the diluted vaccine was administered by fine spraying (droplet particle size, 50 to 100 μm) at 7 days old and 21 days old using a live-vaccine power sprayer. In all test groups including the challenge control group, each bird was challenged by intratracheal inoculation of 3.5 log $EID_{50}$/body (50 μL/body) of a highly virulent heterologous strain at 28 days old. The birds were kept under observation of clinical symptoms, and then subjected to autopsy at Week 1 after the challenge, for collecting trachea and kidney.

(2) Evaluation Based on Tracheal Ciliary Movement Score

Figures 1, 9:
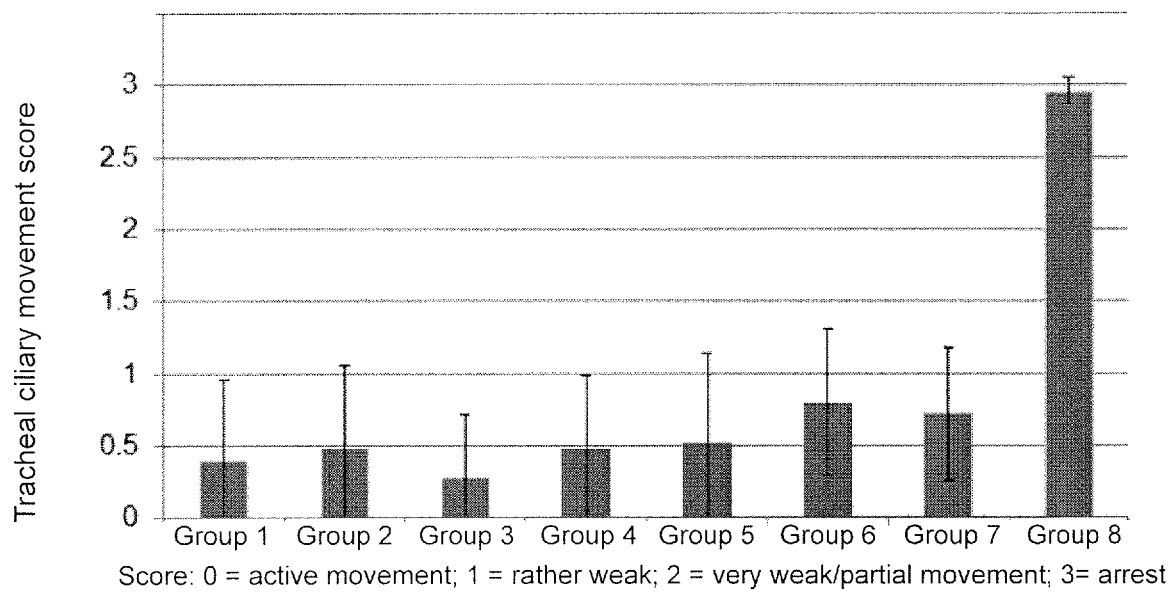
Figures 2, 9:
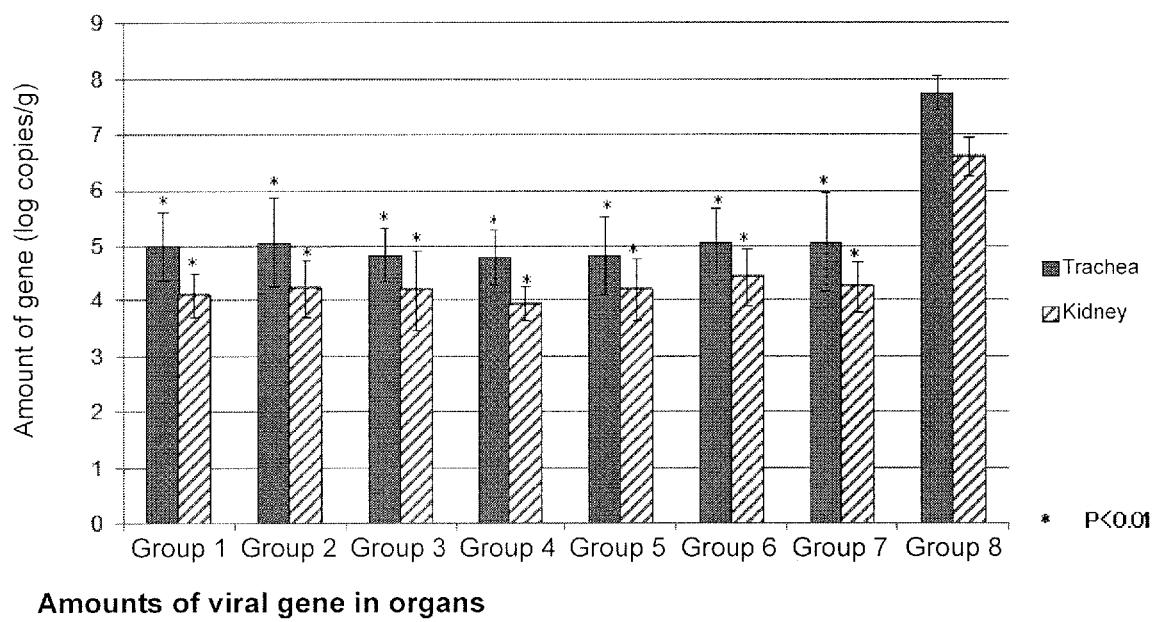

Compared to the challenge control group, all test groups tended to show reduced suppression of the tracheal ciliary movement (FIG. 9-1). The differences in the score among the test groups were small, and there were no birds showing a score of 2 or more in any of the test groups (Table 9-3). Also in the test group with the smallest amount of antigen (Group 7), variation among the individuals was small.

TABLE 9-3

Distribution of the tracheal ciliary movement score

| Test group | Number of birds with each score | | |
|---|---|---|---|
| | 0 to less than 1 | 1 to less than 2 | 2 to less than 3 |
| Group 1 | 4 | 1 | 0 |
| Group 2 | 4 | 1 | 0 |
| Group 3 | 4 | 1 | 0 |
| Group 4 | 3 | 2 | 0 |
| Group 5 | 4 | 1 | 0 |
| Group 6 | 3 | 2 | 0 |
| Group 7 | 3 | 2 | 0 |
| Group 8 | 0 | 0 | 5 |

(3) Quantification of Viral Gene in Organs

Compared to the challenge control group, all test groups showed significantly smaller amounts of viral gene in the trachea and kidney (FIG. 9-2).

<Conclusion>

Since a high symptom onset-reducing effect was found even after the maximum, 640-fold, dilution of the IBV-rNp-DSS stock solution (20 μg/mL), it was suggested that the minimum effective amount of antigen in two-time administration of IBV-rNp-DSS by fine spraying corresponds to 640- or higher-fold dilution of the stock solution.

10. Study on Effectiveness of Liposome Vaccine in Relation to Presence or Absence of Binding between Antigen and Liposome <Object>

According to a past literature using mice (Taneichi et al., J Immunol. 2006, 177(4):2324-2330), it has been suggested that surface-bound liposome vaccines are required to be in a state where an antigen is bound to the liposome surface, in order to realize their effectiveness. However, no study has yet been carried out on whether this applies to chickens. In view of this, comparison with cases where the antigen or liposome is used alone, or where the antigen and liposome are not bound to each other, was carried out to clarify that binding of the antigen to the liposome is indispensable for realization of the effectiveness.

<Materials and Methods>

(1) Animal Test

The test group setting and the test schedule were as shown in Table 10-1 and Table 10-2. Using IBV-rNp-DSS as a positive control, the antigen/liposome alone, or a liposome-antigen mixture in an unbound state prepared by mixing the antigen and liposome together immediately before the administration, was administered by fine spraying.

TABLE 10-1

Test group setting

| Test group | Number of chickens | Immunization material | Administration route | Amount of IBV-rNp antigen (μg/dose/body) | Dose (μL/body/dose) | Number of times of immunization | Challenge strain |
|---|---|---|---|---|---|---|---|
| Group 1 | 5 | IBV-rNp-DSS | Fine spray | 2 | 100 | 2 | Kagawa/2012/1 strain |
| Group 2 | 5 | IBV-rNp only | | 2 | | | |
| Group 3 | 5 | IBV-rNp + liposome (unbound) | | 2 | | | |
| Group 4 | 5 | Liposome only | | 0 | | | |
| Group 5 | 5 | None | | — | | — | — |

TABLE 10-2

Animal test schedule

| Test group | Age in days | | | |
|---|---|---|---|---|
| | 7 | 21 | 28 | 35 |
| Immunization groups (Groups 1 to 4) | Immunization | Immunization | Challenge | Autopsy |
| Challenge control group (Group 5) | — | — | | |

(2) Evaluation Items

The following items were evaluated in the same manner as in 4.

A. Evaluation based on the tracheal ciliary movement score
B. Quantification of viral gene in organs <Results>

(1) Animal Test

A total of four test groups were set up, and five chickens were tested for each test group. In groups 1, 2, and 3, the amount of rNp antigen was adjusted to 2 μg/dose/body with PBS. In Group 4, the amount of liposome was set to the same amount as in Group 1. Using a live-vaccine power sprayer, 100 μL per body of the vaccine was administered by fine spraying (droplet particle size, 50 to 100 μm) at 7 days old and 21 days old. In all test groups including the challenge control group, each chicken was challenged by intratracheal inoculation of 50 μL of 3.5 log $EID_{50}$/body of the Kagawa/2012/1 strain (highly virulent heterologous strain) at 28 days old. The chickens were kept under observation of clinical symptoms, and then subjected to autopsy at Week 1 after the challenge, for collecting trachea and kidney.

(2) Evaluation Based on Tracheal Ciliary Movement Score

Compared to the challenge control group. Group 1 tended to show reduced suppression of the tracheal ciliary movement. However, in Groups 2, 3, and 4, the tracheal ciliary movement score was similar to that in the challenge control group, showing no symptom onset-reducing effect (FIG. 10-1. Table 10-3).

TABLE 10-3

Distribution of the tracheal ciliary movement score

| Test group | Number of chickens with each score | | |
|---|---|---|---|
| | 0 to less than 1 | 1 to less than 2 | 2 to less than 3 |
| Group 1 | 4 | 1 | 0 |
| Group 2 | 0 | 0 | 5 |
| Group 3 | 0 | 1 | 4 |
| Group 4 | 0 | 0 | 5 |
| Group 5 | 0 | 0 | 5 |

(3) Quantification of Viral Gene in Organs

Figures 1, 10:
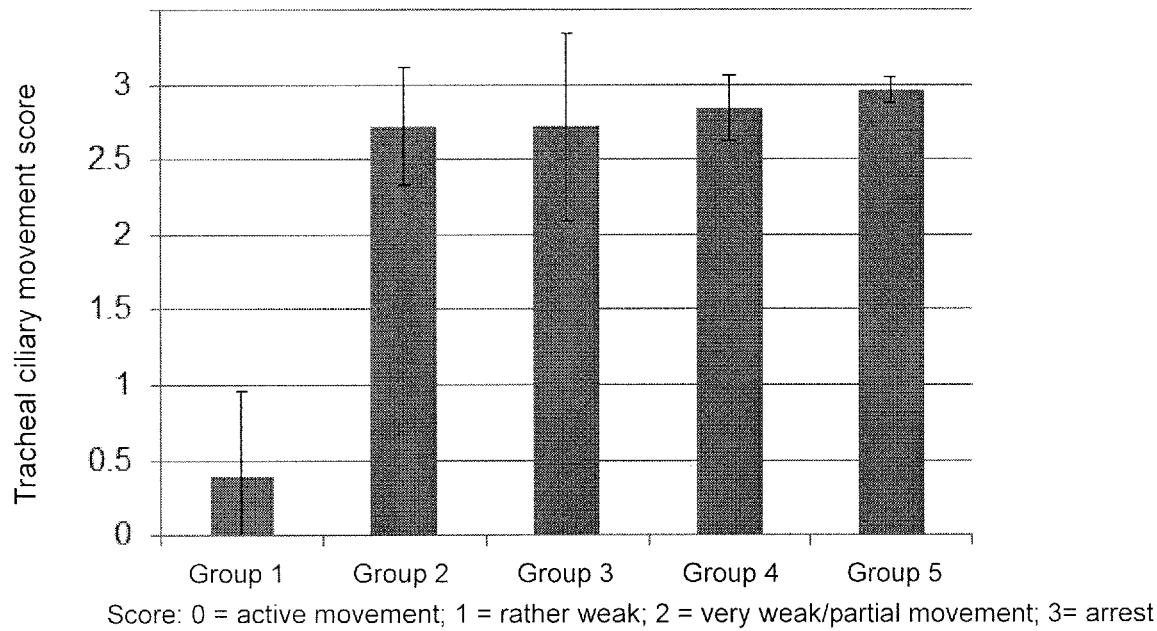
Figures 2, 10:
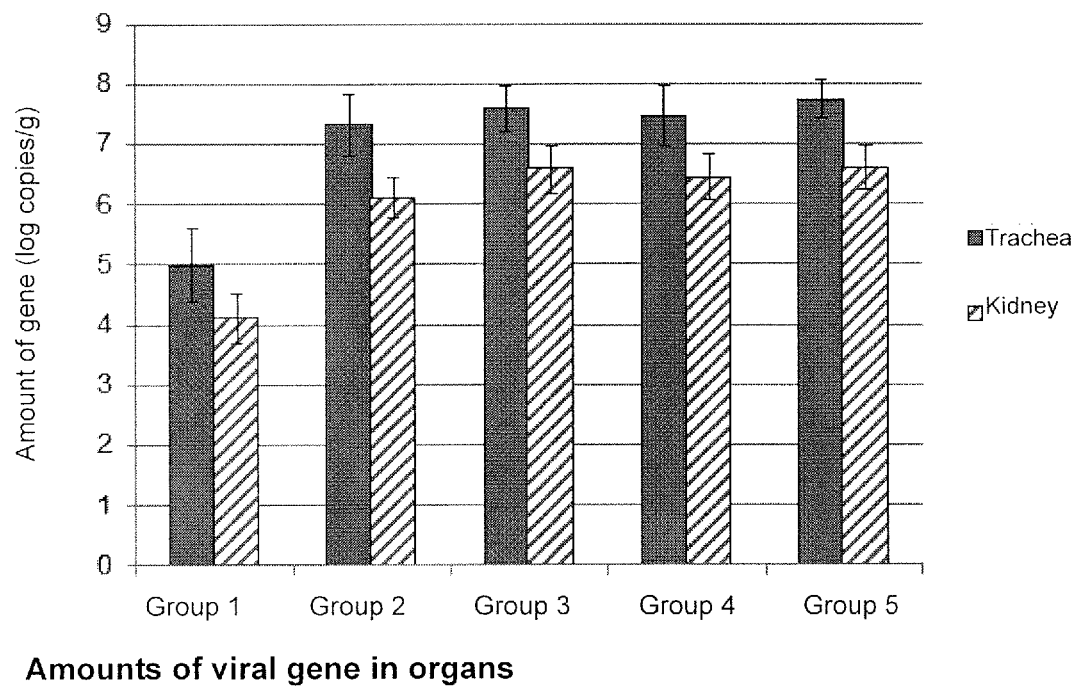

Compared to the challenge control group, Group 1 showed significantly smaller amounts of viral gene in the trachea and kidney. However, in Groups 2, 3, and 4, the amounts were similar to those in the challenge control group (FIG. 10-2).

<Conclusion>

It was confirmed that, for realization of the effectiveness of a surface-bound liposome vaccine, binding of the antigen to the liposome is indispensable also in chickens.

11. Study of Test Vaccine Administration Method (3)

<Object>

Assuming use in outdoor farms, conditions for the fine spray administration were studied.

<Materials and Methods>

(1) Animal Test

The test group setting and the test schedule were as shown in Table 11-1 and Table 11-2. In Group 1 (closed space), 10 SPF chicks were placed in a thick plastic bag (W 900×H 1000; capacity, 90 L), and rNp-DSS was administered by fine spraying from about 50 cm above the chicks toward their heads. In Groups 2 to 6 (open space), 10 SPF chicks were placed in a chicken transportation basket (internal dimension, W 750×D 500×H 280) (placement density, 0.038 $m^2$/individual), and IBV-rNp-DSS was administered by fine spraying from about 50 cm above the chicks toward their heads. For the fine spray administration, a live-vaccine power sprayer (Nyukon 607) was used. After the fine spray administration, the chicks were transferred into chicken isolators, and reared. In addition, a test group in which only the challenge is carried out was set up to provide a challenge control group (Group 7).

TABLE 11-1

Test group setting

| Test group | Number of chicks | Test vaccine | Administration route | Number of times of immunization | IBV-rNp antigen concentration (μg/mL) | Dose (μL/body/dose) | Administration time (seconds/group) | Condition of chickens during fine spray administration | Challenge strain (genotype) |
|---|---|---|---|---|---|---|---|---|---|
| 1 | 10 | IBV-rNp-DSS | Fine spray | 2 | 5 | 100 | 6 | Closed space | Kagawa/2012/1 strain (JP-IV) |
| 2 | 10 | | | | 5 | 100 | 6 | Open space | |
| 3 | 10 | | | | 20 | 100 | 6 | Open space | |
| 4 | 10 | | | | 5 | 400 | 6 | Open space | |
| 5 | 10 | | | | 5 | 100 | 30 | Open space | |
| 6 | 10 | | | | 20 | 400 | 30 | Open space | |
| 7 | 5 | None | — | — | — | — | — | — | — |

TABLE 11-2

Animal test schedule

| Test group | Age in days | | | |
|---|---|---|---|---|
| | 7 | 21 | 28 | 35 |
| Immunization groups (Groups 1 to 6) | Immunization | Immunization | Challenge | Autopsy |
| Challenge control group (Group 7) | — | — | | |

At 7 days old and 21 days old, immunization was carried out by the above method, and each chicken was challenged by intratracheal inoculation of 3.5 log $EID_{50}$ (50 µL/body) of a highly virulent heterologous strain at 28 days old. The chickens were kept under observation of clinical symptoms, and then subjected to autopsy on Day 35 for collecting trachea and kidney.

(2) Evaluation Items

A. Evaluation Based on Tracheal Ciliary Movement Score

See 4. A significance test was carried out by the Dunnett's multiple comparison test method.

B. Quantification of Viral Gene in Organs

See 4. A significance test was carried out by the Student-t test method.

<Results>

(1) Evaluation Based on Tracheal Ciliary Movement Score

Figures 1, 11:
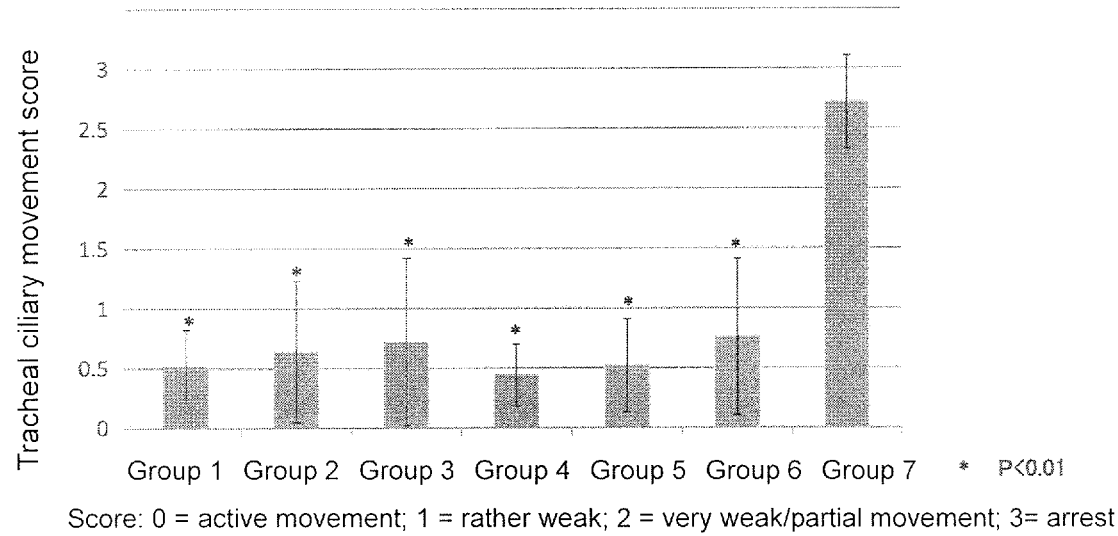
Figures 2, 11:
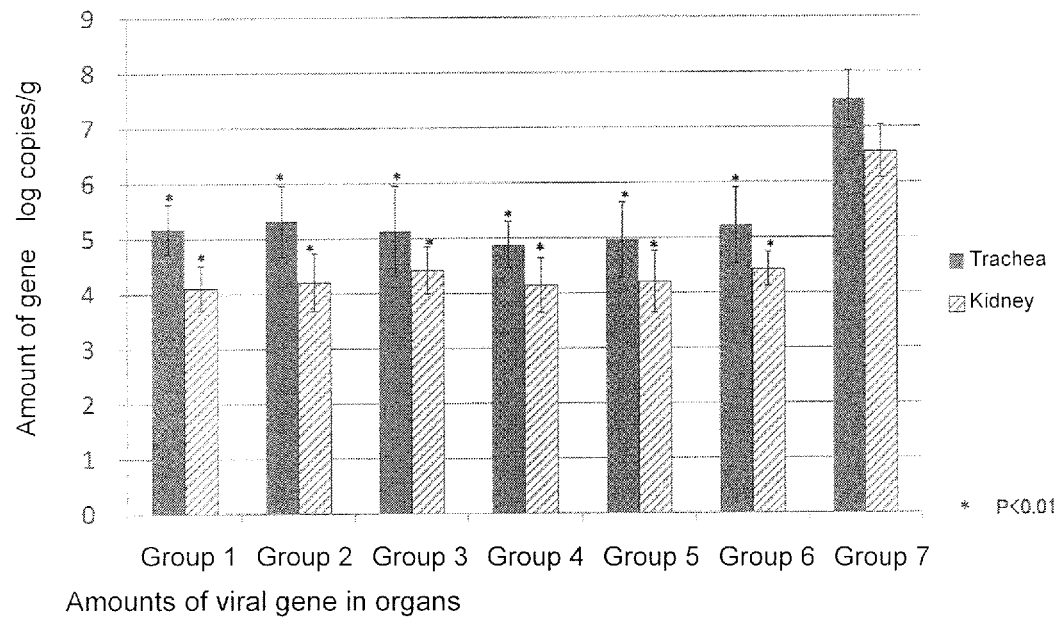

Compared to the challenge control group (Group 7), all test groups showed significantly lower tracheal ciliary movement scores (P<0.01) (FIG. 11-1). Comparison between the closed environment (Group 1) and the open environment (Group 2) was carried out under the same conditions of antigen concentration, dose, and administration time. As a result, these groups showed similar average scores, but Group 2 showed a larger variation within the test group. Compared to Group 2, the dose was increased in Group 4, and the administration time was increased in Group 5. Although Groups 4 and 5 showed average scores similar to that in Group 2, they showed a smaller variation within each test group. In all immunization groups (Groups 1 to 6), each of 7 to 9 chickens out of the 10 chickens showed a score of less than 1, and there were no chickens with a score of 2 or more (Table 11-3).

TABLE 11-3

Score distribution of the tracheal ciliary movement score

| | Number of chickens with each score | | |
|---|---|---|---|
| Test group | 0 to less than 1 | 1 to less than 2 | 2 or more |
| Group 1 | 8 | 2 | 0 |
| Group 2 | 8 | 2 | 0 |
| Group 3 | 7 | 3 | 0 |
| Group 4 | 9 | 1 | 0 |
| Group 5 | 8 | 2 | 0 |
| Group 6 | 8 | 2 | 0 |
| Group 7 | 0 | 0 | 5 |

(2) Quantification of Viral Gene in Organs

Compared to the challenge control group (Group 7), all immunization groups (Groups 1 to 6) showed significantly smaller amounts of viral gene in the trachea and kidney (P<0.01). The immunization groups (Groups 1 to 6) showed similar amounts of viral gene therebetween (FIG. 11-2).

<Conclusion>

Fine spray administration of IBV-rNp-DSS was found to be effective to the same extent between the closed environment and the open environment. It was also suggested that variation among individuals can be effectively reduced by increasing the dose of IBV-rNp-DSS per body or by increasing the administration time.

12. Study of Test Vaccine Administration Method (4)

<Object>

Conditions of fine spray administration of BV-rNp-DSS were studied in terms of the timing of administration, administration interval, and dose.

<Materials and Methods>

(1) Animal Test

The test group setting and the test schedule were as shown in Table 12-1 and Table 12-2. In the immunization groups, five SPF chicks were placed in a chicken transportation basket (internal dimension, W 750×D 500×H 280) (placement density, 0.076 m²/individual), and IBV-rNp-DSS was administered by fine spraying from about 50 cm above the chicks toward their heads. For the fine spray administration, a live-vaccine power sprayer (Nyukon 607) was used. After the fine spray administration, the chicks were transferred into chicken isolators, and reared. In addition, test groups in which only the challenge is carried out were set up to provide challenge control groups (Groups 4, 8, and 12). In the immunization groups, immunization was carried out twice at the ages in days shown in Table 1, and, 7 days after the second immunization, each chicken was challenged by intratracheal inoculation of 3.5 log $EID_{50}$ (50 µL/body) of a highly virulent heterologous strain. The chickens were kept under observation of clinical symptoms, and then subjected to autopsy on Day 7 after the challenge, for collecting trachea and kidney.

TABLE 12-1

Test group setting

| Test group | Number of chicks | Administration method | Number of times of immunization | Age in days upon administration (interval) | Age in days upon challenge | Amount of antigen (ng/dose) | Antigen concentration (ng/µL) | Dose (µL/dose) | Administration time (seconds/group) |
|---|---|---|---|---|---|---|---|---|---|
| 1 | 5 | Fine spray (particle size: 50 to 100 µm) | 2 | 0.7 (7) | 14 | 400 | 1 | 400 | 5 |
| 2 | 5 | | | | | 100 | | 100 | |
| 3 | 5 | | | | | 25 | | 25 | |
| 4 | 5 | | — | — | | — | — | — | |
| 5 | 5 | | 2 | 0.14 (14) | 21 | 400 | 1 | 400 | |
| 6 | 5 | | | | | 100 | | 100 | |

TABLE 12-1-continued

Test group setting

| Test group | Number of chicks | Administration method | Number of times of immunization | Age in days upon administration (interval) | Age in days upon challenge | Amount of antigen (ng/dose) | Antigen concentration (ng/μL) | Dose (μL/dose) | Administration time (seconds/group) |
|---|---|---|---|---|---|---|---|---|---|
| 7 | 5 | | | | | 25 | | 25 | |
| 8 | 5 | | — | — | | — | | — | |
| 9 | 5 | | 2 | 7.21 | 28 | 400 | 1 | 400 | |
| 10 | 5 | | | (14) | | 100 | | 100 | |
| 11 | 5 | | | | | 25 | | 25 | |
| 12 | 5 | | — | — | | — | | — | |

TABLE 12-2

Animal test schedule

| Test group | Age in days | | | | | |
|---|---|---|---|---|---|---|
| | 0 | 7 | 14 | 21 | 28 | 35 |
| Groups 1 to 3 | Immunization | Immunization | Challenge | | Autopsy | |
| Group 4 | — | — | | | | |
| Groups 5 to 7 | Immunization | | Immunization | | Challenge | Autopsy |
| Group 8 | — | | — | | | |
| Groups 9 to 11 | | Immunization | | Immunization | Challenge | Autopsy |
| Group 12 | | — | | — | | |

(2) Evaluation Items

A. Evaluation Based on the Tracheal Ciliary Movement Score

See 4. A significance test was carried out by the Dunnett's multiple comparison test method.

B. Quantification of Viral Gene in Organs

See 4. A significance test was carried out by the Student-t test method.

<Results>

(1) Evaluation Based on Tracheal Ciliary Movement Score

Figures 1, 12:
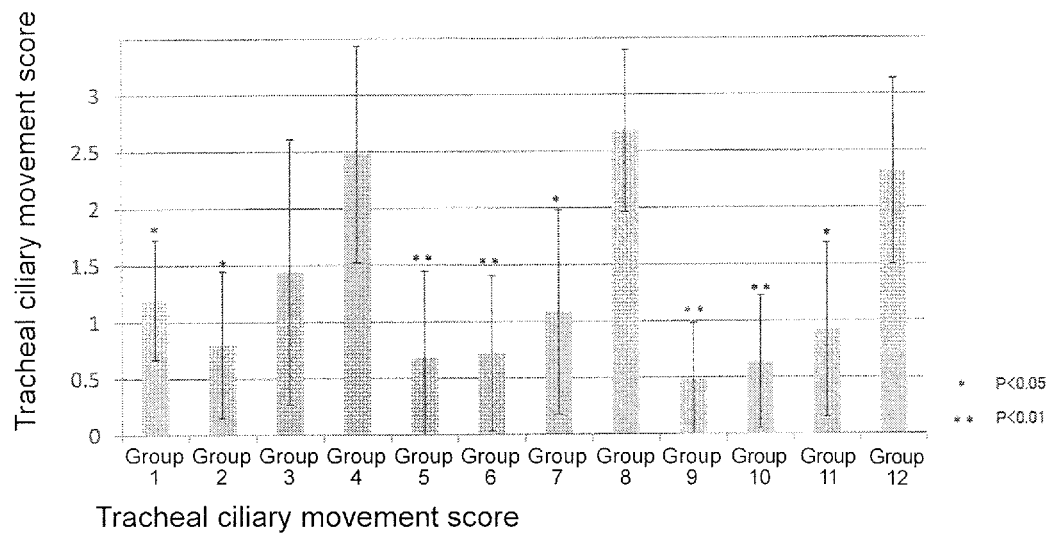
Figures 2, 12:
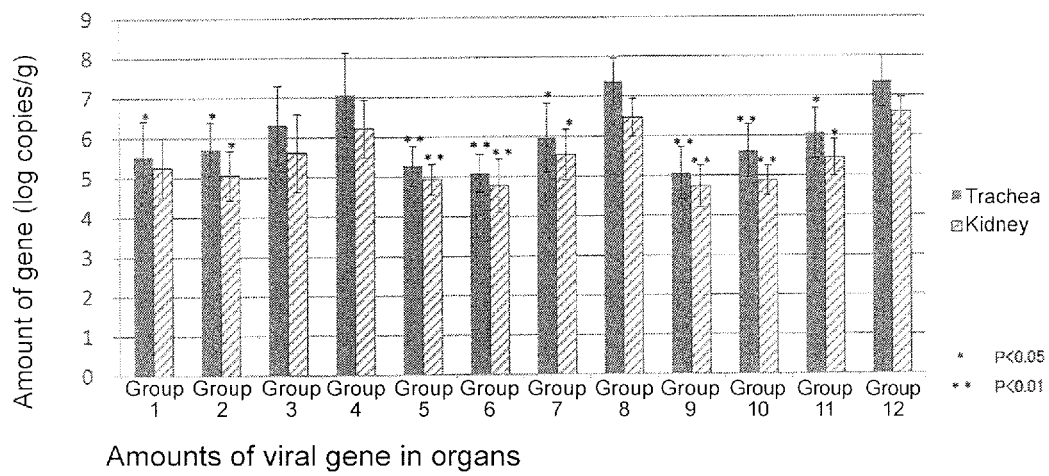

Compared to the challenge control group, significant decreases in the tracheal ciliary movement score (P<0.01 or P<0.05) were found in the 0- to 7-day-old immunization groups (Groups 1 and 2), the 0- to 14-day-old immunization groups (Groups 5 and 6), and the 7- to 21-day-old immunization groups (Groups 9 and 10), which were the groups in which the amount of antigen was not less than 100 ng/dose (FIG. 12-1). On the other hand, when the amount of antigen was 25 ng/dose (Groups 3, 7, and 11), significant decreases in the tracheal ciliary movement score were found only in Group 7 and Group 11, which were the groups in which the administration interval was 14 days (P<0.05). The variation of the tracheal ciliary movement score within each test group tended to be slightly large in the 0- to 7-day-old immunization groups (Groups 1 to 3), and, irrespective of the timing of administration, in the immunization groups in which the amount of antigen was 25 ng/dose (Groups 3, 7, and 11) (Table 12-3).

TABLE 12-3

Score distribution of the tracheal ciliary movement score

| Test group | Number of chickens with each score | | |
|---|---|---|---|
| | 0 to less than 1 | 1 to less than 2 | 2 or more |
| Group 1 | 1 | 3 | 1 |
| Group 2 | 4 | 1 | 0 |
| Group 3 | 1 | 2 | 2 |
| Group 4 | 1 | 0 | 4 |
| Group 5 | 4 | 0 | 1 |
| Group 6 | 3 | 2 | 0 |
| Group 7 | 2 | 2 | 1 |
| Group 8 | 0 | 1 | 4 |
| Group 9 | 3 | 2 | 0 |
| Group 10 | 2 | 3 | 0 |
| Group 11 | 2 | 2 | 1 |
| Group 12 | 0 | 1 | 4 |

(2) Quantification of Viral Gene in Organs

The results are shown in FIG. 12-2. Compared to the challenge control group, significant decreases in the amount of viral gene in the trachea were found in the immunization groups in which the amount of antigen was not less than 100 ng/dose (Groups 1 and 2, 5 and 6, and 9 and 10) (P<0.01 or P<0.05). On the other hand, significant decreases in the amount of viral gene in the kidney were found in the immunization groups in which the amount of antigen was not less than 100 ng/dose except for Group 1 (Groups 2, 5 and 6, and 9 and 10) (P<0.01 or P<0.05).

<Conclusion>

Concerning the optimum conditions of fine spray administration of IBV-rNp-DSS, high symptom onset-reducing effects were found when the timing of the first administration was 0 day old or 7 days old; the administration interval was 14 days; and the amount of antigen was not less than 100 ng/dose. Since IBV is widespread in the environment, it is important to give immunity against this disease to chicks at an early stage. It was thus thought that the condition "two-time administration by administration at 0 day old and 14 days old at 100 ng/dose in terms of the amount of antigen" is suitable as an IBV-rNp-DSS administration model.

13. Evaluation of Effectiveness of Test Vaccines (4)

<Object>

Effectiveness of IBV-rNp-DSS against abnormalities in egg laying due to IBV infection was evaluated.

<Materials and Methods>

(1) Animal Test

The test group setting and the test schedule were as shown in Table 13-1 and Table 13-2. Twelve 25-week-old SPF egg-laying chickens in each group were tested. The chickens were reared in separate cages (H 965×W 393×D 193 mm) for about 11 weeks. In the vaccine test group, IBV-rNp-DSS was administered by fine spraying (0.5 µg/100 µL/individual) at 25 weeks old and 27 weeks old. At 28 weeks old, that is, 1 week after the booster immunization, the vaccine test group and the challenge control group were challenged by intratracheal inoculation of 3.5 log $EID_{50}$ (50 µL/body) of a highly virulent heterologous strain. The chickens were kept under observation of clinical symptoms and the egg-laying performance while buccal swabs, cloacal swabs, and sera were collected over time. Two chickens in each group on Day 7 after the challenge, and 10 chickens in each group on Day 57 after the challenge, were subjected to autopsy, to collect organs (trachea, kidney, and oviduct).

TABLE 13-1

Test group setting

| Test group | | Number of chickens | Immunization | Challenge |
|---|---|---|---|---|
| Group 1 | Uninfected control group | 12 | Not done | Not done |
| Group 2 | Vaccine test group | 12 | Done | Done |
| Group 3 | Challenge control group | 12 | Not done | Done |

TABLE 13-2

Test schedule

| | 0 | 14 | 21 | 28 | 57 | (dPI) |
|---|---|---|---|---|---|---|
| Group 1 | | | | Autopsy (2 chickens/group) | Autopsy (10 chickens/group) | |
| Group 2 | Immunization | Immunization | Challenge | | | |
| Group 3 | | | | | | |

(2) Evaluation Items

A. Evaluation of Egg-Laying Performance

The egg-laying performance of each chicken was recorded every day (−7 to 57 dPI). In cases where an abnormal egg was found, the presence or absence of abnormality of the external egg quality and internal egg quality was investigated.

B. Quantification of Viral Gene

For each individual, quantification of IBV gene was carried out by real-time PCR for the buccal and cloacal swabs at 7, 14, 35, and 57 dPI, and for the trachea, kidney, and oviduct (ampulla) collected by the autopsies at 7 and 57 dPI. A significance test was carried out by the Student-t test.

C. Tracheal Ciliary Movement Score

In the autopsies at 7 dPI and 57 dPI, tracheal ciliary movement was observed for tracheal rings at five sites per individual under the microscope, and scoring was carried out according to the following index (0=active movement; 1=rather weak; 2=very weak/partial movement; 3=arrest).

D. Antibody Test (ELISA)

Using a commercially available IB ELISA kit (IDEXX), the ELISA antibody titer (S/P ratio) was measured for the sera at 0, 7, and 57 dPI from each chicken, and the average value was calculated for each test group. A significance test was carried out by the Student-t test.

<Results>

(1) Evaluation of Egg-Laying Performance

Figures 1, 13:
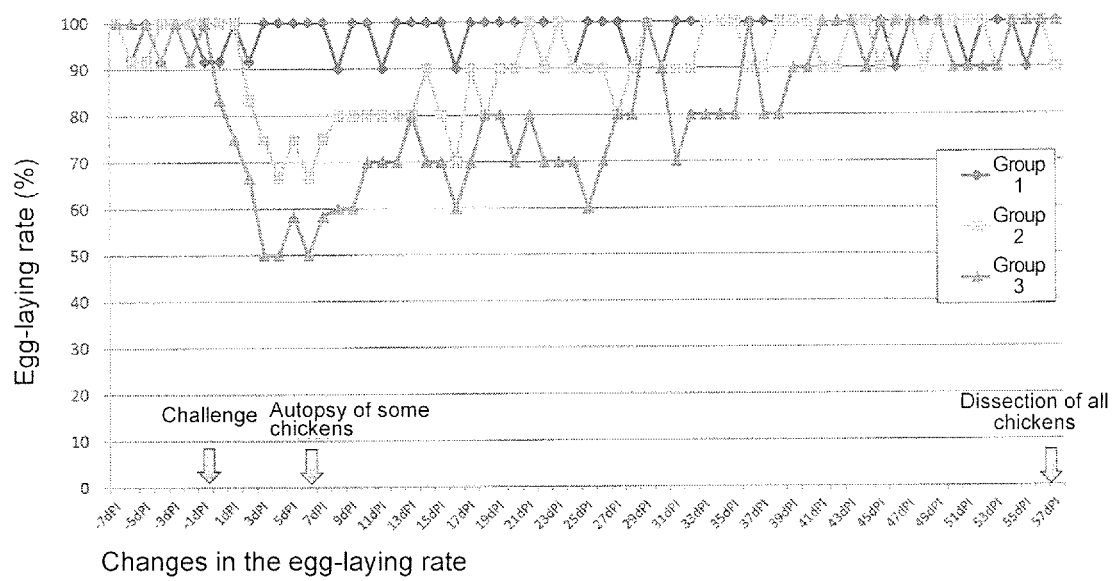
Figures 2, 13:
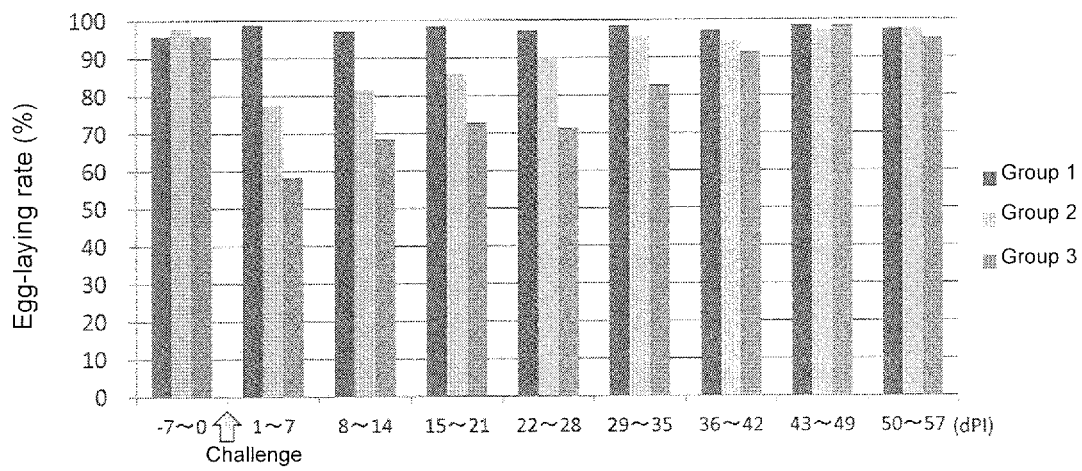
Figures 3, 13:
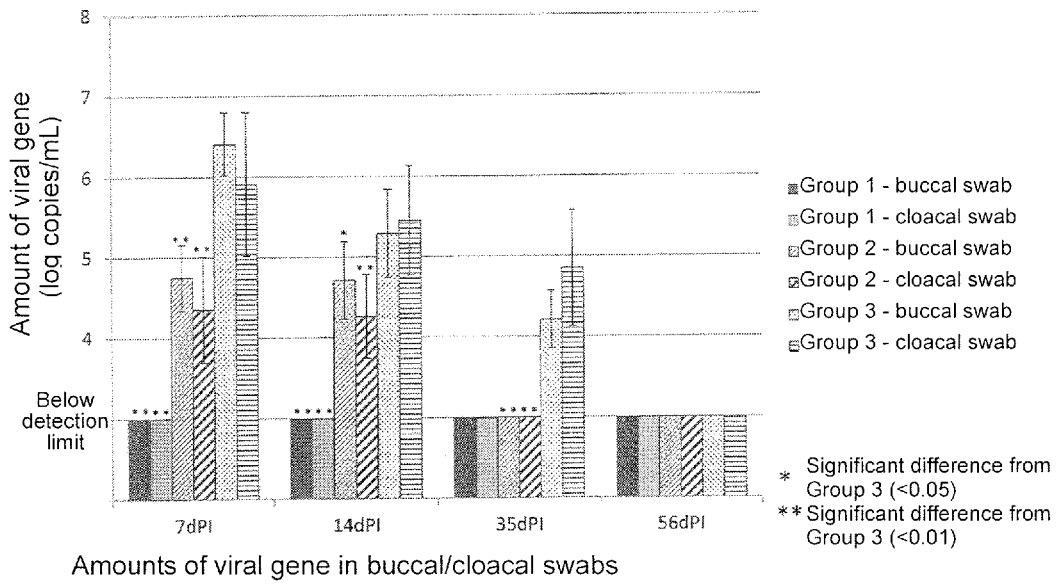
Figures 4, 13:
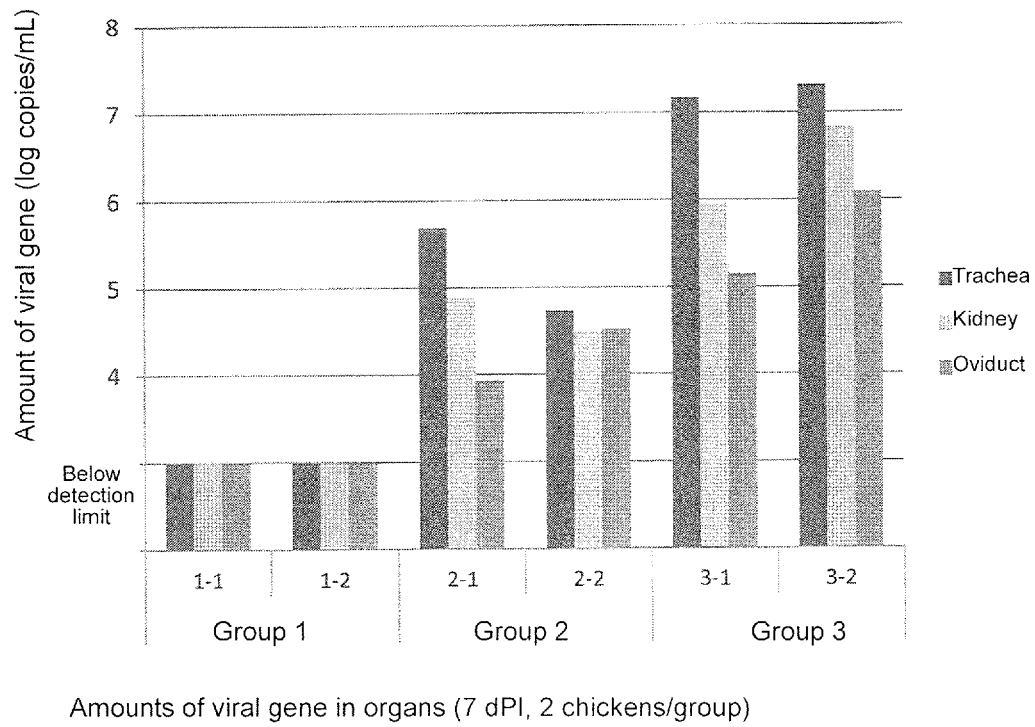
Figures 5, 13:
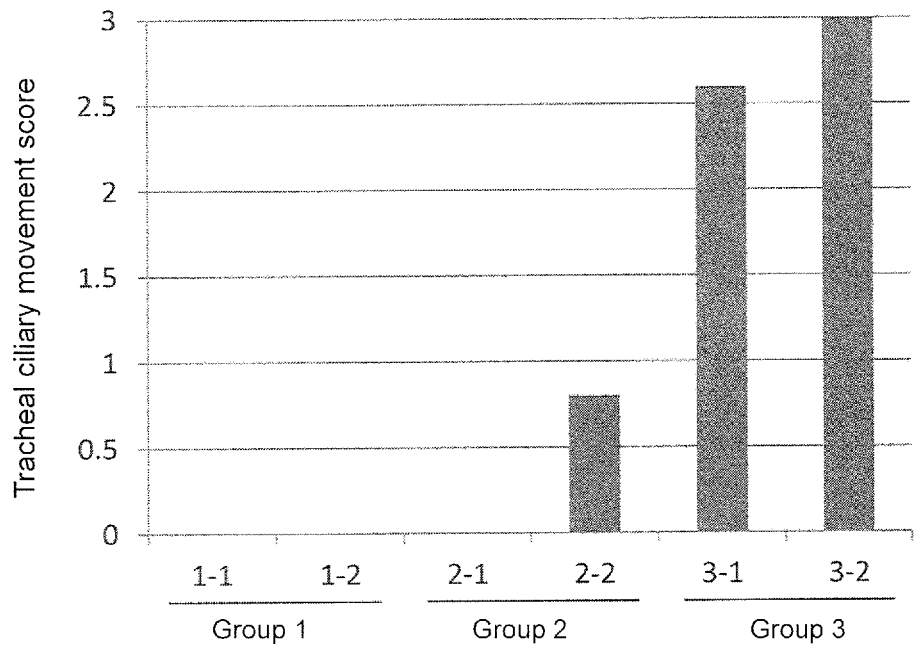
Figures 6, 13:
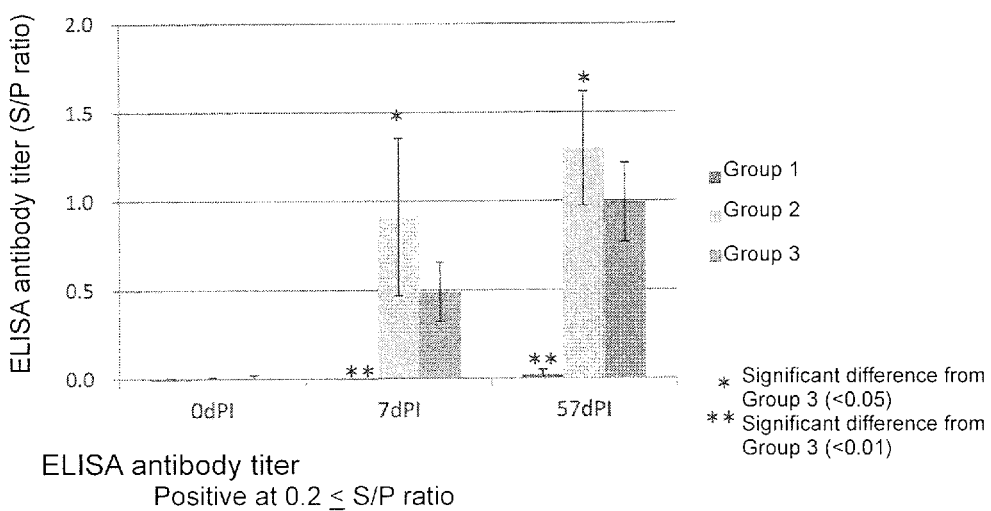

Changes in the egg-laying rate in each test group are shown in FIG. 13-1. Based on the egg-laying rate in each period of about 1 week, the rate decreased immediately after the challenge by not less than 15% in Group 2, and by not less than 30% in Group 3. Thereafter, the egg-laying rate gradually recovered in both groups (FIG. 13-2). The length of time required for recovery of the egg-laying rate to 90% or higher was 4 weeks in Group 2, and 6 weeks in Group 3. The number of chickens whose egg laying stopped continuously for 3 days or more after the challenge was 3 out of the 12 chickens in Group 2, and 6 out of the 12 chickens in Group 3. All chickens produced abnormal eggs (small and/or poor-quality eggs) after they began to lay eggs, and thereafter, they produced normal eggs (Table 13-3).

TABLE 13-3

Details of chickens that showed abnormal egg laying

| Test group | Number of chickens whose egg laying stopped continuously for 3 or more days after challenge (%) | Number of days of continuous stop | Presence or absence of abnormal egg | |
|---|---|---|---|---|
| | | | Abnormality of external egg quality | Abnormality of internal egg quality |
| Group 1 | 0 chicken (0%) | — | None | None |
| Group 2 | 3 chickens (25%) | 7 days | Small eggs | Slightly watery |
| | | 4 days | Small eggs | None |
| | | 4 days | Small eggs | None |
| Group 3 | 6 chickens (50%) | 9 days | Small eggs | Slightly watery |
| | | 8 days | Small eggs | Slightly watery |
| | | 4 days | Small eggs | Slightly watery |
| | | 4 days | Small eggs | None |
| | | 3 days | Small eggs | Slightly watery |
| | | 3 days | Small eggs | None |

(2) Quantification of Viral Gene

A. Quantification of Viral Gene in Swabs

Viral gene was detected from the buccal/cloacal swabs for the period from 7 to 14 dPI in Group 2, and for the period from 7 to 35 dPI in Group 3 (FIG. 13-3). In the period from 7 to 35 dPI, Group 2 showed significantly smaller amounts of gene relative to Group 3 (P<0.05 or P<0.01). At 57 dPI, virus gene was not detected in any test group.

B. Quantification of Viral Gene in Organs

At 7 dPI, viral gene was detected from the trachea, kidney, and oviduct in Group 2 and Group 3 (FIG. 3-4). The amount of viral gene in Group 2 tended to be smaller than in Group 3. At 57 dPI, virus gene was not detected in any test group.

(3) Tracheal Ciliary Movement Score

At 7 dPI, two chickens in Group 3 showed severe suppression of tracheal ciliary movement. In contrast, in Group 2, one chicken showed no suppression, and another chicken showed mild suppression (FIG. 13-5).

(4) Antibody Test (ELISA)

At 7 dPI and 57 dPI, the ELSA antibody titer in Group 2 was significantly higher than in Group 3 (P<0.05) (FIG. 13-6).

<Conclusion>

From the frequency of occurrence and the period of occurrence of the egg-laying disorder after the challenge, and from the test results indicating systemic viral infection, it was suggested that the egg-laying disorder was less severe in the vaccine test group than in the challenge control group, and hence that the IB liposome vaccine is effective against the egg-laying disorder.

14. Evaluation of Effectiveness of Test Vaccines (5)

<Object>

Based on the immunization method established in 12, the effectiveness of IBV-rNp-DSS against IBV heterologous field strains (5 strains) having various genotypes, which strains were recently isolated in Japan, was evaluated.

<Materials and Methods>

(1) Animal Test

The test group setting, the test schedule, and the heterologous field strains tested were as shown in Table 14-1, Table 14-2, and Table 14-3, respectively. Ten birds were tested in each immunization group, and three birds were tested in each challenge control group. Based on the immunization method established in 12, IBV-rNp-DSS was administered by fine spraying (100 ng/dose) at 0 day old and 14 days old in the immunization groups. At 21 days old, the immunization groups and the challenge control groups were challenged by intratracheal inoculation of 3.0 log $EID_{50}$ (50 µL/body) of the various heterologous field strains. The birds were kept under observation of clinical symptoms and the egg-laying performance, and then subjected to autopsy on Day 7 after the challenge, for collecting organs (trachea and kidney).

TABLE 14-1

Test group setting

| Test group | Number of birds | Test vaccine | Challenge strain |
|---|---|---|---|
| 1 | 10 | IBV-rNp-DSS | JP-I type field strain |
| 2 | 10 | | JP-II type field strain |
| 3 | 10 | | JP-III type field strain |
| 4 | 10 | | 4/91 type field strain |
| 5 | 10 | | Mass type field strain |
| 6 | 3 | None | JP-I type field strain |
| 7 | 3 | | JP-II type field strain |
| 8 | 3 | | JP-III type field strain |
| 9 | 3 | | 4/91 type field strain |
| 10 | 3 | | Mass type field strain |

TABLE 14-2

Test schedule

| Test group | Age in days | | | |
|---|---|---|---|---|
| | 0 | 14 | 21 | 28 |
| Immunization groups (Groups 1 to 5) | Immunization | Immunization | Challenge | Autopsy |
| Challenge control groups (Groups 6 to 10) | | | | |

TABLE 14-3

Heterologous field strains used for the challenge

| No. | Strain name (abbreviation) | S1 genotype | Prefecture in which the strain was isolated | Year in which the strain was isolated |
|---|---|---|---|---|
| 1 | JP-I type field strain | JP-I | Kagawa | 2009 |
| 2 | JP-II type field strain | JP-II | Niigata | 2010 |
| 3 | JP-III type field strain | JP-III | Ehime | 2011 |
| 4 | 4/91 type field strain | 4/91 | Iwate | 2004 |
| 5 | Mass type field strain | Mass | Hyogo | 2011 |

(2) Evaluation Items

A. Evaluation Based on the Tracheal Ciliary Movement Score

See 4. A significance test was carried out by the Dunnett's multiple comparison test method.

B. Quantification of Viral Gene in Organs

See 4. A significance test was carried out by the Student-t test method.

<Results>

(1) Tracheal Ciliary Movement Score

Figures 1, 14:
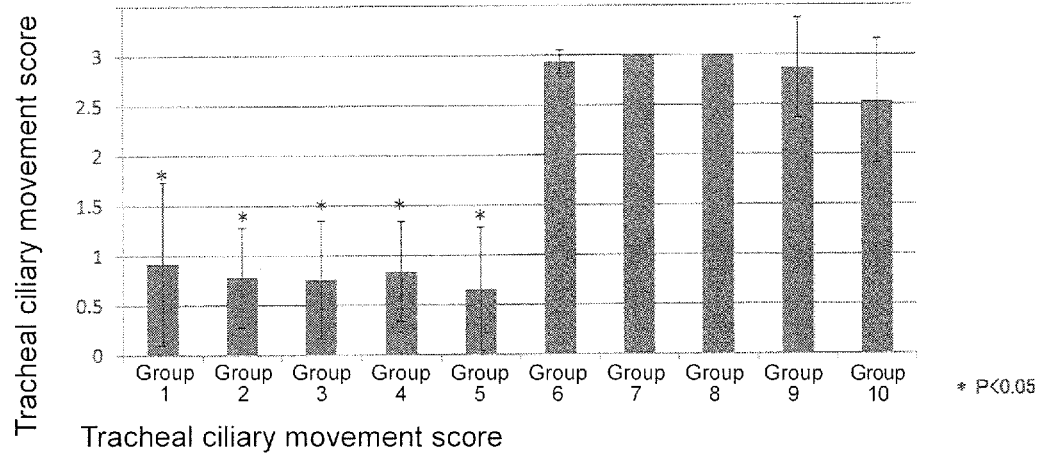
Figures 2, 14:
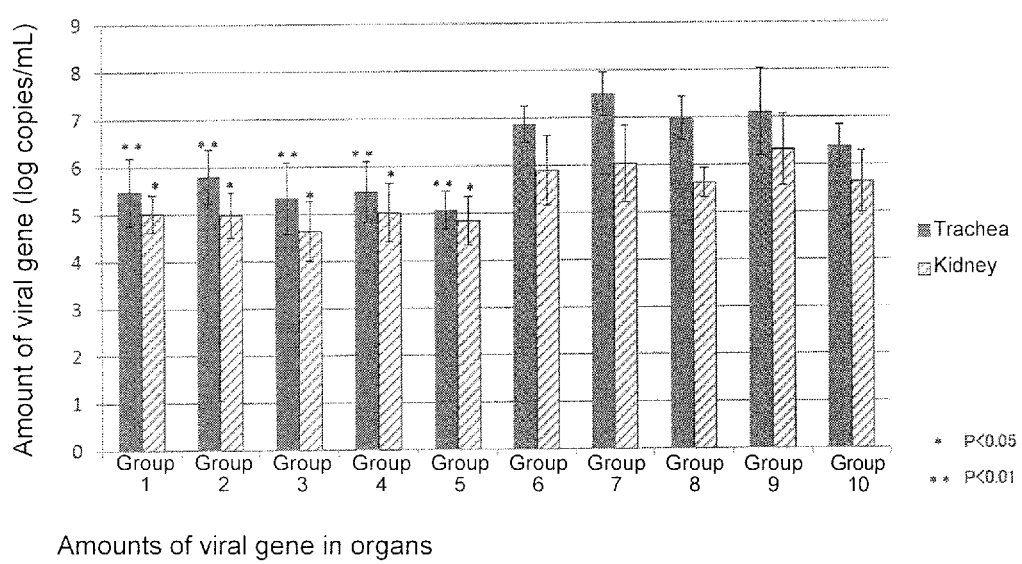

While all challenge control groups showed severe suppression of tracheal ciliary movement, the immunization groups showed no suppression or only mild suppression in a large number of birds, resulting in significantly lower average scores compared to the challenge control groups (P<0.05) (FIG. 14-1, Table 14-4).

TABLE 14-4

Score distribution of the tracheal ciliary movement score

| Test group | Number of birds with each score | | |
|---|---|---|---|
| | 0 to less than 1 | 1 to less than 2 | 2 or more |
| Group 1 | 4 | 5 | 1 |
| Group 2 | 5 | 3 | 2 |
| Group 3 | 6 | 3 | 1 |
| Group 4 | 5 | 3 | 2 |
| Group 5 | 6 | 4 | 0 |
| Group 6 | 0 | 0 | 3 |
| Group 7 | 0 | 0 | 3 |
| Group 8 | 0 | 0 | 3 |
| Group 9 | 0 | 0 | 3 |
| Group 10 | 0 | 0 | 3 |

(2) Quantification of Viral Gene

Compared to the challenge control groups, the immunization groups using any challenge strain showed significantly smaller amounts of viral gene in the trachea and kidney 7 days after the challenge (P<0.05 or P<0.01) (FIG. 14-2).

<Conclusion>

As a result of the use of IBV-rNp-DSS based on the immunization method established in 12, a high symptom onset-reducing effect was found against any of the heterologous field strains (5 strains) having various genotypes.

15. Preparation of PRRSV Liposome Vaccine

<Object>

For preparation of a liposome vaccine against porcine reproductive and respiratory syndrome virus (hereinafter referred to as PRRSV), full-length nucleocapsid (N) protein, which is relatively highly conserved among PRRSV strains, was prepared as an antigen for the vaccine, using recombinant E. coli. A PRRS liposome vaccine was prepared using this antigen.

<Materials and Methods>
(1) Determination of Antigen Region

N protein (ORF7 gene region), which has been reported to be relatively highly conserved among PRRSV strains, was used as the antigen region.

(2) Preparation of Recombinant N Protein by E. coli Expression System

From the PRRSV wt-7 strain, which was isolated in ZEN-NOH Institute of Animal Health, genome extraction was carried out, and the full-length ORF7 region (SEQ ID NO:27) encoding N protein (SEQ ID NO:28) was amplified by PCR, followed by inserting the amplified product into a vector plasmid containing a His-tag. The resulting plasmid was introduced into E. coli for cloning, to transform the E. coli. Subsequently, plasmid was extracted from E. coli in which the insertion of the target gene could be confirmed by PCR, and the extracted plasmid was introduced into E. coli for protein expression, to transform the E. coli. The recombinant E. coli was subjected to induction of expression using LB medium supplemented with ampicillin, and IPTG or to induction of expression using TB medium supplemented with 10 mM lactose, to allow expression of recombinant N protein (hereinafter referred to as PRRSV-rNp). The bacterial cells were disrupted by sonication, and affinity purification using the His tag was carried out. SDS-PAGE was carried out to confirm that the expressed protein is found at the position corresponding to the assumed molecular weight.

The RT-PCR, and the PCR for confirmation of the insertion of the target gene were carried out using the following primers.

Fw:
CCCC<u>CATATG</u>GCCATGCCAAATAACAACGGCAA (SEQ ID NO: 29; the underline indicates an NdeI recognition site)

Rv:
TTT<u>GGATCC</u>TCATGCTGAGGGTGATGATA (SEQ ID NO: 30; the underline indicates a BamHI recognition site)

The following reagents and the like were used.
Nucleic acid extraction: QIAamp Viral RNA Mini Kit (QIAGEN)
PCR apparatus: PCR Thermal Cycler Dice (registered trademark) Gradient (TP600) (TaKaRa)
Gel purification of DNA: QiAquick Gel Extraction Kit (QIAGEN)
Restriction enzymes: NdeI and BamHI (Takara)
Vector plasmid: pET-15b (Novagen)
Competent cells: The E. coli JM109 strain (TaKaRa) was used for the cloning, and the E. coli BL21 (DE3) strain (BioDynamics Laboratory, Inc.) was used for the protein expression.
Ligation: Ligation high (TOYOBO)
Sequence analysis: Outsourcing to FASMAC Co., Ltd.
Affinity purification using the His tag: Profinia Protein Purification System (BioRad)

(3) Liposome Modification

By the same method as 2. (1-1) (Liposome Modification of Antigen by DSS Method), PRRSV-rNp was bound to the liposome surface to prepare a PRRS liposome vaccine (hereinafter referred to as PRRSV-rNp-DSS).

<Results>
(1) Search for Antigen Region

The base sequence of the full-length ORF7 region of the PRRSV wt-7 strain is shown in SEQ ID NO:27.

(2) Preparation of Recombinant Protein by E. coli Expression System

A. Preparation of Recombinant E. coli

RT-PCR was carried out using total RNA extracted from the PRRSV wt-7 strain as a template, and amplification of the target gene fragment was confirmed. Regarding the recombinant N protein (rNp), the amplicon and the plasmid vector (pET-15b) were ligated to each other utilizing the same two kinds of restriction enzyme regions (NdeI and BamHI) in each of them, and then sequence analysis was carried out to confirm that the insertion occurred in a normal manner. E. coli for cloning (JM109) was transformed with the plasmid vector, and then cultured, followed by recovering the amplified plasmid. E. coli for expression, the BL21 (DE3) strain, was transformed with the plasmid recovered, to prepare recombinant E. coli for expression of PRRSV-rNp.

B. Induction of Expression and Purification of Recombinant Protein

The recombinant E. coli for expression of PRRSV-rNp, after preculture in liquid LB medium supplemented with ampicillin, was added at 1/100 volume to LB medium supplemented with ampicillin, and shake culture was carried out at 37° C. for 3 hours. After the start of the culture, when O.D.600 reached 0.5. IPTG (final concentration, 1 mM) was added thereto to induce expression, and then shake culture was further carried out for 3 hours. Alternatively, the recombinant E. coli for expression of PRRSV-rNp, after overnight culture in liquid LB medium supplemented with ampicillin, was added at about 1/100 volume to TB medium supplemented with 10 mM lactose, and shake culture was carried out at 25° C. for 3 days. Each of these cultured bacterial liquids was centrifuged at 3000 rpm for 40 min at 4° C. to collect the bacterial cell pellet. After resuspension of the pellet using a binding buffer (20 mM Tris, 500 mM NaCl, 20 mM imidazole; pH 7.4), the bacterial cells were disrupted by sonication. Subsequently, centrifugation was carried out at 6000 rpm for 30 minutes to collect the soluble fraction (supernatant), and affinity purification was carried out to recover the fraction of interest, that is, the PRRSV-rNp fraction. SDS-PAGE is known to show apparent molecular weights which are larger by several kilodaltons due to the effect of tag modification (His-tag) to antigens. As a result of SDS-PAGE, and also Western blotting using a mouse anti-PRRSV-rNp antibody, a clear band was found near the assumed molecular weight (about 14 kDa), and the expression level of PRRSV-rNp was higher in the case where TB medium supplemented with 10 mM lactose was used (FIG. 15-1).

C. Preparation of Liposome Vaccine (Same as 2.)

The freeze-dried DSS-bound oleic acid liposome powder (90 mg lipid/vial) was rehydrated with distilled water to a total volume of 2 mL per coupling reaction. To the resulting liquid, 0.5 mL of the antigen, whose concentration was adjusted to 10 mg/mL, was added, and the resulting mixture was stirred using a stirrer at room temperature for 48 hours. Three coupling reactions were carried out. A column packed with CL-4B (4% cross-linked agarose gel) was equilibrated with PBS, and then the antigen-liposome mixture was applied thereto, to recover a fraction of antigen-bound liposomes by the molecular sieve effect (9 mL/coupling). The fraction was then filtered (0.45 μm) to provide a test vaccine (PRRSV-rNp-DSS). The liquid volume of the test vaccine finally collected was about 25 mL.

<Conclusion>

PRRSV-rNp, which uses the PRRSV wt-7 strain as a template, was prepared using recombinant E. coli. PRRSV-rNp-DSS was prepared using the PRRSV-rNp as an antigen. The immunogenicity of PRRSV-rNp-DSS was evaluated in the animal test described below.

16. Evaluation of Immunogenicity of PRRS Liposome Vaccine Using Mice

<Object>

Using mice, the immunogenicity of the PRRS liposome vaccine PRRSV-rNp-DSS prepared in 15, was evaluated.

<Materials and Methods
1) Animal Test

The test group setting and the test schedule were as shown in Table 15-1 and FIG. 16-1. Three-week-old mice of two different lineages, BALB/cCrSlc mice (hereinafter referred to as BALB/c mice) and C57BL/6NCrSlc mice (hereinafter referred to as B6 mice), were introduced, and their immunization was begun at 4 weeks old. The immunizing material was administered into footpads of each mouse three times in total at 2-week intervals. Blood collection and autopsy were carried out over time.

TABLE 15-1

Test group setting

| Test group | Test mice | Number of mice tested | Immunization material | Amount of PRRSV-rNp antigen (µg/mL) | Administration route | Dose (µL/dose · body) |
|---|---|---|---|---|---|---|
| Group 1 | BALB/cCrSlc | 8 | PBS | — | Footpads | 100 (50 µL for each foot) |
| Group 2 | | | Liposome alone | — | | |
| Group 3 | | | PRRSV-rNp | 200 | | |
| Group 4 | | | PRRSV-rNp-DSS | 200 | | |
| Group 5 | C57BL/6NCrSlc | | PBS | — | | |
| Group 6 | | | Liposome alone | — | | |
| Group 7 | | | PRRSV-rNp | 200 | | |
| Group 8 | | | PRRSV-rNp-DSS | 200 | | |

(2) Evaluation Items
A. Evaluation of Antigen-Specific Lymphocyte Activity by ELISPOT Mouse IFN-γ ELISPOT BASIC (MABTECH) was used. One week after the third immunization (35 dPI), three mice were subjected to autopsy to collect the spleen. To a suspension of the spleen cells ($5 \times 10^5$ cells/mL), 2 µg/well of PRRSV-rNp was added as a stimulating antigen, and the cells were then cultured in a 5% $CO_2$ incubator at 37° C. for 24 hours. The lymphocytes activated in response to the stimulating antigen produced IFN-γ, and the sites of the production appeared as spots on the well. The number of the spots was counted to evaluate the antigen-specific mouse IFN-γ production-inducing ability.

B. Evaluation of Antibody-Inducing Ability by ELISA

Using mouse sera collected over time, and HRP-labeled goat anti-chicken IgG, IgG1, and IgG2a (BETHYL), ELISA using PRRSV-rNp as an antigen was carried out to measure IgG, IgG1, and IgG2α.

C. Evaluation of Neutralizing Antibody-Inducing Ability

The sera in Groups 3, 4, 7, and 8, in which increases in the antibody titer against PRRSV-rNp were found in the ELISA, were subjected to measurement of the neutralizing antibody titer by a neutralization test using MARC145 cells and the PRRSV wt-7 strain.

3. Results
(1) Evaluation of IFN-γ Production-Inducing Ability

As a result of the evaluation of the IFN-γ production-inducing ability in the lymphocytes in the spleen by the ELISPOT assay, increases in the number of spots in response to the stimulating antigen (PRRSV-rNp) were found in Group 4 and Group 8, in which PRRSV-rNp-DSS was administered (FIG. 16-2).

(2) Evaluation of Antibody-Inducing Ability

As a result of the ELISA for IgG, IgG1, and IgG2a using PRRSV-rNp as an antigen, increases in the antibody against PRRSV-rNp were found in the PRRSV-rNp administration groups (Groups 3 and 7) and the PRRSV-rNp-DSS administration groups (Groups 4 and 8) (FIG. 16-3, FIG. 16-4, FIG. 16-5). The BALB/c mice and the B6 mice showed differences in the degree of increase in the antibody titer. This was thought to be due to the fact that the major component of IgG is IgG1 in BALB/c, and IgG2a in B6.

(3) Evaluation of Neutralizing Antibody-Inducing Ability

The serum samples in the groups of 3, 4, 7, and 8, in which increases in the antibody titer against PRRSV-rNp were found in the ELISA, were subjected to measurement of the neutralizing antibody titer. However, none of the samples showed an increase in the neutralizing antibody titer (Table 15-2). This was thought to be due to the fact that N protein of PRRSV is not a neutralization activity region.

TABLE 15-2

Neutralizing antibody titer in serum

| | Neutralizing antibody titer | | |
|---|---|---|---|
| Test group | After first immunization | After second immunization | After third immunization |
| Group 3 | <2 | <2 | <2 |
| Group 4 | <2 | <2 | <2 |
| Group 7 | <2 | <2 | <2 |
| Group 8 | <2 | <2 | <2 |

<Conclusion>

In the mice to which PRRSV-rNp-DSS was administered, activation of IFN-γ-producing lymphocytes and antibody induction were found. It was thus confirmed that PRRSV-rNp-DSS has a certain level of immunogenicity.

17. Evaluation of Effectiveness of PRRS Liposome Vaccine Using Pigs
<Object>

Using pigs, the effectiveness of the PRRS liposome vaccine PRRSV-rNp-DSS prepared in 15, was evaluated.

2. Materials and Methods
(1) Animal Test

Figures 1, 17:
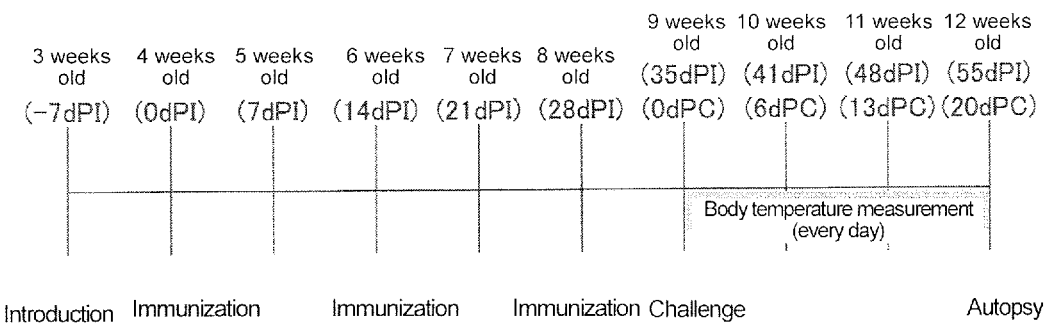
Figures 2, 17:
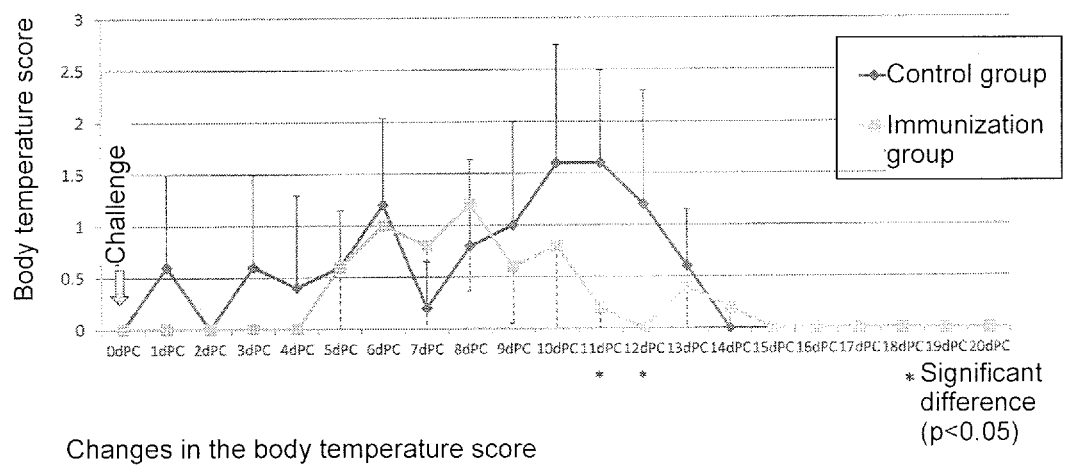
Figures 3, 17:
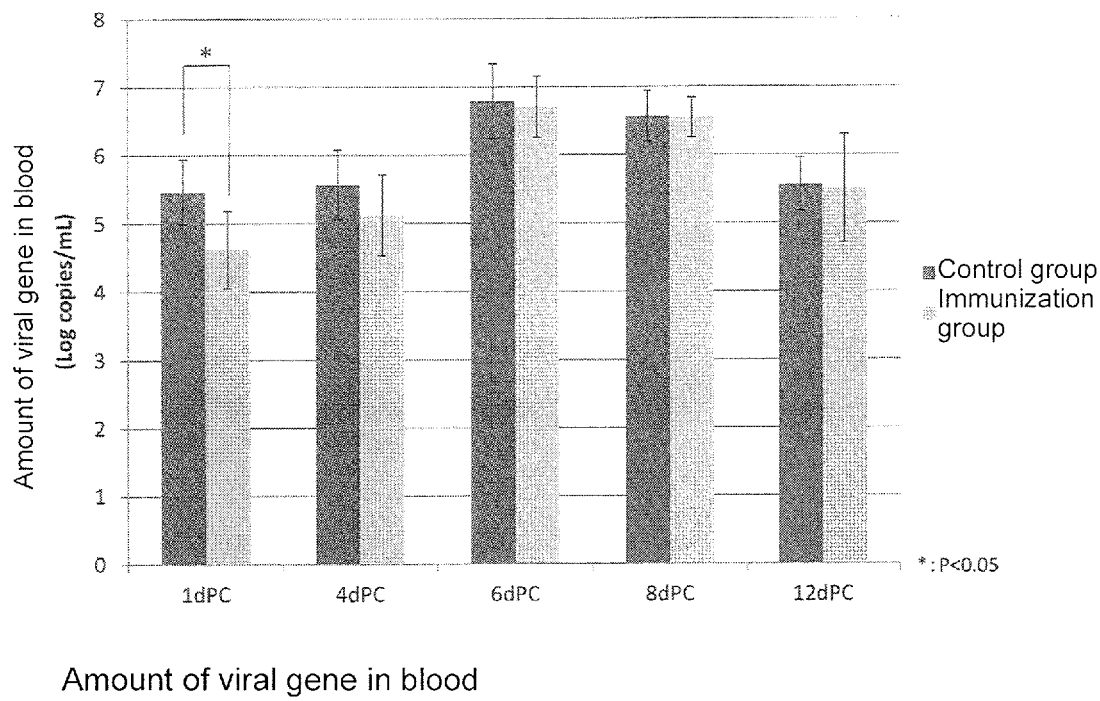
Figures 4, 17:
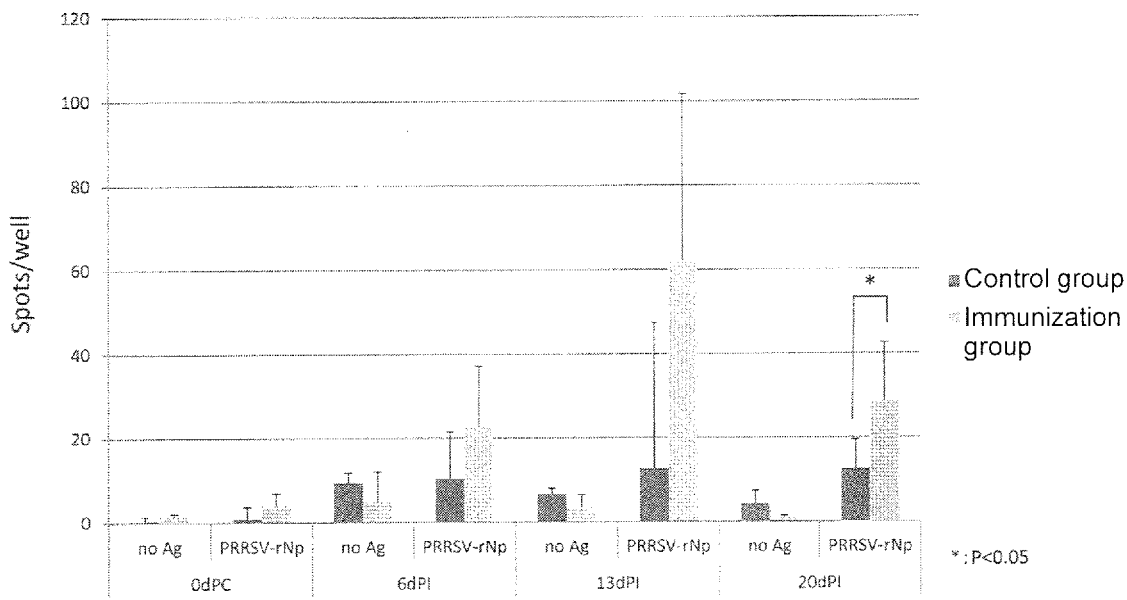

The test group setting and the test schedule were as shown in Table 16-1 and FIG. 17-1. Three-week-old SPF pigs were introduced, and their immunization was begun at 4 weeks old. In the immunization group, PRRSV-rNp-DSS was injected into the cervical muscle three times in total at 2-week intervals. Blood was collected over time from after the start of the immunization until the end of the test. One week after the third immunization, that is, at 9 weeks old (35 dPI), each pig was challenged by transnasal administration of 2 mL (1 mL to each side of nose) of $10^{5.0}$ $TCID_{50}$/mL of the PRRSV wt-7 strain. Twenty days after the challenge, that is, at 12 weeks old (55 dPI), autopsy was carried out to collect lung.

TABLE 16-1

Test group setting

| Test group | Number of pigs tested | Immunization material | Amount of PRRSV-rNp antigen (μg/mL) | Administration route | Number of times of immunization | Dose (mL/dose · body) |
|---|---|---|---|---|---|---|
| Group 1 (control group) | 5 | PBS | — | Intra-cervical muscle | 3 times | 2 |
| Group 2 (immunization group) | | PRRSV-rNp-DSS | 200 | | | |

(2) Evaluation Items

A. Body Temperature Measurement

The body temperature was measured every day from 0 dPC to 20 dPC.

B. Amount of Viral Gene in Blood

Blood collected over time from 1 dPC to 12 dPC was subjected to measurement of the amount of viral gene by real-time PCR.

C. Evaluation of Antigen-Specific Lymphocyte Activity by ELISPOT

Porcine IFN-γ ELISpot BASIC (HRP) (MABTECH) was used. From blood collected over time from 0 dPC to 20 dPC, PBMCs were prepared, and 2 μg/well of PRRSV-rNp as a stimulating antigen was added to a PBMC suspension (3.0× $10^5$ cells/well), followed by performing culture in a 5% $CO_2$ incubator at 37° C. for 24 hours. The lymphocytes activated in response to the stimulating antigen produced IFN-γ, and the sites of the production appeared as spots on the well. The number of the spots was counted to evaluate the antigen-specific porcine IFN-γ production-inducing ability.

D. Evaluation of Antigen-Specific Lymphocyte Activity by ELISA

Porcine IFN-γ was detected by sandwich ELISA using Porcine IFNγ Mab, clone P2F6 (Thermo Scientific) and Biotin Mouse Anti-Pig IFNγ Clone P2C11 (BD Biosciences). From blood collected over time from 0 dPC to 20 dPC, PBMCs were prepared, and 20 μg/well of PRRSV-rNp as a stimulating antigen was added to a PBMC suspension (2.0×$10^6$ cells/well), followed by performing culture in a 5% $CO_2$ incubator at 37° C. for 72 hours. Thereafter, the supernatant was collected, and detection of porcine IFN-γ was carried out by the sandwich ELISA.

E. Histopathological Examination

The lung collected at 20 dPC was subjected to histopathological examination for scoring of the severity of the lesion. The scoring was carried out according to P. G. HALBUR, et al. Comparison of the Pathogenicity of Two US Porcine Reproductive and Respiratory Syndrome Virus Isolates with that of the Lelystad Virus. Veterinary Pathology 32:648-660 (1995).

F. Evaluation of Antibody-Inducing Ability by ELISA

The sera collected over time were subjected to measurement of antibody against PRRSV-rNp by ELISA. As a secondary antibody, HRP-labeled rabbit anti-pig IgG (MP Biomedicals) was used.

<Results>

A. Body Temperature Measurement

Although there was a variation among the individuals, the body temperature after the challenge tended to be lower in the immunization group, and was significantly lower at 11 dPC and 12 dPC (FIG. 17-2).

B. Amount of Viral Gene in Blood

In the immunization group, the amount of viral gene in blood was significantly lower at 1 dPC, but was almost the same at 6 dPC and later compared to that in the control group (FIG. 17-3).

C. Evaluation of Antigen-Specific Lymphocyte Activity by ELISPOT

The immunization group showed activity of lymphocytes in specific response to PRRSV-rNp from 0 dPC to 20 dPC. The degree of the activity tended to be high in the immunization group (FIG. 17-4).

D. Evaluation of Antigen-Specific Lymphocyte Activity by ELISA

The immunization group showed activity of lymphocytes in specific response to PRRSV-rNp from 0 dCP 0 dPC to 20 dPC. The degree of the activity tended to be high in the immunization group (FIG. 17-5).

E. Histopathological Examination

The immunization group tended to show low lung lesion scores (FIG. 17-6).

F. Evaluation of Antibody-inducing Ability by ELISA

After the second immunization (28 dPI), the immunization group showed induction of specific antibody (FIG. 17-7). After the challenge, the immunization group showed a remarkable increase in the antibody titer.

<Conclusion>

The pigs immunized with PRRSV-rNp-DSS showed a PRRSV-rNp-specific immune response, and tended to show reduction of the fever, amount of viral gene in blood, and lung lesion after the challenge.

The invention claimed is:

1. A method for vaccinating poultry comprising:
administering a vaccine to poultry by fine spray administration with a droplet size of not more than 150 μm, said vaccine comprising liposomes each comprising an antigen molecule(s) bound to the surface thereof, the antigen molecule(s) being a full-length nucleocapsid protein of infectious bronchitis virus whose amino acid sequence is shown in SEQ ID NO:2.

2. The method according to claim 1, wherein the droplet particle size is not more than 120 μm.

3. A method for vaccinating pigs, comprising:
administering a vaccine to a pig, said vaccine comprising liposomes each comprising an antigen molecule(s) bound to the surface thereof, the antigen molecule(s) being a full-length nucleocapsid protein of porcine reproductive and respiratory syndrome virus whose amino acid sequence is shown in SEQ ID NO: 28.

4. The method according to claim 3, wherein said vaccine is administered by intravenous administration, subcutaneous administration, intradermal administration, intramuscular administration, transnasal administration, transdermal administration, rectal administration, intratracheal administration, inhalation administration, or ocular instillation administration.

5. The method according to claim 1, wherein the antigen molecule(s) is/are bound to the liposome surface by covalent bonding.

6. The method according to claim 5, wherein the antigen molecule(s) is/are bound to the liposome surface by reaction between an amino group in the antigen molecule and a succinimide group in a suberic acid succinimide group represented by —CO—(CH$_2$)$_6$—COO—C$_4$H$_4$NO$_2$ on the liposome surface.

7. The method according to claim 1, wherein said vaccine is administered to poultry two or more times at intervals of at least one week.

8. The method according to claim 3, wherein the antigen molecule(s) is/are bound to the liposome surface by covalent bonding.

9. The method according to claim 8, wherein the antigen molecule(s) is/are bound to the liposome surface by reaction between an amino group in the antigen molecule and a succinimide group in a suberic acid succinimide group represented by $-CO-(CH_2)_6-COO-C_4H_4NO_2$ on the liposome surface.

10. The method according to claim 3, wherein said vaccine is administered to a pig two or more times at intervals of at least one week.

* * * * *

SEQUENCE LISTING

<160> NUMBER OF SEQ ID NOS: 30

<210> SEQ ID NO 1
<211> LENGTH: 1230
<212> TYPE: DNA
<213> ORGANISM: Avian infectious bronchitis virus
<220> FEATURE:
<221> NAME/KEY: CDS
<222> LOCATION: (1)..(1230)

<400> SEQUENCE: 1

```
atg gca agc ggt aag gca act gga aag aca gat gcc cca gcg cca gtc    48
Met Ala Ser Gly Lys Ala Thr Gly Lys Thr Asp Ala Pro Ala Pro Val
1               5                   10                  15 atc aaa cta gga gga cca aag cca cct aaa gtt ggt tct tcc gga aat    96
Ile Lys Leu Gly Gly Pro Lys Pro Pro Lys Val Gly Ser Ser Gly Asn
            20                  25                  30 gca tct tgg ttt caa gca ata aaa gcc aag aag cta aat tca cct caa   144
Ala Ser Trp Phe Gln Ala Ile Lys Ala Lys Lys Leu Asn Ser Pro Gln
        35                  40                  45 cct aag ttt gaa ggt agc ggt gtt cct gat aat gaa aat cta aaa aca   192
Pro Lys Phe Glu Gly Ser Gly Val Pro Asp Asn Glu Asn Leu Lys Thr
    50                  55                  60 agc cag caa cat gga tac tgg aga cgc caa gct agg ttt aag cca agt   240
Ser Gln Gln His Gly Tyr Trp Arg Arg Gln Ala Arg Phe Lys Pro Ser
65                  70                  75                  80 aaa ggc gga aga aaa cca gtc cca gat gct tgg tac ttc tat tat act   288
Lys Gly Gly Arg Lys Pro Val Pro Asp Ala Trp Tyr Phe Tyr Tyr Thr
                85                  90                  95 gga aca gga cca gcc gct gac ctg aat tgg ggt gat agc caa gat ggt   336
Gly Thr Gly Pro Ala Ala Asp Leu Asn Trp Gly Asp Ser Gln Asp Gly
            100                 105                 110 ata gtg tgg gtt gct gca aag ggt gct gat gtt aaa tct aga tct aac   384
Ile Val Trp Val Ala Ala Lys Gly Ala Asp Val Lys Ser Arg Ser Asn
        115                 120                 125 cag ggt aca agg gac cct gac aag ttt gac caa tat ccg cta cga ttc   432
Gln Gly Thr Arg Asp Pro Asp Lys Phe Asp Gln Tyr Pro Leu Arg Phe
    130                 135                 140 tcg gac gga gga cct gat ggt aat ttc cgt tgg gac ttc att cct ctg   480
Ser Asp Gly Gly Pro Asp Gly Asn Phe Arg Trp Asp Phe Ile Pro Leu
145                 150                 155                 160 aat cgc ggt agg agt gga aga tca aca gca gct tca tca gca gca tct   528
Asn Arg Gly Arg Ser Gly Arg Ser Thr Ala Ala Ser Ser Ala Ala Ser
                165                 170                 175 agt aga gca ccg tcg cgt gaa ggc tcg cgt ggt cgt aga agt ggt tct   576
Ser Arg Ala Pro Ser Arg Glu Gly Ser Arg Gly Arg Arg Ser Gly Ser
            180                 185                 190 gaa gat gat ctt att gct cgt gca gca aag ata atc cag gat cag cag   624
Glu Asp Asp Leu Ile Ala Arg Ala Ala Lys Ile Ile Gln Asp Gln Gln
        195                 200                 205 aag aag ggt tct cgc att act aag gct aag gct gat gaa atg gct cat   672
Lys Lys Gly Ser Arg Ile Thr Lys Ala Lys Ala Asp Glu Met Ala His
    210                 215                 220 cgc cgg tat tgc aag cgc act att cca cct ggt tat aag gtt gat caa   720
Arg Arg Tyr Cys Lys Arg Thr Ile Pro Pro Gly Tyr Lys Val Asp Gln
225                 230                 235                 240 gtc ttt ggt ccc cgt act aaa ggt aag gag gga aat ttt ggt gat gac   768
Val Phe Gly Pro Arg Thr Lys Gly Lys Glu Gly Asn Phe Gly Asp Asp
                245                 250                 255 aag atg aat gag gaa ggt att aag gat ggg cgt gtt aca gca atg ctc   816
Lys Met Asn Glu Glu Gly Ile Lys Asp Gly Arg Val Thr Ala Met Leu
            260                 265                 270 aac cta gtc cca agc agc cat gct tgt ctt ttt gga agt aga gtg acg   864
Asn Leu Val Pro Ser Ser His Ala Cys Leu Phe Gly Ser Arg Val Thr
        275                 280                 285 ccc aaa ctt caa cca gat ggg ctg cac ttg aaa ttt gaa ttt gtt act   912
Pro Lys Leu Gln Pro Asp Gly Leu His Leu Lys Phe Glu Phe Val Thr
    290                 295                 300
```

```
gtg gtt tca cgt gat gat ccg cag ttt gat aat tat gtg aaa att tgt    960
Val Val Ser Arg Asp Asp Pro Gln Phe Asp Asn Tyr Val Lys Ile Cys
305             310                 315                 320 gat cag tgt gtc gat ggt gta gga acg cgt cca aaa gat gac gaa ccg   1008
Asp Gln Cys Val Asp Gly Val Gly Thr Arg Pro Lys Asp Asp Glu Pro
                325                 330                 335 aga cca aag tca cgc tca agt tca aga cct gct aca aga aca agt tct   1056
Arg Pro Lys Ser Arg Ser Ser Ser Arg Pro Ala Thr Arg Thr Ser Ser
            340                 345                 350 ccg gcg cca aaa caa cag cgc cct aag aag gag aaa aag tta aag aag   1104
Pro Ala Pro Lys Gln Gln Arg Pro Lys Lys Glu Lys Lys Leu Lys Lys
        355                 360                 365 cag gat gat gaa gtg gat aaa gcg ttg acc tca gat gag gag agg aac   1152
Gln Asp Asp Glu Val Asp Lys Ala Leu Thr Ser Asp Glu Glu Arg Asn
    370                 375                 380 aat gca cag ctg gag ttt gat gat gaa ccc aag gtg att aac tgg ggt   1200
Asn Ala Gln Leu Glu Phe Asp Asp Glu Pro Lys Val Ile Asn Trp Gly
385                 390                 395                 400 gac tca gca ctt ggt gaa aat gaa ctt tga                           1230
Asp Ser Ala Leu Gly Glu Asn Glu Leu
                405
```

<210> SEQ ID NO 2
<211> LENGTH: 409
<212> TYPE: PRT
<213> ORGANISM: Avian infectious bronchitis virus

<400> SEQUENCE: 2

```
Met Ala Ser Gly Lys Ala Thr Gly Lys Thr Asp Ala Pro Ala Pro Val
1               5                   10                  15

Ile Lys Leu Gly Gly Pro Lys Pro Pro Lys Val Gly Ser Ser Gly Asn
                20                  25                  30

Ala Ser Trp Phe Gln Ala Ile Lys Ala Lys Lys Leu Asn Ser Pro Gln
            35                  40                  45

Pro Lys Phe Glu Gly Ser Gly Val Pro Asp Asn Glu Asn Leu Lys Thr
        50                  55                  60

Ser Gln Gln His Gly Tyr Trp Arg Arg Gln Ala Arg Phe Lys Pro Ser
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Ser Gln Asp Gly
            100                 105                 110

Ile Val Trp Val Ala Ala Lys Gly Ala Asp Val Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Leu
145                 150                 155                 160

Asn Arg Gly Arg Ser Gly Arg Ser Thr Ala Ala Ser Ser Ala Ala Ser
                165                 170                 175

Ser Arg Ala Pro Ser Arg Glu Gly Ser Arg Gly Arg Arg Ser Gly Ser
            180                 185                 190

Glu Asp Asp Leu Ile Ala Arg Ala Ala Lys Ile Ile Gln Asp Gln Gln
        195                 200                 205

Lys Lys Gly Ser Arg Ile Thr Lys Ala Lys Ala Asp Glu Met Ala His
    210                 215                 220

Arg Arg Tyr Cys Lys Arg Thr Ile Pro Pro Gly Tyr Lys Val Asp Gln
```

```
              225                 230                 235                 240
Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Lys Phe Glu Phe Val Thr
    290                 295                 300

Val Val Ser Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Pro
                325                 330                 335

Arg Pro Lys Ser Arg Ser Ser Arg Pro Ala Thr Arg Thr Ser Ser
                340                 345                 350

Pro Ala Pro Lys Gln Gln Arg Pro Lys Lys Glu Lys Lys Leu Lys Lys
                355                 360                 365

Gln Asp Asp Glu Val Asp Lys Ala Leu Thr Ser Asp Glu Glu Arg Asn
    370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405

<210> SEQ ID NO 3
<211> LENGTH: 669
<212> TYPE: DNA
<213> ORGANISM: Avian infectious bronchitis virus
<220> FEATURE:
<221> NAME/KEY: CDS
<222> LOCATION: (1)..(669)

<400> SEQUENCE: 3 atg gaa aat tgc aca ctt aac tca gag cag gca att ctg ctt ttt aaa        48
Met Glu Asn Cys Thr Leu Asn Ser Glu Gln Ala Ile Leu Leu Phe Lys
1               5                   10                  15 gag tat aat tta ttt ata acc gca ttc ctg ttg ttc cta acc ata cta        96
Glu Tyr Asn Leu Phe Ile Thr Ala Phe Leu Leu Phe Leu Thr Ile Leu
                20                  25                  30 ctt cag tat gga tac gca act agg agc cgg gtt att tac ata ctg aaa       144
Leu Gln Tyr Gly Tyr Ala Thr Arg Ser Arg Val Ile Tyr Ile Leu Lys
            35                  40                  45 atg ata gtg tta tgg tgc ttt tgg ccc ctc aac att gca gta ggt gta       192
Met Ile Val Leu Trp Cys Phe Trp Pro Leu Asn Ile Ala Val Gly Val
        50                  55                  60 att tca tgt ata tac cca cca aac aca gga ggt ctt gtc gca gcg ata       240
Ile Ser Cys Ile Tyr Pro Pro Asn Thr Gly Gly Leu Val Ala Ala Ile
65                  70                  75                  80 ata ctt aca gtg ttt gcg tgt ctt tct ttt gta ggt tat tgg att cag       288
Ile Leu Thr Val Phe Ala Cys Leu Ser Phe Val Gly Tyr Trp Ile Gln
                85                  90                  95 agt ttt aga ctc ttt aaa agg tgt aga tct tgg tgg tcc ttt aac ccc       336
Ser Phe Arg Leu Phe Lys Arg Cys Arg Ser Trp Trp Ser Phe Asn Pro
                100                 105                 110 gaa tcc aat gcc gta ggt tca ata ctt ctt aca aat ggt caa caa tgt       384
Glu Ser Asn Ala Val Gly Ser Ile Leu Leu Thr Asn Gly Gln Gln Cys
            115                 120                 125 aat ttt gct ata gag agt gta cct atg gta cta tct cct att att aag       432
```

```
Asn Phe Ala Ile Glu Ser Val Pro Met Val Leu Ser Pro Ile Ile Lys
        130                 135                 140 aat ggt gct ctt tat tgt gaa ggt cag tgg ctt gct aaa tgt gaa cca       480
Asn Gly Ala Leu Tyr Cys Glu Gly Gln Trp Leu Ala Lys Cys Glu Pro
145                 150                 155                 160 gac cac ttg cct aga gat att ttt gtt tgc aca cct gat aga cgt aat       528
Asp His Leu Pro Arg Asp Ile Phe Val Cys Thr Pro Asp Arg Arg Asn
                165                 170                 175 atc tat cgt atg gtg cag aaa tac act ggt gac caa agc gga aat aag       576
Ile Tyr Arg Met Val Gln Lys Tyr Thr Gly Asp Gln Ser Gly Asn Lys
            180                 185                 190 aaa agg ttt gct aca ttt gtc tat gca aag cag tca gta gac act ggc       624
Lys Arg Phe Ala Thr Phe Val Tyr Ala Lys Gln Ser Val Asp Thr Gly
        195                 200                 205 gag cta gaa agt gta gca aca gga ggg ggt agt ctt tac aca taa           669
Glu Leu Glu Ser Val Ala Thr Gly Gly Gly Ser Leu Tyr Thr
210                 215                 220
```

<210> SEQ ID NO 4
<211> LENGTH: 222
<212> TYPE: PRT
<213> ORGANISM: Avian infectious bronchitis virus

<400> SEQUENCE: 4

```
Met Glu Asn Cys Thr Leu Asn Ser Gln Ala Ile Leu Leu Phe Lys
1               5                   10                  15

Glu Tyr Asn Leu Phe Ile Thr Ala Phe Leu Leu Phe Leu Thr Ile Leu
                20                  25                  30

Leu Gln Tyr Gly Tyr Ala Thr Arg Ser Arg Val Ile Tyr Ile Leu Lys
            35                  40                  45

Met Ile Val Leu Trp Cys Phe Trp Pro Leu Asn Ile Ala Val Gly Val
        50                  55                  60

Ile Ser Cys Ile Tyr Pro Pro Asn Thr Gly Gly Leu Val Ala Ala Ile
65                  70                  75                  80

Ile Leu Thr Val Phe Ala Cys Leu Ser Phe Val Gly Tyr Trp Ile Gln
                85                  90                  95

Ser Phe Arg Leu Phe Lys Arg Cys Arg Ser Trp Trp Ser Phe Asn Pro
            100                 105                 110

Glu Ser Asn Ala Val Gly Ser Ile Leu Leu Thr Asn Gly Gln Gln Cys
        115                 120                 125

Asn Phe Ala Ile Glu Ser Val Pro Met Val Leu Ser Pro Ile Ile Lys
    130                 135                 140

Asn Gly Ala Leu Tyr Cys Glu Gly Gln Trp Leu Ala Lys Cys Glu Pro
145                 150                 155                 160

Asp His Leu Pro Arg Asp Ile Phe Val Cys Thr Pro Asp Arg Arg Asn
                165                 170                 175

Ile Tyr Arg Met Val Gln Lys Tyr Thr Gly Asp Gln Ser Gly Asn Lys
            180                 185                 190

Lys Arg Phe Ala Thr Phe Val Tyr Ala Lys Gln Ser Val Asp Thr Gly
        195                 200                 205

Glu Leu Glu Ser Val Ala Thr Gly Gly Gly Ser Leu Tyr Thr
210                 215                 220
```

<210> SEQ ID NO 5
<211> LENGTH: 420
<212> TYPE: DNA
<213> ORGANISM: Avian infectious bronchitis virus
<220> FEATURE:

<221> NAME/KEY: CDS
<222> LOCATION: (1)..(420)

<400> SEQUENCE: 5

```
atg gca agc ggt aag gca act gga aag aca gat gcc cca gcg cca gtc      48
Met Ala Ser Gly Lys Ala Thr Gly Lys Thr Asp Ala Pro Ala Pro Val
1               5                   10                  15 atc aaa cta gga gga cca aag cca cct aaa gtt ggt tct tcc gga aat      96
Ile Lys Leu Gly Gly Pro Lys Pro Pro Lys Val Gly Ser Ser Gly Asn
            20                  25                  30 gca tct tgg ttt caa gca ata aaa gcc aag aag cta aat tca cct caa     144
Ala Ser Trp Phe Gln Ala Ile Lys Ala Lys Lys Leu Asn Ser Pro Gln
        35                  40                  45 cct aag ttt gaa ggt agc ggt gtt cct gat aat gaa aat cta aaa aca     192
Pro Lys Phe Glu Gly Ser Gly Val Pro Asp Asn Glu Asn Leu Lys Thr
    50                  55                  60 agc cag caa cat gga tac tgg aga cgc caa gct agg ttt aag cca agt     240
Ser Gln Gln His Gly Tyr Trp Arg Arg Gln Ala Arg Phe Lys Pro Ser
65                  70                  75                  80 aaa ggc gga aga aaa cca gtc cca gat gct tgg tac ttc tat tat act     288
Lys Gly Gly Arg Lys Pro Val Pro Asp Ala Trp Tyr Phe Tyr Tyr Thr
                85                  90                  95 gga aca gga cca gcc gct gac ctg aat tgg ggt gat agc caa gat ggt     336
Gly Thr Gly Pro Ala Ala Asp Leu Asn Trp Gly Asp Ser Gln Asp Gly
            100                 105                 110 ata gtg tgg gtt gct gca aag ggt gct gat gtt aaa tct aga tct aac     384
Ile Val Trp Val Ala Ala Lys Gly Ala Asp Val Lys Ser Arg Ser Asn
        115                 120                 125 cag ggt aca agg gac cct gac aag ttt gac caa tat                     420
Gln Gly Thr Arg Asp Pro Asp Lys Phe Asp Gln Tyr
    130                 135                 140
```

<210> SEQ ID NO 6
<211> LENGTH: 140
<212> TYPE: PRT
<213> ORGANISM: Avian infectious bronchitis virus

<400> SEQUENCE: 6

```
Met Ala Ser Gly Lys Ala Thr Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Ala Ile Lys Ala Lys Lys Leu Asn Ser Pro Gln
        35                  40                  45

Pro Lys Phe Glu Gly Ser Gly Val Pro Asp Asn Glu Asn Leu Lys Thr
    50                  55                  60

Ser Gln Gln His Gly Tyr Trp Arg Arg Gln Ala Arg Phe Lys Pro Ser
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Ser Gln Asp Gly
            100                 105                 110

Ile Val Trp Val Ala Ala Lys Gly Ala Asp Val Lys Ser Arg Ser Asn
        115                 120                 125

Gln Gly Thr Arg Asp Pro Asp Lys Phe Asp Gln Tyr
    130                 135                 140
```

<210> SEQ ID NO 7
<211> LENGTH: 420

```
<212> TYPE: DNA
<213> ORGANISM: Avian infectious bronchitis virus
<220> FEATURE:
<221> NAME/KEY: CDS
<222> LOCATION: (1)..(420)

<400> SEQUENCE: 7 tgg tac ttc tat tat act gga aca gga cca gcc gct gac ctg aat tgg     48
Trp Tyr Phe Tyr Tyr Thr Gly Thr Gly Pro Ala Ala Asp Leu Asn Trp
 1               5                  10                  15 ggt gat agc caa gat ggt ata gtg tgg gtt gct gca aag ggt gct gat     96
Gly Asp Ser Gln Asp Gly Ile Val Trp Val Ala Ala Lys Gly Ala Asp
             20                  25                  30 gtt aaa tct aga tct aac cag ggt aca agg gac cct gac aag ttt gac    144
Val Lys Ser Arg Ser Asn Gln Gly Thr Arg Asp Pro Asp Lys Phe Asp
         35                  40                  45 caa tat ccg cta cga ttc tcg gac gga gga cct gat ggt aat ttc cgt    192
Gln Tyr Pro Leu Arg Phe Ser Asp Gly Gly Pro Asp Gly Asn Phe Arg
 50                  55                  60 tgg gac ttc att cct ctg aat cgc ggt agg agt gga aga tca aca gca    240
Trp Asp Phe Ile Pro Leu Asn Arg Gly Arg Ser Gly Arg Ser Thr Ala
 65                  70                  75                  80 gct tca tca gca gca tct agt aga gca ccg tcg cgt gaa ggc tcg cgt    288
Ala Ser Ser Ala Ala Ser Ser Arg Ala Pro Ser Arg Glu Gly Ser Arg
                 85                  90                  95 ggt cgt aga agt ggt tct gaa gat gat ctt att gct cgt gca gca aag    336
Gly Arg Arg Ser Gly Ser Glu Asp Asp Leu Ile Ala Arg Ala Ala Lys
            100                 105                 110 ata atc cag gat cag cag aag aag ggt tct cgc att act aag gct aag    384
Ile Ile Gln Asp Gln Gln Lys Lys Gly Ser Arg Ile Thr Lys Ala Lys
        115                 120                 125 gct gat gaa atg gct cat cgc cgg tat tgc aag cgc                    420
Ala Asp Glu Met Ala His Arg Arg Tyr Cys Lys Arg
    130                 135                 140

<210> SEQ ID NO 8
<211> LENGTH: 140
<212> TYPE: PRT
<213> ORGANISM: Avian infectious bronchitis virus

<400> SEQUENCE: 8

Trp Tyr Phe Tyr Tyr Thr Gly Thr Gly Pro Ala Ala Asp Leu Asn Trp
 1               5                  10                  15

Gly Asp Ser Gln Asp Gly Ile Val Trp Val Ala Ala Lys Gly Ala Asp
             20                  25                  30

Val Lys Ser Arg Ser Asn Gln Gly Thr Arg Asp Pro Asp Lys Phe Asp
         35                  40                  45

Gln Tyr Pro Leu Arg Phe Ser Asp Gly Gly Pro Asp Gly Asn Phe Arg
 50                  55                  60

Trp Asp Phe Ile Pro Leu Asn Arg Gly Arg Ser Gly Arg Ser Thr Ala
 65                  70                  75                  80

Ala Ser Ser Ala Ala Ser Ser Arg Ala Pro Ser Arg Glu Gly Ser Arg
                 85                  90                  95

Gly Arg Arg Ser Gly Ser Glu Asp Asp Leu Ile Ala Arg Ala Ala Lys
            100                 105                 110

Ile Ile Gln Asp Gln Gln Lys Lys Gly Ser Arg Ile Thr Lys Ala Lys
        115                 120                 125

Ala Asp Glu Met Ala His Arg Arg Tyr Cys Lys Arg
    130                 135                 140
```

<210> SEQ ID NO 9
<211> LENGTH: 420
<212> TYPE: DNA
<213> ORGANISM: Avian infectious bronchitis virus
<220> FEATURE:
<221> NAME/KEY: CDS
<222> LOCATION: (1)..(420)

<400> SEQUENCE: 9

| tcg | cgt | gaa | ggc | tcg | cgt | ggt | cgt | aga | agt | ggt | tct | gaa | gat | gat | ctt | 48 |
| Ser | Arg | Glu | Gly | Ser | Arg | Gly | Arg | Arg | Ser | Gly | Ser | Glu | Asp | Asp | Leu | |
| 1 | | | | 5 | | | | | 10 | | | | | 15 | | |

| att | gct | cgt | gca | gca | aag | ata | atc | cag | gat | cag | cag | aag | aag | ggt | tct | 96 |
| Ile | Ala | Arg | Ala | Ala | Lys | Ile | Ile | Gln | Asp | Gln | Gln | Lys | Lys | Gly | Ser | |
| | | | 20 | | | | | 25 | | | | | 30 | | | |

| cgc | att | act | aag | gct | aag | gct | gat | gaa | atg | gct | cat | cgc | cgg | tat | tgc | 144 |
| Arg | Ile | Thr | Lys | Ala | Lys | Ala | Asp | Glu | Met | Ala | His | Arg | Arg | Tyr | Cys | |
| | 35 | | | | | 40 | | | | | 45 | | | | | |

| aag | cgc | act | att | cca | cct | ggt | tat | aag | gtt | gat | caa | gtc | ttt | ggt | ccc | 192 |
| Lys | Arg | Thr | Ile | Pro | Pro | Gly | Tyr | Lys | Val | Asp | Gln | Val | Phe | Gly | Pro | |
| 50 | | | | | 55 | | | | | 60 | | | | | | |

| cgt | act | aaa | ggt | aag | gag | gga | aat | ttt | ggt | gat | gac | aag | atg | aat | gag | 240 |
| Arg | Thr | Lys | Gly | Lys | Glu | Gly | Asn | Phe | Gly | Asp | Asp | Lys | Met | Asn | Glu | |
| 65 | | | | | 70 | | | | | 75 | | | | | 80 | |

| gaa | ggt | att | aag | gat | ggg | cgt | gtt | aca | gca | atg | ctc | aac | cta | gtc | cca | 288 |
| Glu | Gly | Ile | Lys | Asp | Gly | Arg | Val | Thr | Ala | Met | Leu | Asn | Leu | Val | Pro | |
| | | | | 85 | | | | | 90 | | | | | 95 | | |

| agc | agc | cat | gct | tgt | ctt | ttt | gga | agt | aga | gtg | acg | ccc | aaa | ctt | caa | 336 |
| Ser | Ser | His | Ala | Cys | Leu | Phe | Gly | Ser | Arg | Val | Thr | Pro | Lys | Leu | Gln | |
| | | | 100 | | | | | 105 | | | | | 110 | | | |

| cca | gat | ggg | ctg | cac | ttg | aaa | ttt | gaa | ttt | gtt | act | gtg | gtt | tca | cgt | 384 |
| Pro | Asp | Gly | Leu | His | Leu | Lys | Phe | Glu | Phe | Val | Thr | Val | Val | Ser | Arg | |
| | | 115 | | | | | 120 | | | | | 125 | | | | |

| gat | gat | ccg | cag | ttt | gat | aat | tat | gtg | aaa | att | tgt | | | | | 420 |
| Asp | Asp | Pro | Gln | Phe | Asp | Asn | Tyr | Val | Lys | Ile | Cys | | | | | |
| 130 | | | | | 135 | | | | | 140 | | | | | | |

<210> SEQ ID NO 10
<211> LENGTH: 140
<212> TYPE: PRT
<213> ORGANISM: Avian infectious bronchitis virus

<400> SEQUENCE: 10

Ser Arg Glu Gly Ser Arg Gly Arg Arg Ser Gly Ser Glu Asp Asp Leu
1               5                   10                  15

Ile Ala Arg Ala Ala Lys Ile Ile Gln Asp Gln Gln Lys Lys Gly Ser
            20                  25                  30

Arg Ile Thr Lys Ala Lys Ala Asp Glu Met Ala His Arg Arg Tyr Cys
        35                  40                  45

Lys Arg Thr Ile Pro Pro Gly Tyr Lys Val Asp Gln Val Phe Gly Pro
    50                  55                  60

Arg Thr Lys Gly Lys Glu Gly Asn Phe Gly Asp Asp Lys Met Asn Glu
65                  70                  75                  80

Glu Gly Ile Lys Asp Gly Arg Val Thr Ala Met Leu Asn Leu Val Pro
                85                  90                  95

Ser Ser His Ala Cys Leu Phe Gly Ser Arg Val Thr Pro Lys Leu Gln
            100                 105                 110

Pro Asp Gly Leu His Leu Lys Phe Glu Phe Val Thr Val Val Ser Arg
        115                 120                 125

```
Asp Asp Pro Gln Phe Asp Asn Tyr Val Lys Ile Cys
        130                 135                 140
```

<210> SEQ ID NO 11
<211> LENGTH: 420
<212> TYPE: DNA
<213> ORGANISM: Avian infectious bronchitis virus
<220> FEATURE:
<221> NAME/KEY: CDS
<222> LOCATION: (1)..(420)

<400> SEQUENCE: 11

```
atg ctc aac cta gtc cca agc agc cat gct tgt ctt ttt gga agt aga      48
Met Leu Asn Leu Val Pro Ser Ser His Ala Cys Leu Phe Gly Ser Arg
1               5                   10                  15 gtg acg ccc aaa ctt caa cca gat ggg ctg cac ttg aaa ttt gaa ttt      96
Val Thr Pro Lys Leu Gln Pro Asp Gly Leu His Leu Lys Phe Glu Phe
                20                  25                  30 gtt act gtg gtt tca cgt gat gat ccg cag ttt gat aat tat gtg aaa    144
Val Thr Val Val Ser Arg Asp Asp Pro Gln Phe Asp Asn Tyr Val Lys
            35                  40                  45 att tgt gat cag tgt gtc gat ggt gta gga acg cgt cca aaa gat gac    192
Ile Cys Asp Gln Cys Val Asp Gly Val Gly Thr Arg Pro Lys Asp Asp
        50                  55                  60 gaa ccg aga cca aag tca cgc tca agt tca aga cct gct aca aga aca    240
Glu Pro Arg Pro Lys Ser Arg Ser Ser Ser Arg Pro Ala Thr Arg Thr
65                  70                  75                  80 agt tct ccg gcg cca aaa caa cag cgc cct aag aag gag aaa aag tta    288
Ser Ser Pro Ala Pro Lys Gln Gln Arg Pro Lys Lys Glu Lys Lys Leu
                85                  90                  95 aag aag cag gat gat gaa gtg gat aaa gcg ttg acc tca gat gag gag    336
Lys Lys Gln Asp Asp Glu Val Asp Lys Ala Leu Thr Ser Asp Glu Glu
            100                 105                 110 agg aac aat gca cag ctg gag ttt gat gat gaa ccc aag gtg att aac    384
Arg Asn Asn Ala Gln Leu Glu Phe Asp Asp Glu Pro Lys Val Ile Asn
        115                 120                 125 tgg ggt gac tca gca ctt ggt gaa aat gaa ctt tga                    420
Trp Gly Asp Ser Ala Leu Gly Glu Asn Glu Leu
130                 135
```

<210> SEQ ID NO 12
<211> LENGTH: 139
<212> TYPE: PRT
<213> ORGANISM: Avian infectious bronchitis virus

<400> SEQUENCE: 12

```
Met Leu Asn Leu Val Pro Ser Ser His Ala Cys Leu Phe Gly Ser Arg
1               5                   10                  15

Val Thr Pro Lys Leu Gln Pro Asp Gly Leu His Leu Lys Phe Glu Phe
                20                  25                  30

Val Thr Val Val Ser Arg Asp Asp Pro Gln Phe Asp Asn Tyr Val Lys
            35                  40                  45

Ile Cys Asp Gln Cys Val Asp Gly Val Gly Thr Arg Pro Lys Asp Asp
        50                  55                  60

Glu Pro Arg Pro Lys Ser Arg Ser Ser Ser Arg Pro Ala Thr Arg Thr
65                  70                  75                  80

Ser Ser Pro Ala Pro Lys Gln Gln Arg Pro Lys Lys Glu Lys Lys Leu
                85                  90                  95

Lys Lys Gln Asp Asp Glu Val Asp Lys Ala Leu Thr Ser Asp Glu Glu
            100                 105                 110
```

```
Arg Asn Asn Ala Gln Leu Glu Phe Asp Asp Glu Pro Lys Val Ile Asn
            115                 120                 125

Trp Gly Asp Ser Ala Leu Gly Glu Asn Glu Leu
        130                 135

<210> SEQ ID NO 13
<211> LENGTH: 657
<212> TYPE: DNA
<213> ORGANISM: Artificial Sequence
<220> FEATURE:
<223> OTHER INFORMATION: Chimeric protein Ch(N+M)
<220> FEATURE:
<221> NAME/KEY: CDS
<222> LOCATION: (1)..(657)

<400> SEQUENCE: 13 aaa ggc gga aga aaa cca gtc cca gat gct tgg tac ttc tat tat act      48
Lys Gly Gly Arg Lys Pro Val Pro Asp Ala Trp Tyr Phe Tyr Tyr Thr
1               5                   10                  15 gga aca gga cca gcc gct gac ctg aat tgg ggt gat agc caa gat ggt      96
Gly Thr Gly Pro Ala Ala Asp Leu Asn Trp Gly Asp Ser Gln Asp Gly
            20                  25                  30 ata gtg tgg gtt gct gca aag ggt gct gat gtt aaa tct aga tct aac     144
Ile Val Trp Val Ala Ala Lys Gly Ala Asp Val Lys Ser Arg Ser Asn
        35                  40                  45 cag ggt aca agg gac cct gac aag ttt gac caa tat ccg cta cga ttc     192
Gln Gly Thr Arg Asp Pro Asp Lys Phe Asp Gln Tyr Pro Leu Arg Phe
    50                  55                  60 tcg gac gga gga cct gat ggt aat ttc cgt tgg gac ttc att cct ctg     240
Ser Asp Gly Gly Pro Asp Gly Asn Phe Arg Trp Asp Phe Ile Pro Leu
65                  70                  75                  80 aat cgc ggt agg agt gga aga tca aca gca gct tca tca gca gca tct     288
Asn Arg Gly Arg Ser Gly Arg Ser Thr Ala Ala Ser Ser Ala Ala Ser
                85                  90                  95 agt aga gca ccg tcg cgt gaa ggc tcg cgt ggt cgt aga agt ggt tct     336
Ser Arg Ala Pro Ser Arg Glu Gly Ser Arg Gly Arg Arg Ser Gly Ser
            100                 105                 110 gaa gat gat ctt att gct cgt gca gca aag ata atc cag gat cag cag     384
Glu Asp Asp Leu Ile Ala Arg Ala Ala Lys Ile Ile Gln Asp Gln Gln
        115                 120                 125 aag aag ggt tct cgc att act aag gct aag gct gat gaa atg gct cat     432
Lys Lys Gly Ser Arg Ile Thr Lys Ala Lys Ala Asp Glu Met Ala His
    130                 135                 140 cgc cgg tat tgc aag cgc ggt cag tgg ctt gct aaa tgt gaa cca gac     480
Arg Arg Tyr Cys Lys Arg Gly Gln Trp Leu Ala Lys Cys Glu Pro Asp
145                 150                 155                 160 cac ttg cct aga gat att ttt gtt tgc aca cct gat aga cgt aat atc     528
His Leu Pro Arg Asp Ile Phe Val Cys Thr Pro Asp Arg Arg Asn Ile
                165                 170                 175 tat cgt atg gtg cag aaa tac act ggt gac caa agc gga aat aag aaa     576
Tyr Arg Met Val Gln Lys Tyr Thr Gly Asp Gln Ser Gly Asn Lys Lys
            180                 185                 190 agg ttt gct aca ttt gtc tat gca aag cag tca gta gac act ggc gag     624
Arg Phe Ala Thr Phe Val Tyr Ala Lys Gln Ser Val Asp Thr Gly Glu
        195                 200                 205 cta gaa agt gta gca aca gga ggg ggt agt ctt                         657
Leu Glu Ser Val Ala Thr Gly Gly Gly Ser Leu
    210                 215

<210> SEQ ID NO 14
<211> LENGTH: 219
<212> TYPE: PRT
```

<213> ORGANISM: Artificial Sequence
<220> FEATURE:
<223> OTHER INFORMATION: Synthetic Construct

<400> SEQUENCE: 14

| | | | | | | | | | | | | | | |
|---|---|---|---|---|---|---|---|---|---|---|---|---|---|---|
| Lys | Gly | Gly | Arg | Lys | Pro | Val | Pro | Asp | Ala | Trp | Tyr | Phe | Tyr | Tyr | Thr |
| 1 | | | | 5 | | | | | 10 | | | | | 15 | |
| Gly | Thr | Gly | Pro | Ala | Ala | Asp | Leu | Asn | Trp | Gly | Asp | Ser | Gln | Asp | Gly |
| | | | 20 | | | | | 25 | | | | | 30 | | |
| Ile | Val | Trp | Val | Ala | Ala | Lys | Gly | Ala | Asp | Val | Lys | Ser | Arg | Ser | Asn |
| | | | 35 | | | | | 40 | | | | | 45 | | |
| Gln | Gly | Thr | Arg | Asp | Pro | Asp | Lys | Phe | Asp | Gln | Tyr | Pro | Leu | Arg | Phe |
| | 50 | | | | | 55 | | | | | 60 | | | | |
| Ser | Asp | Gly | Gly | Pro | Asp | Gly | Asn | Phe | Arg | Trp | Asp | Phe | Ile | Pro | Leu |
| 65 | | | | | 70 | | | | | 75 | | | | | 80 |
| Asn | Arg | Gly | Arg | Ser | Gly | Arg | Ser | Thr | Ala | Ala | Ser | Ala | Ala | Ser | |
| | | | | 85 | | | | | 90 | | | | | 95 | |
| Ser | Arg | Ala | Pro | Ser | Arg | Glu | Ser | Arg | Gly | Arg | Arg | Ser | Gly | Ser | |
| | | | | 100 | | | | | 105 | | | | | 110 | |
| Glu | Asp | Asp | Leu | Ile | Ala | Arg | Ala | Ala | Lys | Ile | Ile | Gln | Asp | Gln | Gln |
| | | | | 115 | | | | | 120 | | | | | 125 | |
| Lys | Lys | Gly | Ser | Arg | Ile | Thr | Lys | Ala | Lys | Ala | Asp | Glu | Met | Ala | His |
| | 130 | | | | | 135 | | | | | 140 | | | | |
| Arg | Arg | Tyr | Cys | Lys | Arg | Gly | Gln | Trp | Leu | Ala | Lys | Cys | Glu | Pro | Asp |
| 145 | | | | | 150 | | | | | 155 | | | | | 160 |
| His | Leu | Pro | Arg | Asp | Ile | Phe | Val | Cys | Thr | Pro | Asp | Arg | Arg | Asn | Ile |
| | | | | 165 | | | | | 170 | | | | | 175 | |
| Tyr | Arg | Met | Val | Gln | Lys | Tyr | Thr | Gly | Asp | Gln | Ser | Gly | Asn | Lys | Lys |
| | | | 180 | | | | | 185 | | | | | 190 | | |
| Arg | Phe | Ala | Thr | Phe | Val | Tyr | Ala | Lys | Gln | Ser | Val | Asp | Thr | Gly | Glu |
| | | | 195 | | | | | 200 | | | | | 205 | | |
| Leu | Glu | Ser | Val | Ala | Thr | Gly | Gly | Gly | Ser | Leu | | | | | |
| | | | 210 | | | | | 215 | | | | | | | |

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gcgtgtacct ctctagtat                                                        19

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gctacatgcc tatctbcctt a                                                     21

<210> SEQ ID NO 17
<211> LENGTH: 20
<212> TYPE: DNA
<213> ORGANISM: Artificial Sequence
<220> FEATURE:
<223> OTHER INFORMATION: primer

```
<400> SEQUENCE: 17
ggtagaaaac ttaacaatcc                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
aagactactt cctcctgttg                                              20

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19
aaggcctctg tcgacatggc aagcggtaag g                                 31

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
agaattcgca agctttcaaa gttcattttc accaa                             35

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
aaggcctctg tcgacatgga aaattgcaca cttaac                            36

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
agaattcgca agcttttatg tgtaaagact accccc                            36

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
taatacgact cactataggg                                              20

<210> SEQ ID NO 24
```

<211> LENGTH: 21
<212> TYPE: DNA
<213> ORGANISM: Artificial Sequence
<220> FEATURE:
<223> OTHER INFORMATION: primer

<400> SEQUENCE: 24
atgctagtta ttgctcagcg g    21

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
cccgaaaagt gccacctg    18

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gttctgaggt cattactgg    19

<210> SEQ ID NO 27
<211> LENGTH: 372
<212> TYPE: DNA
<213> ORGANISM: Porcine reproductive and respiratory syndrome virus
<220> FEATURE:
<221> NAME/KEY: CDS
<222> LOCATION: (1)..(372)

<400> SEQUENCE: 27

```
atg cca aat aac aac ggc aaa cag cag aag aaa agg aag ggg aac ggc      48
Met Pro Asn Asn Asn Gly Lys Gln Gln Lys Lys Arg Lys Gly Asn Gly
1               5                   10                  15 cag cca gtc aat cag ctg tgc cag atg ctg ggt aag att atc gcc cag      96
Gln Pro Val Asn Gln Leu Cys Gln Met Leu Gly Lys Ile Ile Ala Gln
            20                  25                  30 cag aac cag tct aga ggt aag gga ccg gga aac aga aac aag aag aaa     144
Gln Asn Gln Ser Arg Gly Lys Gly Pro Gly Asn Arg Asn Lys Lys Lys
        35                  40                  45 aac ccg gag aag ccc cat ttc cct cta gcg act gaa gat gac gtc aga     192
Asn Pro Glu Lys Pro His Phe Pro Leu Ala Thr Glu Asp Asp Val Arg
    50                  55                  60 cac cac ttc acc cct agt gag cgg caa ttg tgt ttg tcg tca atc cat     240
His His Phe Thr Pro Ser Glu Arg Gln Leu Cys Leu Ser Ser Ile His
65                  70                  75                  80 act gcc ttt aat cag ggc gct gga act tgt acc ctg tca gac tca ggg     288
Thr Ala Phe Asn Gln Gly Ala Gly Thr Cys Thr Leu Ser Asp Ser Gly
                85                  90                  95 aga ata agt tac act gtg gag ttt agt ttg cct acg cat cat acc gtg     336
Arg Ile Ser Tyr Thr Val Glu Phe Ser Leu Pro Thr His His Thr Val
            100                 105                 110 cgc cta att cgc gtc ata tca tca ccc tca gca tga                     372
Arg Leu Ile Arg Val Ile Ser Ser Pro Ser Ala
        115                 120
```

<210> SEQ ID NO 28

```
<211> LENGTH: 123
<212> TYPE: PRT
<213> ORGANISM: Porcine reproductive and respiratory syndrome virus

<400> SEQUENCE: 28

Met Pro Asn Asn Gly Lys Gln Gln Lys Lys Arg Lys Gly Asn Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Asn Arg Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile His
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Ile Ser Ser Pro Ser Ala
        115                 120

<210> SEQ ID NO 29
<211> LENGTH: 32
<212> TYPE: DNA
<213> ORGANISM: Artificial Sequence
<220> FEATURE:
<223> OTHER INFORMATION: primer

<400> SEQUENCE: 29
ccccatatgg ccatgccaaa taacaacggc aa                              32

<210> SEQ ID NO 30
<211> LENGTH: 29
<212> TYPE: DNA
<213> ORGANISM: Artificial Sequence
<220> FEATURE:
<223> OTHER INFORMATION: primer

<400> SEQUENCE: 30
tttggatcct catgctgagg gtgatgata                                  29
```